US009822358B2

(12) United States Patent
Pandolfi et al.

(10) Patent No.: US 9,822,358 B2
(45) Date of Patent: Nov. 21, 2017

(54) TREATMENT OF CANCERS WITH MICRO-RNA INHIBITORS

(71) Applicant: Beth Israel Deaconess Medical Center, Boston, MA (US)

(72) Inventors: Pier Paolo Pandolfi, Boston, MA (US); Sujung Song, Boston, MA (US)

(73) Assignee: BETH ISRAEL DEACONESS MEDICAL CENTER, Boston, MA (US)

(*) Notice: Subject to any disclaimer, the term of this patent is extended or adjusted under 35 U.S.C. 154(b) by 0 days.

(21) Appl. No.: 14/517,514

(22) Filed: Oct. 17, 2014

(65) Prior Publication Data

US 2015/0111949 A1  Apr. 23, 2015

Related U.S. Application Data

(60) Provisional application No. 61/892,806, filed on Oct. 18, 2013.

(51) Int. Cl.
  *C12N 15/113* (2010.01)
  *A61K 31/7115* (2006.01)
  *A61K 31/712* (2006.01)
  *A61K 31/7125* (2006.01)

(52) U.S. Cl.
  CPC ...... *C12N 15/113* (2013.01); *C12N 2310/113* (2013.01)

(58) Field of Classification Search
  None
  See application file for complete search history.

(56) References Cited

U.S. PATENT DOCUMENTS

| | | | |
|---|---|---|---|
| 2009/0239818 A1 | 9/2009 | Cheng | |
| 2013/0131088 A1* | 5/2013 | Penn | A61K 31/353 514/262.1 |
| 2013/0331433 A1* | 12/2013 | Thibonnier | C12N 15/113 514/44 A |

FOREIGN PATENT DOCUMENTS

| | | |
|---|---|---|
| EP | 2 243 833 A1 | 10/2010 |
| WO | 2010/056737 A2 | 5/2010 |
| WO | 2010/066384 A1 | 6/2010 |

OTHER PUBLICATIONS

Bao et al (Curr Drug Targets. 2012 13(14): 1858-1868).*
Tan (Biochemical and Biophysical Research Communications 417 (2012) 546-551).*
Xiong et al (FEBS J. 2010; 277:1684-1694).*
Li et al (British Journal of Haematology, 148, 69-79).*
Lionetti (Genes, Chromosomes & Cancer 48:521-531, 2009).*
Ninomiya (Cytogenet Genome Res 2012;136:246-255 ).*
Patel (Oncogene (2011) 30, 1290-1301).*
Ting et al (Biochemical and Biophysical Research Communications 394 (2010) 606-611).*
Xu et al (J. Cell Biol. vol. 193 No. 2 409-424, 2011).*
Song et al (Cell Jul. 18, 2013; 154(2):311-24).*
Heald (Clinical Lymphoma, vol. 1, Suppl. 1, S45-S49, 2000).*
Tu et al (Cell Physiol Biochem 2013;31:997-1008).*
Otsuki et al (Gene Funct. Dis. 2000, 1, 48-560).*
Pandyra et al (Mol Cancer Ther Nov. 2011 10; C170).*
Pandyra et al (http://www.seahorsebio.com/resources/posters/2011-11-12_pandrya_the_combination_of_statins_and_ dipyridamole_is_effective.pdf), retrieved from the web on Feb. 27, 2016.*
Kubatka et al (Biologia 66/4: 727-734, 2011).*
Nagueh et al (Eur J Clin Invest 2010; 40 (11): 976-983).*
Bauersachs et al (European Journal of Clinical Investigation (2007) 37: 852-859).*
Fantozzi et al (Breast Cancer Research 2006, 8:212.*
Clarke (Breast Cancer Research and Treatment 39: 69-86, 1996).*
Xiong et al (FEBS Journal 277 (2010) 1684-1694, 2010).*
Song et al (Cell 154, 311-324, Jul. 18, 2013).*
Song et al (Cell Stem Cell 13, 87-101, Jul. 3, 2013).*
Yu et al (Leukemia (2006) 20, 1-8, 2006).*
Lennox et al (Gene Therapy (2011) 18, 1111-1120).*
Zhang J. G. et al., "MicroRNA-21 (miR-21) represses tumor suppressor PTEN and promotes growth and invasion in non-small cell lung cancer (NSCLC)," Clinica Chimica Acta, Elsevier BV, vol. 411, No. 11-12, Mar. 16, 2010, pp. 846-852.
Park, Jong-Kook et al., "Antisense inhibition of microRNA-21 or -221 arrests cell cycle, induces apoptosis, and sensitizes the effects of gemcitabine in pancreatic adenocarcinoma," Pancreas, Lippincott Williams & Wilkins, vol. 38, No. 7, Oct. 2009, pp. e190-e199.
Huse, Jason T. et al., "The PTEN-regulating microRNA miR-26a is amplified in high-grade glioma and facilitates gliomagenesis in vivo," Genes and Development, vol. 23, No. 11, Jun. 1, 2009, pp. 1327-1337.
Poliseno, Laura et al., "Identification of the miR-106b similar to 25 MicroRNA Cluster as a Proto-Oncogenic PTEN-Targeting Intron That Cooperates with Its Host Gene MCM7 in Transformation," Science Signaling, vol. 3, No. 117, Apr. 13, 2010, pp. 1-13.
Tan, Hao-Xiang et al., "MicroRNA-9 reduces cell invasion and E-cadherin secretion in SK-Hep-1 cell," Medical Oncology, vol. 27, Jul. 2009, pp. 654-660.
Lou, Yanhui et al., "MicroRNA-21 promotes the cell proliferation, invasion and migration abilities in ovarian epithelial carcinomas through inhibiting the expression of PTEN protein," International Journal of Molecular Medicine, vol. 26, 2010, pp. 819-827.
Wan, Hai-Ying et al., "Regulation of the transcription factor NF-κB1 by microRNA-9 in human gastric adenocarcinoma," Molecular Cancer, Biomed Central, vol. 9, No. 16, Jan. 26, 2010, pp. 1-10.

(Continued)

*Primary Examiner* — Richard A Schnizer

(74) *Attorney, Agent, or Firm* — Morgan, Lewis & Bockius LLP

(57) ABSTRACT

The invention relates to the treatment and prevention of cancers, including blood-based cancers and breast cancers, by administering agents that inhibit the activity of microRNAs, including miR-22. Inhibitors can include oligonucleotides that are at least partially complementary to these miRNAs. In some embodiments, these inhibitors are chemically modified oligonucleotides, including locked nucleic acids (LNAs).

10 Claims, 114 Drawing Sheets

(56) References Cited

OTHER PUBLICATIONS

Laios, Alexandros et al., "Potential role of miR-9 and miR-223 in recurrent ovarian cancer," Molecular Cancer, Biomed Central, vol. 7, No. 35, Apr. 28, 2008, pp. 1-14.
Poliseno, Laura et al., "A coding-independent function of gene and pseudogene mRNAs regulates tumour biology," Nature, vol. 465, No. 7301, Jun. 24, 2010, pp. 1033-1038.
Aigner, Achim, "MicroRNAs (miRNAs) in cancer invasion and metastasis: therapeutic approaches based on metastasis-related miRNAs," Journal of Molecular Medicine, vol. 89, No. 5, Jan. 14, 2011, pp. 445-457.
Leslie, Nick R. et al., "Non-genomic loss of PTEN function in cancer: not in my genes," Trends in Pharmacological Sciences, vol. 32, No. 3, Mar. 2011, pp. 131-140.
Ma, Li et al., "miR-9, a MYC/MYCN-activated microRNA, regulates E-cadherin and cancer metastasis," Nature Cell Biology, vol. 12, No. 3, Sep. 1, 2010, pp. 247-256.
International Search Report and Written Opinion from PCT Application No. PCT/US2012/033359 (19 pages), dated Sep. 24, 2012.

\* cited by examiner

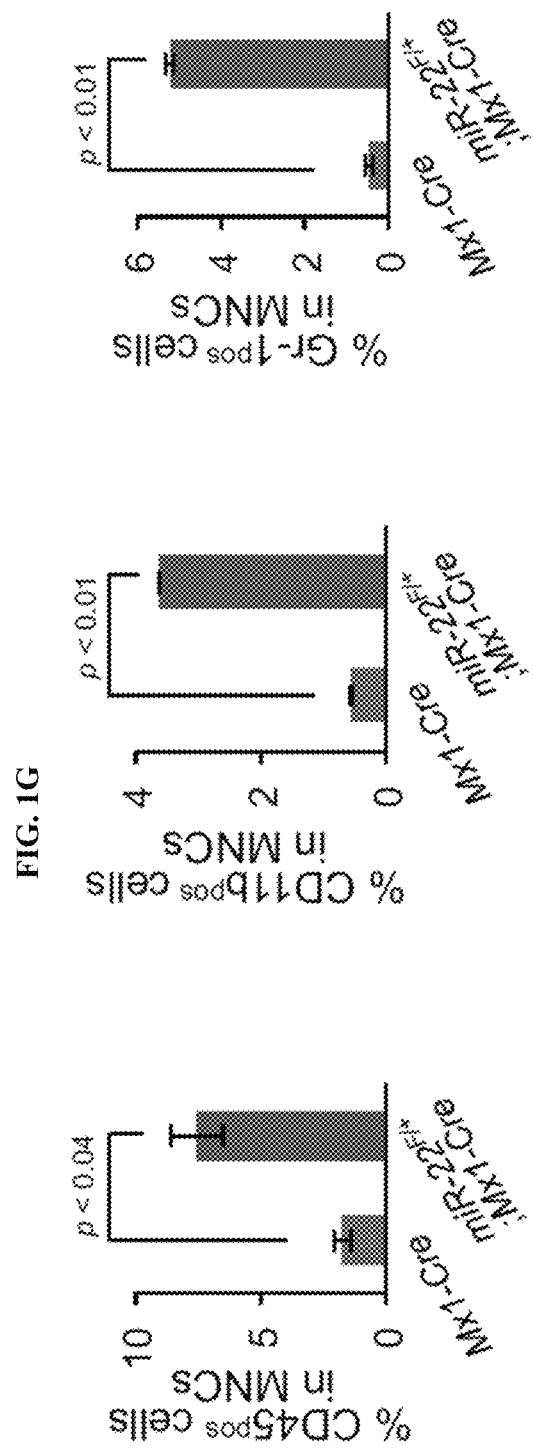

FIG. 7D

MDS

| D | Score of miR-22 | | |
|---|---|---|---|
| $r = -0.47$<br>$p = 2.4 \times 10^{-7}$ | 1 | 2 | 3 |
| Score of TET2   1 | 0 | 8 | 30 |
| 2 | 0 | 9 | 17 |
| 3 | 2 | 30 | 11 |

FIG. 7E

AML with MLD

| E | | Score of miR-22 | | | |
|---|---|---|---|---|---|
| $r = -0.75$ $p < 0.001$ | | 1 | 2 | 3 | 4 |
| Score of TET2 | 1 | 0 | 0 | 0 | 4 |
| | 2 | 0 | 8 | 3 | 2 |
| | 3 | 1 | 3 | 4 | 0 |

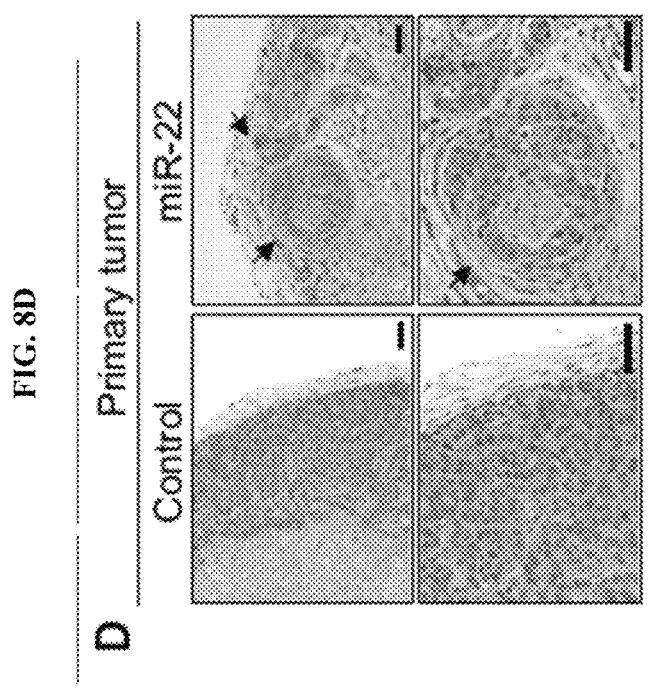

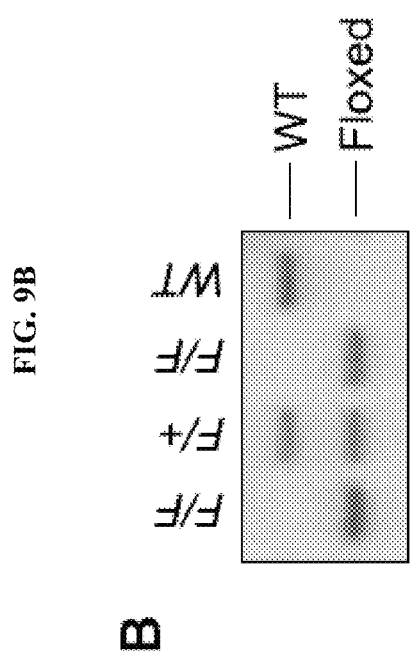

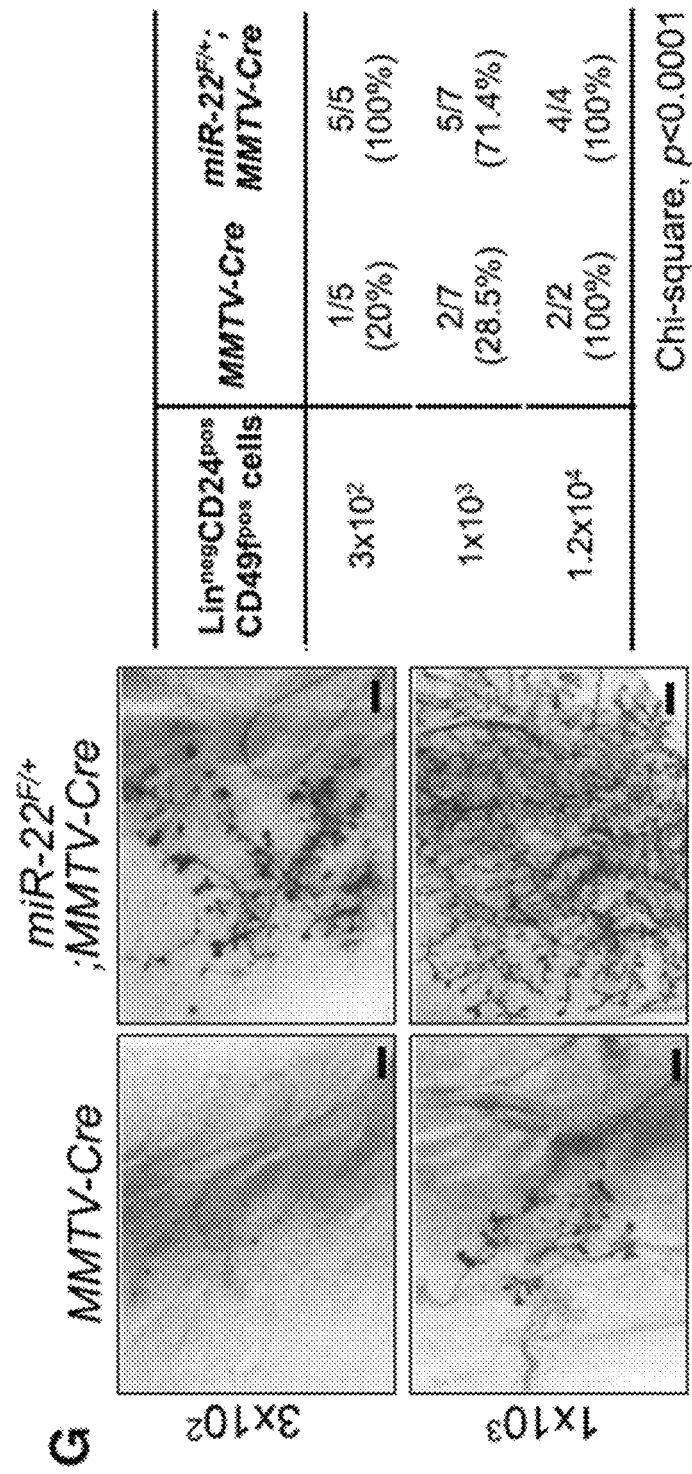

FIG. 12E

| | Mice with Lung metastasis |
|---|---|
| Cont. sponge | 3/4 (75%) |
| miR-22 sponge | 0/4 (0%) |

TREATMENT OF CANCERS WITH MICRO-RNA INHIBITORS

CROSS REFERENCE TO RELATED APPLICATIONS

This application claims priority to U.S. Provisional Patent Application No. 61/892,806, filed on Oct. 18, 2013, the entire contents of which are incorporated by reference herein.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: BID-002-SequenceListing.txt, dated recorded: Dec. 22, 2014, filed size 1 kilobyte).

GOVERNMENT SUPPORT

This invention was made with government support under grants CA141457 and CA082328 awarded by NIH. The government has certain rights in the invention.

FIELD OF THE INVENTION

The present invention relates to, in part, the treatment and prevention of cancers, including blood-based cancers and breast cancers, by administering agents that modulate the activity or expression of microRNAs. Specifically, the invention, in part, provides methods for treating or preventing blood-based cancers and breast cancers by inhibiting the expression and/or activity of miR-22.

BACKGROUND OF THE INVENTION

MicroRNAs (miRNA or miR) are nucleic acid molecules that are able to regulate the expression of target genes. See review by Carrington et al. *Science*, Vol. 301(5631):336-338, 2003). MiRNAs are typically short (usually 18-24 nucleotides) and act as repressors of target mRNAs by promoting their degradation, when their sequences are perfectly complementary, and/or by inhibiting translation, when their sequences contain mismatches.

Without being bound by theory, mature miRNAs are believed to be generated by RNA polymerase II (pol II) or RNA polymerase III (pol III; see Qi et al. (2006) *Cellular & Molecular Immunology*, Vol. 3:411-419) and arise from initial transcripts termed primary miRNA transcripts (pri-miRNAs). These pri-miRNAs are frequently several thousand bases long and are therefore processed to make the much shorter mature miRNAs. This processing is believed to occur in two steps. First, pri-miRNAs are processed in the nucleus by the RNase Drosha into about 70- to about 100-nucleotide hairpin-shaped precursors (pre-miRNAs). Second, after transposition to the cytoplasm, the hairpin pre-miRNAs are further processed by the RNase Dicer to produce a double-stranded miRNA. A mature miRNA strand is then incorporated into the RNA-induced silencing complex (RISC), where it associates with its target mRNA by base-pair complementarity and leads to suppression of protein expression.

Cancer is a group of diseases characterized by uncontrolled cell division which can lead to abnormal tissue and, in turn, disruption of normal physiologic processes and, possibly, death. Cancers have various etiologies and may be responsive to agents that affect aspects of these etiologies. For example, a reduction or loss of nucleic acids that are linked to cancer development may prove fruitful in the treatment of various cancers, including blood-based cancers and breast cancers. Such treatments may replace or supplement existing treatments. Therefore, there is a need in the art for treatment methods for cancers, including blood-based cancers and breast cancers, that target miRNAs that bind to cancer-related genes. Further, there is a need for agents designed to this end which can be produced cheaply, delivered effectively, and which display adequate bioavailability.

SUMMARY OF THE INVENTION

Accordingly, the present invention provides new methods for the treatment of cancers, including blood-based cancers and breast cancers.

In one aspect, the present invention provides a method of treating or preventing a cancer, including blood-based cancers and breast cancers, in a subject in need thereof, comprising administering to the subject an inhibitor of miR-22, including, for example, an antisense oligonucleotide directed to miR-22.

In some aspects, the present invention provides a method of treating or preventing leukemia in a subject in need thereof, comprising administering an effective amount of an antisense oligonucleotide directed to miR-22.

In other aspects, the present invention provides a method of preventing a metastasis in a subject in need thereof, comprising administering an effective amount of an antisense oligonucleotide directed to miR-22.

In other aspects, the present invention provides a method of preventing a decrease or causing an increase in TET2 expression and/or activity in a subject in need thereof, comprising administering an effective amount of an antisense oligonucleotide directed to miR-22.

BRIEF DESCRIPTION OF THE DRAWINGS

FIG. 1A shows that miR-22 is highly expressed in MDS patient samples. Expression levels of miR-22 in blasts in subtypes of MDS were measured by in situ hybridization analysis. Normal (n=37), RA (n=30), 5q- (n=5), RCMD (n=4), RARS (n=1), RAEB-1 (n=32), and RAEB-2 (n=35) are shown. Representative images of in situ hybridization for miR-22 in MDS patients and normal bone marrow are also shown (left). Insets of panels show miR-22 staining in blasts (arrow with B) and in differentiated myeloid cells (e.g., neutrophil, arrow with M) with a high magnification. The expression levels of miR-22 were also scored (right). The data were analyzed by Chi-square test. r, Pearson's r. Scale bars, 60 μm.

FIG. 1B shows that miR-22 overexpression correlates with poor survival rates of human MDS patients. MDS patients were divided into two groups: low-miR-22-expressing patients' group (miR-22 Score 1 or 2, n=49, upper line) and high-miR-22-expressing patients' group (miR-22 Score 3, n=58, lower line). Overall survival of these patients is demonstrated. p value was generated by a log-rank test.

FIG. 1C shows an overview of the experimental design for a conditional miR-22 expression in the hematopoietic compartment test. Two-month-old miR-22F/+;Mxl-Cre mice or Mxl-Cre littermate controls were treated with pIpC for two weeks. Two weeks after pIpC administration, c-Kit$^{pos}$Sca-1$^{pos}$Lin$^{neg}$ (KSL) cells were sorted to evaluate the characteristics of miR-22-expressing hematopoietic stem/progenitor cells. LTC-IC, long-term culture-initiating cells; BMT, bone marrow transplantation.

FIG. 1D shows the colony-forming capacity of miR-22-expressing progenitor cells. Two weeks after pIpC administration, sorted KSL cells from miR-22F/+;Mxl-Cre mice or littermate controls were cultured in semisolid medium. Counting and classification of colonies was performed in independent littermate pairs (n=3). GEMM, Colony-forming unit-granulocyte, erythroid, macrophage, and megakaryocyte (top shading of each bar); GM, Colony-forming unit-granulocyte and macrophage (second from top shading of each bar); M, Colony-forming unit-macrophage (second from bottom shading of each bar); E, Burst-forming unit-erythroid (bottom shading of each bar).

FIG. 1E shows miR-22 expression retains the ability to serially replate and generate colonies. In vitro colony replating assay was performed and colony counts in the indicated replatings were scored (n=3). N.D., nondetectable.

FIG. 1F shows that ectopic expression of miR-22 results in an increase of HSPCs during in vitro long-term culture with stromal cells. KSL cells, isolated as described herein, were cocultured with OP-9 stromal cells for 2 weeks. Maintained Lin$^{neg}$ cells and KSL cells were evaluated (n=3). Representative flow cytometry data of Lin$^{neg}$ and the KSL cells (left) are shown. Mean percentage±SD of KSL cells in Lin$^{neg}$ cells (middle) and mean absolute numbers±SD of CD45$^{pos}$KSL cells (right) are also shown.

FIG. 1G shows that miR-22 increases the myeloid compartment. The percentages of CD45$^{pos}$ cells (left), CD11b$^{pos}$ cells (middle), or Gr-1$^{pos}$ cells (right) in total mononuclear cells (MNCs) were investigated 2 weeks after the coculture with stromal cells from FIG. 1F (n=3).

FIG. 2A and FIG. 2B show data from Ly45.1 recipient mice that were transplanted with 1,500 KSL cells from miR-22F/+;Mxl-Cre mice (n=15) or littermate controls (n=10) after pIpC administration together with 4×10$^5$ Ly45.1/Ly45.2 competitor BM MNCs. Donor-derived chimerism in peripheral blood was analyzed 6 weeks after the transplantation. Representative flow data of the CD45.1/CD45.2 positivity (FIG. 2A) and the percentages of both donor-derived cells in myeloid (CD11b$^{pos}$ and/or Gr-1$^{pos}$) (FIG. 2B, left) and donor-derived myeloid cells in MNCs (B, right) of recipient mice are shown.

FIGS. 2C-2E show donor contribution in hematopoiesis of recipient mice 9 weeks after the transplantation. Representative flow data of the CD45.1/CD45.2 positivity with the percentages of donor-derived CD45.1$^{neg}$CD45.2$^{pos}$ cells (FIG. 2C, left) are shown. Mean percentages±SD of donor-derived cells in MNCs (FIG. 2C, right), myeloid cells (FIG. 2D), B cells (FIG. 2E, left), and T cells (FIG. 2E, right) are shown (n=10 for littermate controls and n=15 for miR-22F/+;Mxl-Cre).

FIG. 2F shows that c-Kit$^{pos}$ cells are observed in peripheral blood of recipient mice transplanted with KSL cells from miR-22F/+;Mxl-Cre mice. Representative flow cytometry data of c-Kit positivity in donor-derived cells (left) and the percentages of c-Kit$^{pos}$ cells in donor-derived cells (right) are shown. (n=10 for littermate controls and n=15 for miR-22F/+;Mxl-Cre). All error bars represent ±SD.

FIG. 3A and FIG. 3B show miR-22 overexpression leads to human MDS-like phenotypes characterized by defective erythropoiesis (FIG. 3A) and cytopenia (FIG. 3B) in miR-22 transgenic mice. After pIpC administration, 1,500 KSL cells from miR-22F/+;Mxl-Cre mice or littermate controls were transplanted into lethally irradiated Ly45.1 recipient mice with 4×10$^5$ Ly45.1/Ly45.2 competitor BM MNCs (n=10 for littermate controls and n=15 for miR-22F/+;Mxl-Cre). Twelve weeks after transplantation, peripheral blood of recipient mice was evaluated. Representative flow data of the Ter119/CD71 positivity (FIG. 3A, left) and the percentages of R1 (Ter119$^{neg}$CD71$^{pos}$) (FIG. 3A, middle) and R2 (Ter119$^{pos}$CD71$^{pos}$) (FIG. 3A, right) are shown. White blood cell (WBC) (FIG. 3B, left) and platelet (Plt) counts (FIG. 3B, right) are also shown.

FIG. 3C and FIG. 3D show that splenomegaly and myeloid infiltration into spleen were observed in recipient mice transplanted with KSL cells from miR-22F/+;Mxl-Cre mice. Representative images of spleens (FIG. 3C, left), spleen weight (n=3) (FIG. 3C, right), and representative flow data of the positivity of c-Kit and CD11b and/or Gr-1 in spleen (FIG. 3D) are shown.

FIG. 3E shows that miR-22 expression leads to a differentiation defect in erythroid compartment. Representative flow data of the Ter119/CD71 positivity in spleen are shown.

FIG. 4A and FIG. 4B show that miR-22 transgenic mice develop MDS-like hematological syndromes. Representative smears of peripheral blood of 8-month-old mice after pIpC administration are shown (FIG. 4A). Representative images of dysplastic erythroid cells (poikilocytosis, FIG. 4A; polychromasia, FIG. 4B-i, arrowhead), dysplastic platelets (giant platelet, FIG. 4B-i, arrow, FIG. 4B-vii), dysplastic neutrophils (hypersegmented neutrophils, FIG. 4B-ii-iv, arrows; a pseudo-Pelger-Huet anomaly, FIG. 4B-v and FIG. 4Bvi) and dysplastic blasts (FIG. 4B-viii arrows) in miR-22 transgenic mice are also shown. Scale bars, 50 μm (FIG. 4A) and 10 μm (FIG. 4B).

FIG. 4C shows that c-Kit$^{pos}$ immature blasts are increased in miR-22 transgenic mice. Representative flow cytometry data (left) and mean percentages±SD of c-Kit$^{pos}$ cells in Lin$^{neg}$ compartment (right) are shown (n=3).

FIG. 4D show disease-free survival of miR-22F/+;Mxl-Cre mice (n=26, top line) and littermate controls (n=13, bottom line).

FIG. 4E and FIG. 4F show representative lethal hematological syndromes observed in miR-22 transgenic mice. Representative images of spleens (FIG. 4E, left) and H&E staining (FIG. 4E, right) are shown. Scale bars, 100 μm. Representative smears of peripheral blood of miR-22 transgenic mice (6 months old) with increased myeloid blasts (FIG. 4F) are also shown. Scale bars, 20 μm.

FIG. 4G shows pie charts representing the disease spectrum in miR-22F/+;Mxl-Cre mice at the indicated ages (n=26). MPN, myeloproliferative neoplasm.

FIG. 5A and FIG. 5B show a reduction in the levels of Tet2 mRNA in miR-22 transgenic mice. Expression levels of miR-22 (left) and Tet2 mRNA (right) in mononuclear cells from peripheral blood (FIG. 5A) and bone marrow (BM) (FIG. 5B) of Mxl-Cre control or miR-22F/+;Mxl-Cre mice 2-3 weeks after pIpC administration were determined by real-time qPCR (n=6).

FIG. 5C shows that miR-22 expression results in a significant reduction in the levels of 5-hmC in the hematopoietic compartment. 5-hmC and 5-mC were evaluated by immunofluorescence analysis in BM cells isolated from miR-22F/+;Mxl-Cre mice and littermate controls 3 weeks after pIpC administration (left). Cells expressing high levels of 5-hmC show low levels of 5-mC (arrow) and conversely, cells expressing low levels of 5-hmC exhibit high levels of 5-mC (arrowhead). Bar graph depicts mean percentages±SD of cells expressing high levels of 5-hmC (n=3) (right). Scale bars, 10 μm.

FIG. 5D shows miR-22 expression leads to a significant reduction in global 5-hmC expression levels in the genome in BM cells. 5-hmC levels were analyzed by quantitative dot blot assay with genomic DNA purified from BM cells of miR-22F/+;Mxl-Cre or littermate control mice.

FIG. 5E shows plots that depict relative expression levels of putative Tet2 target genes (Aim2, Sp140, Igbt2, and Hal) in $CD150^{pos}CD48^{neg}Flt-3^{neg}CD34^{neg}KSL$ cells of miR-22F/+;Mxl-Cre mice and littermate controls ~2-3 weeks after pIpC administration (n=4). Ly6c1 and Actb were used as a Tet2 unrelated gene control and an internal control, respectively.

FIG. 5F and FIG. 5G show repression of putative downstream genes of Tet2 in miR-22 transgenic mice. Expression levels of Tet2, Sp140, and Aim2 mRNAs (FIG. 5F) or proteins (FIG. 5G) in BM of miR-22F/+;Mxl-Cre mice or littermate controls 2-3 weeks after pIpC administration were evaluated (n=3). All error bars indicate ±SD.

FIG. 6A and FIG. 6B show ectopic expression of TET2 reduces the colony-forming capacity of miR-22-expressing HSPCs. The sorted KSL cells from miR-22F/+ mice were infected with Cre-GFP or GFP control vector. GFP+KSL cells were resorted and infected with empty vector or TET2-expressing lentiviral particles. Cells were then incubated in semisolid medium. Colony replating assay was performed and the resulting colonies were counted at the indicated replatings (n=3) (FIG. 6A). Some of TET2 infected cells were also subjected to LTC-IC assay. Representative flow cytometry data of the positivity of c-Kit/Sca-1 in $Lin^{neg}CD45^{pos}$-gated cells 2 weeks after coculture with stromal cells and mean percentages±SD of KSL cells in $Lin^{neg}CD45^{pos}$ (in brackets) are shown (n=3) (FIG. 6B, left). Colony-forming capacities were also determined at the indicated weeks after coculture with stromal cells (n=3) (FIG. 6B, right): miR-22F/+_Cont. vec.+Empty vec. (leftmost bar), miR-22F/+_Cont. vec.+TET2 (second bar from the left), miR-22F/+_Cre+Empty vec. (second bar from the right), miR-22F/+_Cre+TET2 (rightmost).

FIG. 6C shows that TET2 attenuates the hematopoietic malignancies induced by miR-22 overexpression. KSL cells sorted from miR-22F/+ mice were infected with Cre-GFP or GFP control vector before TET2 infection, and 1,500 GFP$^+$ KSL cells were transplanted into recipient mice with $2.0 \times 10^5$ Ly45.1 competitor bone marrow mononuclear cells (BM MNCs). Disease-free survival of recipient mice was examined by Kaplan-Meier survival curves. Log-rank test was used to generate p values.

FIG. 6D shows an overview of the experimental design for introduction of TET2 into KSL cells from miR-22 transgenic mice. KSL cells purified from miR-22 transgenic mice were subjected to infection with TET2-expressing vector, and their characteristics were evaluated in vivo and in vitro.

FIG. 6E shows the colony-forming capacity of miR-22 transgenic progenitor cells is attenuated by ectopic expression of TET2. Two weeks after pIpC administration, sorted KSL cells from miR-22F/+;Mxl-Cre mice were infected with TET2-expressing vector and resorted KSL cells were then subjected to incubation in semisolid medium. The resulting colony numbers were scored in three independent littermate pairs in the indicated platings (n=3). N.D., non-detectable. Mxl-Cre+Empty vec. (leftmost bar), Mxl-Cre+TET2 (second bar from the left), miR-22F/+Mxl-Cre+Empty vec. (second bar from the right), miR-22F/+Mxl-Cre+TET2 (rightmost).

FIG. 6F and FIG. 6G shows that ectopic expression of TET2 causes a reduction in LTC-IC capacity of miR-22 transgenic progenitor cells. TET2-infected KSL cells from miR-22F/+;Mxl-Cre mice or littermate controls, as shown in FIG. 6D, were cocultured with stromal cells for the indicated weeks. Maintained KSL cells were evaluated 2 weeks after coculture (n=3) (FIG. 6F). At the indicated times after coculture, the capacity of colony formation was also determined in semisolid medium (n=3) (FIG. 6G). miR-22F/++ Control (leftmost bar), miR-22F/++TET2 (second bar from the left), miR-22F/+;Mxl-Cre+Control (second bar from the right), miR-22F/+;Mxl-Cre+TET2 (rightmost).

FIG. 6H shows increased reconstitution capacity of KSL cells of miR-22 transgenic mice is reduced by ectopic expression of TET2. The sorted KSL cells from miR-22F/+;Mxl-Cre mice or littermate controls were infected with TET2-expressing vector. $1 \times 10^4$ KSL cells were resorted and subjected to bone marrow transplantation with $5 \times 10^5$ competitor BM MNCs. Representative flow cytometry data of the CD45.1/CD45.2 positivity at 6 weeks after transplantation are shown.

FIG. 6I show inhibition of miR-22 increases the expression of TET2 and its putative target genes in human leukemic cells. K562 cells were infected with the vector encoding miR-22 sponge or control sponge, and 48 hr after the infection, cell lysates were subjected to immunoblot analysis for the indicated proteins.

FIG. 6J shows inhibition of miR-22 suppresses the proliferation of human leukemic cells. K562 cells were infected with the vector encoding miR-22 sponge (bottom line) or control sponge (top line). Forty-eight hours after puromycin selection, $5 \times 10^4$ cells were incubated for seven days. Optical densities of the cells were determined at the indicated times (n=3).

FIGS. 7A-G show that miR-22 overexpression directly correlates with the silencing of TET2 in human MDS and AML patients.

FIG. 7A shows TET2 expression is downregulated in human MDS patients. Expression levels of TET2 protein in $CD34^{pos}$ blasts in subtypes of MDS were evaluated by immunohistochemical analysis. Representative images of immunohistochemical analysis for TET2 protein in patients with subtypes of MDS are shown (left). Insets represent TET2 staining in blasts (arrow with B) with a high magnification. Scoring the expression levels of TET2 in blasts is shown (right). The data were analyzed by Chi-square test. r, Pearson's r. Scale bars, 60 μm.

FIG. 7B shows downregulation of TET2 levels correlates with poor survival rates of human MDS patients. Overall survival of patients that express low TET2 (TET2 Score 1, n=38, bottom line) or high TET2 (TET2 Score 2 or 3, n=69, top line) is shown. p value was generated by a log-rank test.

FIG. 7C shows survival rates of low TET2 (Score 1, bottom line) and high TET2 (Score 2 or 3, top line) patients with RA (left), RAEB-1 (middle), and RAEB-2 (right). Survival rate of the p value was generated by a log-rank test.

FIG. 7D shows miR-22 overexpression correlates with downregulation of TET2 in MDS patients. One-hundred and seven MDS patient specimens were subjected to in situ hybridization and immunohistochemical analyses, and the expression levels of miR-22 and TET2 were evaluated. The data were analyzed by Chi-square test. r, Pearson's r.

FIG. 7E shows the expression levels of miR-22 and TET2 in 18 AML with MLD patient samples were evaluated. The data were analyzed by Chi-square test. r, Pearson's r. AML, acute myeloid leukemia; MLD, multiple lineage dysplasia.

FIG. 7F shows that miR-22 is highly expressed in human AML patients. Expression levels of miR-22 in $CD34^{pos}$ bone marrow cells from healthy donors (n=9) and AML patients (n=215) are shown.

FIG. 7G shows, without wishing to be bound by theory, a possible model of the oncogenic role of miR-22 in hematopoiesis. miR-22 may negatively regulate TET2 tumor suppressor, leading to a reduction of 5-hmC and a potentiation of global gene methylation. This genetic remodeling in turn enhances HSC function and promotes hematological transformation. HSCs, hematopoietic stem cells; LIC, leukemia-initiating cells.

FIGS. 8A-I show that miR-22 enhances EMT and tumor invasion and metastasis.

FIG. 8A and FIG. 8B show MCF-10A cells infected with the miR-22 expressing or empty vector were subjected to immunofluorescence (FIG. 8A) and Western blot (FIG. 8B) analyses for the indicated proteins. Scale bars, 20 μm.

FIG. 8C shows replating efficiency of mammospheres derived from MCF-10A cells expressing miR-22. The number of mammospheres per 1000-plated cells in each culture was then quantified. The data are represented as mean±SD from three independent experiments.

FIG. 8D shows H&E-stained sections of primary mammary tumors formed by MCF-7 cells expressing miR-22, at 12 weeks after orthotopic transplantation. Arrows indicate areas of lymphatic invasion. Scale bars, 50 μm.

FIG. 8E and FIG. 8F show Ki67- and MECA-32-stained sections of primary mammary tumors formed by MCF-7 cells expressing miR-22 (FIG. 8E). Arrows indicate tumor cells within a vessel. Scale bars, 50 μm. The quantification of vessel numbers (using MECA-32-stained sections) at the center and the edge of the primary mammary tumors is also shown (FIG. 8F). The data are represented as mean±SD (n=6).

FIG. 8G shows GFP images (left) and H&E staining (right) of lungs isolated from mice that received orthotopic injection of MCF-7 cells expressing miR-22, at 12 weeks after transplantation. Arrow indicates clusters of metastatic cells. Scale bars, 100 μm.

FIG. 8H and FIG. 8I show H&E-, Ki67-, ERα- and TTF1-stained sections of lungs isolated from mice that received orthotopic injection of MCF-7 cells expressing miR-22, at 12 weeks after transplantation (FIG. 8H). Scale bars, 50 μm. The number of lung micrometastases (micromets) per section in individual mice was also quantified (FIG. 8I). The data are represented as mean±SD (n=6).

FIGS. 9A-G show that miR-22 increases mammary gland side-branching and stemness in vivo in transgenic mice.

FIG. 9A shows a schematic representation of the strategy for generation of floxed miR-22 mouse embryonic stem cells. Arrows directly above the "MMTC-Cre" label indicate the positions of primers used for genotyping the miR-22 transgenic mice. The line under the label "probe" indicates the position of probe for the Southern blot analysis. The F1 floxed miR-22 founder mice were bred to MMTV-Cre strain to delete LoxP site.

FIG. 9B shows that genomic DNAs were isolated from the tails of miR-22-LoxP mice were digested by Spe I and subjected to Southern blot analysis.

FIG. 9C shows total RNAs isolated from mammary gland tissues of miR-$22^{F/+}$;MMTV-Cre mice were subjected to real-time qPCR (left) or Northern blot analysis (right) to evaluate miR-22 expression. The data are represented as mean±SD (n=4).

FIG. 9D shows whole mount analyses that were conducted on 7-weeks old miR-$22^{F/+}$;MMTV-Cre mice and MMTV-Cre littermates (left) and the number of mammary gland side-branches was quantified (right). Scale bars, 500 μm. The data are represented as mean±SD (n=3).

FIG. 9E show distribution of $CD45^{neg}CD31^{neg}CD140a^{neg}Ter119^{neg}$ mouse mammary cells according to their expression of CD24 and CD49f. Cells were analyzed on 7-weeks old miR-$22^{F/+}$;MMTV-Cre mice and littermate controls (left). Mouse mammary stem cells (MSCs) according to their expression of $CD24^{high}CD49^{high}$ in $Lineage^{negative}$ (middle) or total mammary epithelial cells (right) were quantified by a flow cytometric analysis. The data are represented as mean±SD (n=4).

FIG. 9F and FIG. 9G show schematic representations of limiting dilution transplantation experiments with $CD24^{high}CD49f^{high}$ MSCs (FIG. 9F). $3\times10^2$, $1\times10^3$ or $1.2\times10^4$ $Lin^{neg}CD24^{high}CD49^{high}$ MSCs isolated from 7-weeks old miR-$22^{F/+}$;MMTV-Cre mice and littermate controls were injected into the cleared fat-pad of 3-weeks old FVB/NJ female mice and whole mount analyses were then conducted at 6 weeks after injection (FIG. 9G). Representative images of mammary gland side-branches are shown in the left panel. The resulting data were also analyzed by Chi-square test (right).

FIG. 10A shows a cumulative disease-free survival analysis. A statistically significant decrease in lifespan for the miR-$22^{F/+}$;MMTV-Cre cohort was found compared with the MMTV-Cre cohort (p=0.0024, n=11).

FIG. 10B shows H&E-stained sections of diffuse alveolar and ductal hyperplasia isolated from 12-months old miR-$22^{F/+}$;MMTV-Cre mice. Scale bars, 200 μm.

FIG. 10C shows lysates from mammary tumors of miR-$22^{F/+}$;MMTV-Cre mice that were subjected to Western blot analysis for the indicated proteins.

FIG. 10D and FIG. 10E show H&E-stained sections of primary mammary tumors and lungs isolated from 8-months old post-pregnant miR-$22^{F/+}$;MMTV-Cre mice (FIG. 10D). Arrows indicate clusters of metastatic cells in the lung. Scale bars, 200 μm. H&E- and Ki67-stained sections of lungs isolated from miR-$22^{F/+}$;MMTV-Cre mice are also shown (FIG. 10E). Scale bars, 200 μm.

FIG. 10F shows the quantification of incidence of metastases to the lung in MMTV-neu;miR-$22^{F/+}$;MMTV-Cre (represented as miR-$22^{F/+}$;MMTV-neu) and MMTV-neu littermates (8-16 months old).

FIG. 10G shows lysates from mammary tumors of miR-$22^{F/+}$;MMTV-neu that were subjected to Western blot analysis for the indicated proteins.

FIG. 10H and FIG. 10I show H&E-stained sections of the lungs isolated from miR-$22^{F/+}$;MMTV-neu mice and littermate controls (FIG. 10H). Arrows indicate clusters of metastatic cells in the lung. Scale bars, 200 μm. H&E-, Ki67- and ErbB2-stained sections of lungs isolated from miR-$22^{F/+}$;MMTV-neu mice are also shown (FIG. 10I). Scale bars, 200 μm.

FIGS. 11A-L show that miR-22 regulates epigenetic inactivation of miR-200 and directly targets TET methylcytosine dioxygenases.

FIG. 11A and FIG. 11B show real-time qPCR analysis of Zeb1/Zeb2 (FIG. 11A) or miR-200a/miR-200c (FIG. 11B) with RNAs from MCF-10A cells infected with the miR-22 expressing or empty vector. The data are represented as mean±SD from three independent experiments.

FIG. 11C shows real-time qPCR analysis of miR-200a/miR-200c with RNAs obtained from miR-22$^{F/+}$;MMTV-Cre mice and littermate controls. The data are represented as mean±SD (n=3).

FIG. 11D shows methylation-specific PCR analysis of mir-200c CpG islands with genomic DNAs purified from the indicated cells infected with the miR-22 expressing vector.

FIG. 11E shows restored miR-200c expression upon treatment with DNA demethylating agent 5'-aza-2'-deoxycytidine (5'-Aza) in MCF-10A cells infected with the miR-22 expressing vector. The data are represented as mean±SD (n=3).

FIG. 11F shows glucMS-qPCR analysis of CpG islands within the mir-200c promoter regions specifically enriched for 5-hydroxymethylcytosine (5hmC) in MCF-10A cells infected with the miR-22 expressing vector. The data are represented as mean±SD (n=3).

FIG. 11G shows representative seed sequences for miR-22 on the TET family: 7 base pairs (red-colored) and 8 base pairs (blue-colored) on human and mouse TET family (top) and seed match sequences of miR-22 within 3'UTR of human and mouse TET2b as an example (bottom) are shown.

FIG. 11H shows total RNAs isolated from primary mammary epithelial cells of miR-22$^{F/+}$;MMTV-Cre mice or littermate controls that were subjected to real-time qPCR for Tet1, Tet2 and Tet3 mRNA. The data are represented as mean±SD (n=3).

FIG. 11I shows total RNAs isolated from MCF-10A cells transfected with the inhibitor (decoy) of miR-22 that were subjected to real-time qPCR for TET1, TET2 and TET3 mRNA. The data are represented as mean±SD (n=3).

FIG. 11J shows a luciferase assay of the luciferase gene linked to the 3'UTR of TET2. HEK293 cells were transiently transfected with a combination of pGL3 firefly luciferase reporter plasmids encoding wild-type (left) or mutated (right) 3'UTR sequences of human TET2b, miR-22 and a *Renilla* luciferase reporter for normalization. The data are represented as mean±SD (n=3).

FIG. 11K shows genomic DNA purified from HEK293 cells expressing control miRNA, miR-22 or TET2 siRNA that was denatured and neutralized. Global 5hmC levels were then measured by using a dot blot assay with anti-5hmC antibody and normalized by methylene blue staining (left). The resulting 5hmC levels were also quantified (right). The data are represented as mean±SD (n=3).

FIG. 11L shows 5hmC- and DAPI-stained sections of the duct of mammary glands isolated from 7-weeks old miR-22$^{F/+}$;MMTV-Cre mice or littermate controls. Scale bar, 100 μm. The arrows indicate the cells with strong 5hmC positive signals.

FIGS. 12A-M show that loss of miR-22 or TET family members alters EMT, stemness and miR-200 levels FIG. 12A shows Cell lysates from LM2 cells infected with the control or miR-22 sponge that were subjected to Western blot analysis for the indicated proteins. PTEN protein was used as a verified miR-22 target to show the efficacy of the miR-22 sponge in this analysis.

FIG. 12B shows LM2 cells infected with the miR-22 sponge that were subjected to the cell migration (top) and invasion assay (bottom). Representative fields of the cells are shown (left). Scale bars, 100 μm. The migrated or invaded cells were also quantified (right). The data are represented as mean±SD from three independent experiments.

FIG. 12C shows real-time qPCR analysis of miR-200a/miR-200c with RNAs from LM2 cells infected with the miR-22 sponge. The data are represented as mean±SD (n=3).

FIG. 12D and FIG. 12E show H&E-stained sections of primary mammary tumors (left), or H&E-stained and Ki67-stained sections of lungs isolated from mice that received orthotopic injection of control- or miR-22 sponge-infected LM2 cells (right) (FIG. 12D). Scale bars, 100 μm. The incidence of metastases to the lung in mice at 10 weeks after orthotopic injection is also shown (FIG. 12E).

FIG. 12F and FIG. 12J show MCF-10A cells infected with the lentiviral vector expressing TET2 (FIG. 12F) or TET3 (FIG. 12J) shRNA that were subjected to the cell migration assay and the migrated cells were then quantified. The data are represented as mean±SD (n=3).

FIG. 12G and FIG. 12K show cell lysates from MCF-10A cells expressing TET2 (FIG. 12G) or TET3 (FIG. 12K) shRNA that were subjected to Western blot analysis for the indicated proteins.

FIG. 12H and FIG. 12L show real-time qPCR analysis of miR-200c with RNAs from MCF-10A cells expressing TET2 (H) or TET3 (L) shRNA. The data are represented as mean±SD (n=3).

FIG. 12I and FIG. 12M show GlucMS-qPCR analysis of CpG islands within the mir-200c promoter regions specifically enriched for 5hmC in MCF-10A cells expressing TET2 (I) or TET3 (M) shRNA. The data are represented as mean±SD (n=3).

FIG. 13A and FIG. 13F show MCF-10A cells infected with a combination of the miR-22, TET2b (FIG. 13A) and TET3 (FIG. 13F) expressing vector that were subjected to a cell migration assay. Representative fields of the migrated cells are shown (left). Scale bars, 100 μm. The migrated cells were also quantified (right). The data are represented as mean±SD from three independent experiments.

FIG. 13B and FIG. 13G show cell lysates from MCF-10A cells expressing a combination of the miR-22, TET2b (FIG. 13B) and TET3 (FIG. 13G) that were subjected to Western blot analysis for the indicated proteins. Asterisk indicates non-specific band.

FIG. 13C and FIG. 13H show mammospheres derived from MCF-10A cells expressing a combination of the miR-22, TET2b (FIG. 13C) and TET3 (FIG. 13H) that were measured. The number of mammospheres per 1000-plated cells in each culture was then quantified. The data are represented as mean±SD (n=3).

FIG. 13D and FIG. 13I show genomic DNA purified from MCF-10A cells expressing a combination of the miR-22, TET2b (FIG. 13D) and TET3 (FIG. 13I) that was denatured and neutralized. Global 5hmC levels were then measured by a dot blot assay using anti-5hmC antibody.

FIG. 13E and FIG. 13J show real-time qPCR analysis of miR-200c with RNAs from MCF-10A cells expressing a combination of the miR-22, TET2b (FIG. 13E) and TET3 (FIG. 13J). The data are represented as mean±SD (n=3).

FIG. 13K and FIG. 13L show LM2 cells infected with a combination of the control and miR-22 sponge and the TET2 or TET3 shRNA expressing vector that were subjected to Western blot analysis for the indicated proteins (FIG. 13K) and the cell invasion assay (FIG. 13L). Asterisk indicates non-specific band. The data are represented as mean±SD (n=3).

FIG. 14A shows miR-22 expression profiling that was analyzed from a previously published Illumina Human RefSeq-8 and miRNAv1 array dataset (superSeries GSE22220). Breast tumors were classified by molecular subtypes, estrogen receptor (ER), progesterone receptor (PR), ERBB2 (HER-2) and epithelial clusters.

FIG. 14B shows miR-22 expression that was analyzed by using a real-time qPCR with RNAs from human breast cancer patient samples. Tumor grade was determined by the parameters, ER, PR, ERBB2 (HER-2) and epithelial clusters. HG, ER-positive high-grade tumors; LG, ER-positive low-grade tumors.

FIG. 14C shows non triple-negative breast cancer (TNBC) patient samples that were sub-divided into two groups according to low and high expression of miR-22 with median split of all samples. A Kaplan-Meier plot representing the disease-free survival of patients was stratified.

FIG. 14D shows an anti-correlation between miR-22 and TET family expressions that was analyzed using a real-time qPCR with RNAs from breast cancer patient samples.

FIG. 14E shows co-expression analysis of TET family and miR-200a/miR-200c that was analyzed by using a real-time qPCR with RNAs from breast cancer patient samples.

FIG. 14F shows, without wishing to be bound by theory, a proposed model of the role of miR-22 for EMT, stemness and metastasis through epigenetic inactivation of miR-200 by directly targeting the TET family. miR-22 decreases the level of 5hmC by negatively regulating TET family, followed by epigenetic inactivation of miR-200 due to the reduced 5hmC levels. Ultimately, dysfunction of miR-200 triggers EMT and stemness, which in turn increases mammary tumorigenesis and metastasis.

DETAILED DESCRIPTION OF THE INVENTION

Figure 1A:
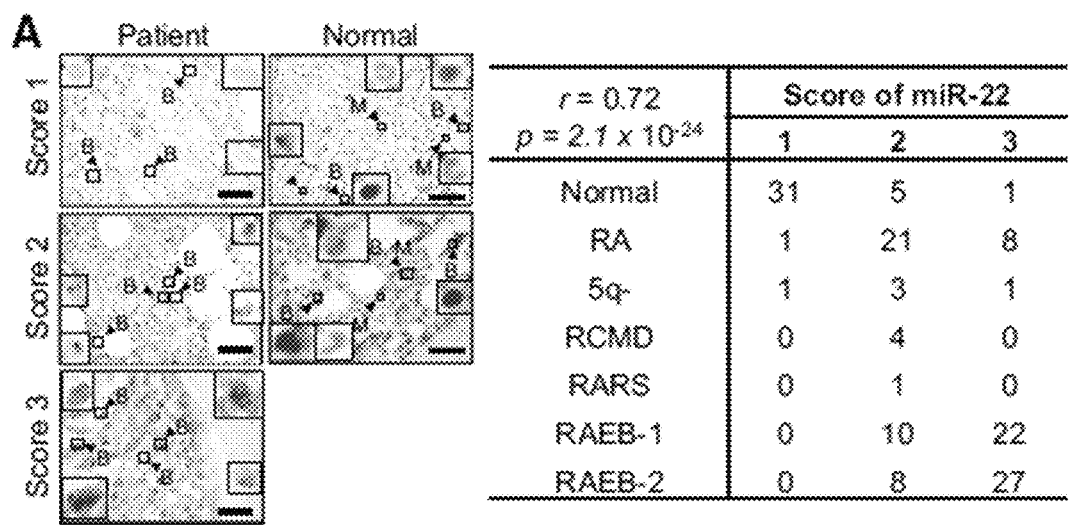
FIGS. 1A-G show that miR-22 is upregulated in MDS patients and leads to increased replating capacity in vitro. All error bars represent ±SD.

The present invention is based, in part, on the discovery that miRNAs, including miR-22, can regulate targets, including TET2, that are linked to a variety of cancers, including blood-based cancers and breast cancers. The present invention includes targeting miRNAs, including miR-22, with various inhibitors for the treatment and/or prevention of a variety of cancers, including blood-based cancers and breast cancers. For instance, such inhibition could be mediated by sequence specific chemically modified oligonucleotides. An exemplary modification is a locked nucleic acid (LNA) in which the nucleic acid's ribose moiety is modified with an extra bridge connecting the 2' oxygen and 4' carbon, which locks the ribose in the 3'-endo conformation. These LNA inhibitors, among others, when directed at the tumor suppressor gene-regulating miRNAs disclosed herein, provide for cost effective anti-cancer agents that can be delivered efficiently and possess sufficient bioavailability for the treatment and prevention of various cancers.

In one aspect, the present invention provides a method of treating or preventing a cancer, including blood-based cancers and breast cancers, in a subject in need thereof, comprising administering to the subject an inhibitor of miR-22, including, for example, an antisense oligonucleotide directed to miR-22. In another aspect, the present invention provides a pharmaceutical composition for the treatment of a cancer, including blood-based cancers and breast cancers, comprising an inhibitor of miR-22, including, for example, an antisense oligonucleotide directed to miR-22. In another aspect, the present invention provides an anti-cancer, including blood-based cancers and breast cancers, agent comprising an inhibitor of miR-22, including, for example, an antisense oligonucleotide directed to miR-22. In yet another aspect, the present invention provides a use of an inhibitor of miR-22, including, for example, an antisense oligonucleotide directed to miR-22, in the manufacture of a medicament for the treatment of a cancer, including blood-based cancers and breast cancers.

In some embodiments, the present methods provide an inhibitor that comprises an antisense oligonucleotide.

In some embodiments, the expression and/or activity of miR-22 is reduced in the subject following administration of the inhibitor. In various embodiments, the inhibitor comprises is an antisense oligonucleotide comprising a sequence that is at least partially complementary to a mature sequence of miR-22.

In various embodiments, the inhibitor, including for example an inhibitor that comprises an antisense oligonucleotide, which optionally comprises a sequence that is at least partially complementary to a mature sequence of miR-22, comprises one or more nucleotides that are chemically modified, including, for example, a chemical modification is selected from locked nucleic acid (LNA), phosphorothioate, 2'-O-Methyl, or 2'-O-Methoxyethyl. In some embodiments, the chemical modification is one or more of a 2'-O-alkyl-RNA unit, 2'-OMe-RNA unit, 2'-amino-DNA unit, 2'-fluoro-DNA unit (including, but not limited to, a DNA analogue with a substitution to a fluorine at the 2' position (2' F)), LNA unit, PNA unit, HNA unit, INA unit, and a 2' MOE RNA unit.

In various embodiments, the inhibitor, including for example an inhibitor that comprises an antisense oligonucleotide, which optionally comprises a sequence that is at least partially complementary to a mature sequence of miR-22, comprises 16 or fewer nucleotides or is about 7 to about 8 nucleotides.

In various embodiments, the inhibitor of miR-22 prevents the deregulation of ten-eleven-translocation gene 2 (TET2). In some embodiments, the expression and/or activity of TET2 is not reduced in the subject following administration of the inhibitor. In some embodiments, the expression and/or activity of TET2 is increased in the subject following administration of the inhibitor.

In various embodiments, the present methods are useful in the treatment or prevention of cancers, including blood-based cancers and breast cancers. In some embodiments, the blood-based cancer is, for example, a leukemia, lymphoma, myeloma or myelodysplastic/myeloproliferative neoplasm (MDS/MPN). In some embodiments, the leukemia is acute lymphocytic leukemia (ALL), acute myelogenous leukemia (AML), chronic lymphocytic leukemia (CLL), or chronic myelogenous leukemia (CML). In some embodiments, the lymphoma is a Hodgkin lymphoma or a non-Hodgkin lymphoma. In some embodiments, the myeloma is IgG, IgE, IgA, IgM, IgD, light chain, or non-secretory myeloma. In some embodiments, the myeloma is multiple myeloma. In various embodiments, the breast cancer is one or more of ER+, PR+, HER2+, AR+, and PRLr+. In various embodiments, the breast cancer is one or more of ER−, PR−, HER2−, AR−, and PRLr−.

In various embodiments, the subject is a mammal, including, for example, a human.

In some aspects, the present invention provides a method of treating or preventing leukemia or breast cancer in a subject in need thereof, comprising administering an effective amount of an antisense oligonucleotide directed to miR-22. In another aspect, the present invention provides a pharmaceutical composition for the treatment of leukemia or breast cancer comprising an antisense oligonucleotide directed to miR-22. In another aspect, the present invention provides an anti-leukemia agent comprising an antisense oligonucleotide directed to miR-22. In yet another aspect, the present invention provides a use of an antisense oligonucleotide directed to miR-22, in the manufacture of a medicament for the treatment of leukemia or breast cancer.

In other aspects, the present invention provides a method of preventing metastasis in a subject in need thereof, comprising administering an effective amount of an inhibitor of miR-22, including, for example, an antisense oligonucleotide directed to miR-22. In another aspect, the present invention provides a pharmaceutical composition for the prevention of metastasis comprising an inhibitor of miR-22, including, for example, an antisense oligonucleotide directed to miR-22. In another aspect, the present invention provides a prevention of metastasis agent comprising an inhibitor of miR-22, including, for example, an antisense oligonucleotide directed to miR-22. In yet another aspect, the present invention provides a use of an inhibitor of miR-22, including, for example, an antisense oligonucleotide directed to miR-22, in the manufacture of a medicament for the prevention of metastasis.

In other aspects, the present invention provides a method of preventing a decrease or causing an increase in TET2 expression and/or activity in a subject in need thereof, comprising administering an effective amount of an inhibitor of miR-22, including, for example, an antisense oligonucleotide directed to miR-22. In another aspect, the present invention provides a pharmaceutical composition for the prevention of a decrease or an increase in TET2 expression and/or activity comprising an inhibitor of miR-22, including, for example, an antisense oligonucleotide directed to miR-22. In another aspect, the present invention provides an prevention of a decrease or an increase in TET2 expression and/or activity agent comprising an inhibitor of miR-22, including, for example, an antisense oligonucleotide directed to miR-22. In yet another aspect, the present invention provides a use of an inhibitor of miR-22, including, for example, an antisense oligonucleotide directed to miR-22, in the manufacture of a medicament for the prevention of a decrease or an increase in TET2 expression and/or activity.

In some embodiments, the anti-metastatic and/or TET-regulating agent is an antisense oligonucleotide comprising a sequence that is at least partially complementary to a mature sequence of miR-22. In various embodiments, the anti-metastatic and/or TET-regulating agent, including for example an inhibitor that comprises an antisense oligonucleotide, which optionally comprises a sequence that is at least partially complementary to a mature sequence of miR-22, comprises one or more nucleotides that are chemically modified, including, for example, a chemical modification is selected from locked nucleic acid (LNA), phosphorothioate, 2'-O-Methyl, or 2'-O-Methoxyethyl. In some embodiments, the chemical modification is one or more of a 2'-O-alkyl-RNA unit, 2'-OMe-RNA unit, 2'-amino-DNA unit, 2'-fluoro-DNA unit (including, but not limited to, a DNA analogue with a substitution to a fluorine at the 2' position (2' F)), LNA unit, PNA unit, HNA unit, INA unit, and a 2' MOE RNA unit. In various embodiments, the inhibitor, including for example an inhibitor that comprises an antisense oligonucleotide, which optionally comprises a sequence that is at least partially complementary to a mature sequence of miR-22, comprises 16 or fewer nucleotides or is about 7 to about 8 nucleotides.

In some embodiments, the present invention treats or prevents cancers (by way of non-limiting example, blood-based cancers and breast cancers) in a subject through the inhibition of an miRNA. MiRNAs are short nucleic acid molecules that are able to regulate the expression of target genes. See review by Carrington et al. *Science*, Vol. 301 (5631):336-338, 2003. MiRNAs are often between about 18 to 24 nucleotides in length. MiRNAs act as repressors of target mRNAs by promoting their degradation, when their sequences are perfectly complementary, and/or by inhibiting translation, when their sequences contain mismatches.

Without being bound by theory, mature miRNAs are believed to be generated by pol II or pol III and arise from initial transcripts termed pri-miRNAs. These pri-miRNAs are frequently several thousand bases long and are therefore processed to make much shorter mature miRNAs. These pri-miRNAs may be multicistronic and result from the transcription of several clustered sequences that organize what may develop into many miRNAs. The processing to yield miRNAs may be two-steps. First, pri-miRNAs may be processed in the nucleus by the RNase Drosha into about 70- to about 100-nucleotide hairpin-shaped precursors (pre-miRNAs). Second, after transposition to the cytoplasm, the hairpin pre-miRNAs may be further processed by the RNase Dicer to produce a double-stranded miRNA. The mature miRNA strand may then be incorporated into the RNA-induced silencing complex (RISC), where it may associate with its target mRNAs by base-pair complementarity and lead to suppression of protein expression. The other strand of the miRNA duplex that is not preferentially selected for entry into a RISC silencing complex is known as the passenger strand or minor miRNA or star (*) strand. This strand may be degraded. It is understood that, unless specified, as used herein an miRNA may refer to pri- and/or pre- and/or mature and/or minor (star) strand and/or duplex version of miRNA.

In some embodiments, miRNA genes may be located within introns of protein-coding genes or within introns or exons of noncoding transcriptional units. The expression of intronic miRNAs may coincide with that of the hosting transcriptional units because they are typically oriented in the same direction and are coordinately expressed with the pre-mRNAs in which they reside.

In some embodiments, miRNAs may bind to sequences within the 3' untranslated region (3'UTR) of target gene transcripts. In some embodiments, miRNAs may bind to sequences outside of the 3'UTR of target gene transcripts. In some embodiments, miRNAs may bind to both within and outside the 3'UTR of target gene transcripts.

In some embodiments, nucleotide pairing between the second and seventh nucleotides of the miRNA (the miRNA seed sequence) and the corresponding sequence along the target 3'UTR (seed match) may occur for target recognition. Accordingly, the binding between miRNA and target may comprise about a 5 nucleotide base pairing. Additionally, the binding between miRNA and target may comprise more than a 5 nucleotide base pairing.

In some embodiments, the binding between an miRNA and the gene that it regulates may be mediated by the miRNA binding up to 2, up to 4, up to 6, up to 8, or up to 10 sites of the target nucleic acid.

MiRNAs of the present invention may regulate nucleic acids, including but not limited to cancer-critical genes such as genes of a marker linked to a cancer etiology, by direct binding. This binding may be perfectly complementary to the target nucleic acid or contain mismatches. The effect of this binding may be to promote degradation and/or to inhibit translation of the target.

In some embodiments, the present invention treats or prevents cancer in a subject through the inhibition of miR-NAs, such as miR-22. Mir-22 has the following sequence: AAGCUGCCAGUUGAAGAACUGU (SEQ ID NO: 1).

The predicted miR-22 hairpin precursor is contained entirely within exon 2 of a noncoding transcript, C17orf91, and the splicing pattern is generally conserved in human and mouse, despite the lack of protein-coding potential. See Rodriguez et al., Identification of mammalian microRNA host genes and transcription units. Genome Res. 2004 October; 14(10A):1902-10. Deletion of exon 2 of C17orf91 encompassing mir-22 in mouse models has revealed that miR-22 may play a role in cardiac hypertrophy and remodeling by targeting SIRT1 (NAD-dependent deacetylase sirtuin-1), HDAC4 (histone deacetylase 4), PURB (purine-rich element binding protein B) and PTEN. See Gurha et al. Targeted deletion of microRNA-22 promotes stress-induced cardiac dilation and contractile dysfunction. Circulation. 2012 Jun. 5; 125(22):2751-61; Huang et al. MicroRNA-22 regulates cardiac hypertrophy and remodeling in response to stress. Circ Res. 2013 Apr. 26; 112(9):1234-43.

It has been demonstrated that miR-22 acts as a proto-oncogenic miRNA in prostate cancer through the targeting of the PTEN 3'UTR. See Poliseno et al. Identification of the miR-106b~25 microRNA cluster as a proto-oncogenic PTEN-targeting intron that cooperates with its host gene MCM7 in transformation. Sci Signal. 2010; 3(117):ra29; International Patent Publication No. WO 2012/142313, the contents of which are hereby incorporated by reference in their entireties. Further, increased miR-22 expression is observed in primary prostate cancer cell lines and cell lines from distant prostate carcinoma metastases compared to normal epithelium, as well as in prostate tumor samples relative to normal prostatic epithelium. See Liu et al. miR-22 functions as a micro-oncogene in transformed human bronchial epithelial cells induced by anti-benzo[a]pyrene-7,8-diol-9,10-epoxide. Toxicol In Vitro. 2010 June; 24(4):1168-75; Bar et al. miR-22 forms a regulatory loop in PTEN/AKT pathway and modulates signaling kinetics. PLoS One. 2010; 5(5):e10859.

Additionally, it has been observed that AKT, a downstream target of PTEN, activated mir-22 transcription, suggesting a regulatory loop in the oncogenic PI3K/AKT signaling pathway. See Bar et al. miR-22 forms a regulatory loop in PTEN/AKT pathway and modulates signaling kinetics. PLoS One. 2010; 5(5):e10859.

Further, miR-22 triggers epithelial-mesenchymal transition (EMT), enhances stemness and promotes metastasis in vivo. See Song et al. MicroRNA-Antagonism Regulates Breast Cancer Stemness and Metastasis via TET-Family-Dependent Chromatin Remodeling. Cell. 2013 Jul. 18; 154 (2):311-24. In a mammary gland-specific transgenic mouse model, miR-22 enhanced mammary gland side branching, expanded mammary stem cell compartments and promoted breast cancer development. In keeping with these findings, it was also reported that miR-22 was highly expressed in mouse mammary epithelial progenitors. Ibarra et al. A role for microRNAs in maintenance of mouse mammary epithelial progenitor cells. Genes Dev. 2007 Dec. 15; 21(24):3238-43.

Moreover, miR-22 promoted aggressive metastatic disease in neu (ErbB2; Her2) or PyVT oncogene compound mice.

The present invention, in some embodiments, shows that miR-22 may function as an epigenetic modifier and EMT promoter independently of its ability to target Pten. In some embodiments, miR-22 exerts its metastatic potential by silencing the anti-metastatic miR-200 family. In some embodiments, miR-22 exerts its metastatic potential by direct targeting of the methylcytosine dioxygenase TET family members. In some embodiments, miR-22's silencing of the anti-metastatic miR-200 family is via direct targeting of the methylcytosine dioxygenase TET. In some embodiments, miR-22 inhibits the demethylation of the mir-200 promoter. In another embodiment, miR-22 reduces the levels of global 5-hydroxymethylcytosine (5-hmC) in a subject.

In some embodiments, the present invention includes treatment or prevention of cancer in a subject through the prevention of a decrease and/or causing of an increase in TET family member expression and/or activity. In some embodiments, the present invention includes treatment or prevention of cancer in a subject through the prevention of a decrease and/or causing of an increase in TET2 expression and/or activity. TET family members specifically modify DNA by hydroxylating 5-methylcytosine (5mC) and, without wishing to be bound by theory, this may explain how cells can erase existing methylation marks. Within the TET family of proteins, TET1, TET2, and TET3 have been shown to convert 5mC to 5-hydroxymethylcytosine (5hmC). The level of 5hmC is associated with TET gene expression and is found increased in differentiated cells. The level of 5hmC is reduced in many types of tumors, identifying 5hmC as a biomarker associated with tumor development.

In some embodiments, the present invention includes treatment or prevention of cancer in a subject through the prevention of silencing of the anti-metastatic miR-200 family of miRNAs. Mir-200 family members are short RNA molecules that regulate the expression levels of other genes by binding and cleaving mRNAs or inhibiting translation. The miR-200 family contains miR-200a, miR-200b, miR-200c, miR-141, and miR-429.

In some embodiments, the sequence of the inhibitor is taken, in part, from the sequence of a human transcript. In some embodiments, the inhibitor is selected to reduce the expression and/or activity of the target miRNA, by way of non-limiting example, miR-22, in a subject.

In some embodiments, an inhibitor of miRNA is an antisense oligonucleotide. Antisense oligonucleotides can include ribonucleotides or deoxyribonucleotides or a combination thereof. Antisense oligonucleotides may have at least one chemical modification (non-limiting examples are sugar or backbone modifications).

In some embodiments, the chemical modification is one or more of a phosphorothioate, 2'-O-Methyl, or 2'-O-Methoxyethyl, 2'-O-alkyl-RNA unit, 2'-OMe-RNA unit, 2'-amino-DNA unit, 2'-fluoro-DNA unit (including, but not limited to, a DNA analogue with a substitution to a fluorine at the 2' position (2' F)), LNA unit, PNA unit, HNA unit, INA unit, and a 2' MOE RNA unit.

Suitable antisense oligonucleotides can be comprised of one or more conformationally constrained or bicyclic sugar nucleoside modifications (BSN) that confer enhanced thermal stability to complexes formed between the oligonucleotide containing BSN and their complementary miRNA target strand. For example, in one embodiment, the antisense oligonucleotides contain at least one locked nucleic acid. Locked nucleic acids (LNAs) contain a 2'-O, 4'-C-methylene ribonucleoside (structure A) wherein the ribose sugar moiety is in a locked conformation. In another embodiment, the antisense oligonucleotides contain at least one 2', 4'-C-bridged 2' deoxyribonucleoside (CDNA, structure B). See, e.g., U.S. Pat. No. 6,403,566 and Wang et al. (1999) *Bioorganic and Medicinal Chemistry Letters*, Vol. 9: 1147-1150, both of which are herein incorporated by reference in their entireties. In yet another embodiment, the antisense oligonucleotides contain at least one modified nucleoside having the structure shown in structure C. The antisense oligonucleotides targeting miRNAs that regulate tumor suppressors can contain combinations of BSN (LNA, CDNA, and the like) or other modified nucleotides, and ribonucleotides or deoxyribonucleotides.

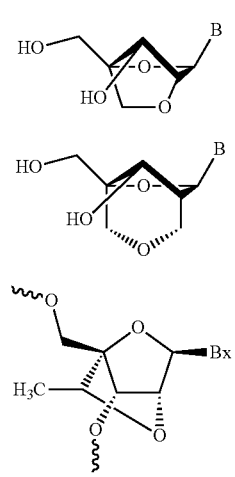

Alternatively, the antisense oligonucleotides can comprise peptide nucleic acids (PNAs), which contain a peptide-based backbone rather than a sugar-phosphate backbone. Other modified sugar or phosphodiester modifications to the antisense oligonucleotide are also contemplated. By way of non-limiting examples, other chemical modifications can include 2'-O-alkyl (e.g., 2'-O-methyl, 2'-O-methoxyethyl), 2'-fluoro, and 4'-thio modifications, and backbone modifications, such as one or more phosphorothioate, morpholino, or phosphonocarboxylate linkages (see, e.g., U.S. Pat. Nos. 6,693,187 and 7,067,641, which are herein incorporated by reference in their entireties). In one embodiment, antisense oligonucleotides targeting oncogenic miRNAs contain 2'-O-methyl sugar modifications on each base and are linked by phosphorothioate linkages. Antisense oligonucleotides, particularly those of shorter lengths (e.g., less than 16 nucleotides, 7-8 nucleotides) can comprise one or more affinity enhancing modifications, such as, but not limited to, LNAs, bicyclic nucleosides, phosphonoformates, 2' O-alkyl modifications, and the like. In some embodiments, suitable antisense oligonucleotides are 2'-O-methoxyethyl gapmers which contain 2'-O-methoxyethyl-modified ribonucleotides on both 5' and 3' ends with at least ten deoxyribonucleotides in the center. These gapmers are capable of triggering RNase H-dependent degradation mechanisms of RNA targets. Other modifications of antisense oligonucleotides to enhance stability and improve efficacy, such as those described in U.S. Pat. No. 6,838,283, which is herein incorporated by reference in its entirety, are known in the art and are suitable for use in the methods of the invention. For instance, and not intending to be limiting, to facilitate in vivo delivery and stability, the antisense oligonucleotide can be linked to a steroid, such as cholesterol moiety, a vitamin, a fatty acid, a carbohydrate or glycoside, a peptide, or other small molecule ligand at its 3' end.

In some embodiments, antisense oligonucleotides useful for inhibiting the activity of miRNAs, including, for example, miR-22, are about 5 to about 25 nucleotides in length, about 10 to about 30 nucleotides in length, or about 20 to about 25 nucleotides in length. In certain embodiments, antisense oligonucleotides targeting oncogenic miRNAs are about 8 to about 18 nucleotides in length, in other embodiments about 12 to about 16 nucleotides in length, and in other embodiments about 7 to about 8 nucleotides in length. Any 7-mer or longer complementary to an oncogenic miRNA may be used, i.e., any anti-miR complementary to the 5' end of the miRNA and progressing across the full complementary sequence of the miRNA. By way of non-limiting example, the antisense oligonucleotides targeting oncogenic miRNAs, including, for example, miR-22, are about 5, or about 6, or about 7, or about 8, or about 9, or about 10, or about 11, or about 12, or about 13, or about 14, or about 15, or about 16, or about 17, or about 18, or about 19, or about 20, or about 21, or about 22, or about 23, or about 24, or about 25, or about 26, or about 27, or about 28, or about 29, or about 30 nucleotides in length.

Antisense oligonucleotides can comprise a sequence that is at least partially complementary to a mature or minor (i.e. star) oncogenic miRNA sequence, e.g., at least about 75%, 80%, 85%, 90%, 95%, 96%, 97%, 98%, or 99% complementary to a mature or minor (i.e. star) oncogenic miRNA sequence. In some embodiments, the antisense oligonucleotide can be substantially complementary to a mature or minor oncogenic miRNA sequence, that is at least about 90%, 95%, 96%, 97%, 98%, or 99% complementary to a target polynucleotide sequence. In one embodiment, the antisense oligonucleotide comprises a sequence that is 100% complementary to a mature or minor oncogenic miRNA sequence.

As used herein, substantially complementary refers to a sequence that is at least about 95%, 96%, 97%, 98%, 99%, or 100% complementary to a target polynucleotide sequence (non-limiting examples are mature, minor, precursor miRNA, or pri-miRNA sequence of, for example, miR-22).

In some embodiments, the antisense oligonucleotides are antagomirs. Antagomirs are single-stranded, chemically-modified ribonucleotides that are at least partially complementary to miRNAs and therefore may silence them. See, e.g., Kriitzfeldt, et al. *Nature* (2005) 438 (7068): 685-9. Antagomirs may comprise one or more modified nucleotides, such as 2'-O-methyl-sugar modifications. In some embodiments, antagomirs comprise only modified nucleotides. Antagomirs can also comprise one or more phosphorothioate linkages resulting in a partial or full phosphorothioate backbone. To facilitate in vivo delivery and stability, the antagomir can be linked to a cholesterol or other moiety at its 3' end. Antagomirs suitable for inhibiting can be about 15 to about 50 nucleotides in length, about 18 to about 30 nucleotides in length, and about 20 to about 25 nucleotides in length. The antagomirs can be at least about 75%, 80%, 85%, 90%, 95%, 96%, 97%, 98%, or 99% complementary to a mature or minor oncogenic miRNA sequence. In some embodiments, the antagomir may be substantially complementary to a mature or minor oncogenic miRNA sequence, that is at least about 95%, 96%, 97%, 98%, or 99% complementary to a target polynucleotide sequence. In other embodiments, the antagomirs are 100% complementary to a mature or minor oncogenic miRNA sequence.

Antisense oligonucleotides or antagomirs may comprise a sequence that is substantially complementary to a precursor miRNA sequence (pre-miRNA) or primary miRNA sequence (pri-miRNA) of an oncogenic miRNA. In some embodiments, the antisense oligonucleotide comprises a sequence that is located outside the 3'-untranslated region of a target of that miRNA. In some embodiments, the antisense oligonucleotide comprises a sequence that is located inside the 3'-untranslated region of a target of that miRNA.

Any of the inhibitors or agonists of the oncogenic miRNAs described herein, including but not limited to miR-22, can be delivered to a target cell (a non-limiting example is a cancer cell) by delivering to the cell an expression vector encoding the miRNA inhibitors or agonists. A vector is a composition of matter which can be used to deliver a nucleic acid of interest to the interior of a cell. Numerous vectors are known in the art, including, but not limited to, linear polynucleotides, polynucleotides associated with ionic or amphiphilic compounds, plasmids, and viruses. Thus, the term vector includes an autonomously replicating plasmid or a virus. Examples of viral vectors include, but are not limited to, adenoviral vectors, adeno-associated virus vectors, retroviral vectors, and the like. An expression construct can be replicated in a living cell, or it can be made synthetically. For purposes of this application, the terms expression construct, expression vector, and vector are used interchangeably to demonstrate the application of the invention in a general, illustrative sense, and are not intended to limit the invention.

In one embodiment, an expression vector for expressing an inhibitor of an oncogenic miRNA, e.g. miR-22, comprises a promoter operably linked to a polynucleotide encoding an antisense oligonucleotide. The sequence of the expressed antisense oligonucleotide may be partially or perfectly complementary to a mature or minor sequence of an oncogenic miRNA. The phrase operably linked or under transcriptional control as used herein means that the promoter is in the correct location and orientation in relation to a polynucleotide to control the initiation of transcription by RNA polymerase and expression of the polynucleotide.

As used herein, a promoter refers to a DNA sequence recognized by the synthetic machinery of the cell, or introduced synthetic machinery, required to initiate the specific transcription of a gene. Suitable promoters include, but are not limited to, RNA pol I, pol II, pol III, and viral promoters (e.g., human cytomegalovirus (CMV) immediate early gene promoter, the SV40 early promoter, and the Rous sarcoma virus long terminal repeat).

In certain embodiments, the promoter operably linked to a polynucleotide encoding an miRNA inhibitor or a polynucleotide encoding a tumor-suppressor regulating miRNA and/or miRNA targeting genes of markers linked to cancer etiologies can be an inducible promoter. Inducible promoters are known in the art and include, but are not limited to, the tetracycline promoter, the metallothionein IIA promoter, the heat shock promoter, the steroid/thyroid hormone/retinoic acid response elements, the adenovirus late promoter, and the inducible mouse mammary tumor virus LTR.

Methods of delivering expression constructs and nucleic acids to cells are known in the art and can include, by way of non-limiting example, calcium phosphate co-precipitation, electroporation, microinjection, DEAE-dextran, lipofection, transfection employing polyamine transfection reagents, cell sonication, gene bombardment using high velocity microprojectiles, and receptor-mediated transfection.

The present invention also includes scavenging or clearing inhibitors of oncogenic miRNAs following treatment. Scavengers may include isolated nucleic acids that are complementary to miRNA inhibitors or vectors expressing the same. Therefore, they may bind to miRNA inhibitors or vectors expressing the same and, in doing so, prevent the binding between miRNA and target. The method may comprise overexpressing binding sites for the tumor suppressive inhibitors in a tissue.

In various embodiments, the present invention provides a method of treating or preventing a cancer in a subject. In various embodiments, the present invention provides a method of treating or preventing cancer, including a blood-based cancer or a breast cancer, in a subject. In various embodiments, the present invention provides a method of treating or preventing metastasis.

Cancer is a group of diseases characterized by uncontrolled cell division which can lead to abnormal tissue and, in turn, disruption of normal physiologic processes and, possibly, death. Cancer cells may be able to grow in the absence of the growth promoting factors required for the proliferation of normal cells. Further, cancer cells may be resistant to normal signals that control apoptosis.

Cancer cells may form a tumor. Cancer cells may also be blood-based. Tumors may be benign and therefore lack the invasive effects of cancer. Tumors may also be pre-malignant; that is, the tumor may lead to cancer if left untreated. Malignant tumors may be characterized by a tendency to become progressively worse and to potentially result in death. Malignant tumors may be characterized by anaplasia, invasiveness, and metastasis. Malignancy is often a touchstone of cancer.

Cancers may be localized, which includes cancers that reside in a single tissue environment. Cancers may also be metastatic. In this case, cancer cells may invade surrounding tissues, frequently by breaking through the basal laminas that create tissue boundaries, and spread to other areas of the body where they may establish secondary areas of growth. Blood-based cancers, such as leukemia, are able to outcompete the normal hematopoietic compartments in a subject, thereby leading to hematopoietic failure (in the form of anemia, thrombocytopenia and neutropenia) ultimately causing death. Metastases may be detected through the sole or combined use of magnetic resonance imaging (MRI) scans, computed tomography (CT) scans, blood and platelet counts, liver function studies, chest X-rays and bone scans in addition to the monitoring of specific symptoms.

Cancer causation may be linked to genetic and environmental factors. Exemplary cancer-critical genes can be classified roughly into two groups based on whether mutations in them cause loss of function or gain of function outcomes. Loss-of-function mutations of tumor suppressor genes relieve cells of inhibitions that normally help to hold their numbers in check, while gain-of-function mutations of proto-oncogenes stimulate cells to increase their numbers when they should not. Notable tumor suppressor genes include PTEN, p53, and INPP4B, among many others.

In some embodiments, the present invention encompasses methods of treating or preventing cancer and/or a metastasis in a subject in need thereof. In some embodiments, representative cancers and/or tumors and/or metastases of the present invention include a basal cell carcinoma, biliary tract cancer; bladder cancer; bone cancer; brain and central nervous system cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma; hepatic carcinoma; hepatoma; intra-epithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); melanoma; myeloma; neuroblastoma; oral cavity cancer (lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulval cancer; lymphoma including Hodgkin's and non-Hodgkin's lymphoma, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia; chronic lymphocytic leukemia (CLL); acute lymphoblastic leukemia (ALL); Hairy cell leukemia; chronic myeloblastic leukemia; as well as other carcinomas and sarcomas; and post-transplant lymphoproliferative disorder (PTLD), as well as abnormal vascular proliferation associated with phakomatoses, edema (such as that associated with brain tumors), and Meigs' syndrome. See, e.g., Weinberg, *The Biology of Cancer*, Garland Science: London 2006, the contents of which are hereby incorporated by reference.

In some embodiments, the cancer to be treated or prevented is a blood-based cancer or related disease including, for example, a leukemia, lymphoma, myeloma or myelodysplastic/myeloproliferative neoplasm (MDS/MPN).

In some embodiments, the present invention relates to leukemias. Leukemias are a type of cancer of the blood or bone marrow that are characterized by an abnormal increase of immature white blood cells. Leukemia is a broad subset of hematological neoplasms covering a spectrum of diseases. In various embodiments, the leukemia is acute or chronic. Acute leukemia is characterized by a rapid increase in the number of immature blood cells. Crowding due to such cells makes the bone marrow unable to produce healthy blood cells. Immediate treatment is often provided in acute leukemia due to the rapid progression and accumulation of the malignant cells, which then spill over into the bloodstream and spread to other organs of the body. Acute leukemia often is observed in younger individuals. Chronic leukemia is often characterized by an excessive build up of relatively mature, but still abnormal, white blood cells. This type of leukemia often takes months or years to progress but cells are produced at a much higher rate than normal, resulting in many abnormal white blood cells. Whereas acute leukemia may be treated immediately, chronic forms are sometimes monitored for some time before treatment to ensure maximum effectiveness of therapy. Chronic leukemia mostly occurs in older people, but can theoretically occur in any age group.

In various embodiments the leukemia is subdivided according to which kind of blood cell is affected. This classifies leukemias into lymphoblastic or lymphocytic leukemias and myeloid or myelogenous leukemias. In lymphoblastic or lymphocytic leukemias, the cancerous change takes place in a type of marrow cell that normally goes on to form lymphocytes. Most lymphocytic leukemias involve B cells. In myeloid or myelogenous leukemias, the cancerous change takes place in a type of marrow cell that normally goes on to form red blood cells, some other types of white cells, and platelets.

In some embodiments, the leukemia is acute lymphocytic leukemia (ALL), acute myelogenous leukemia (AML), chronic lymphocytic leukemia (CLL), or chronic myelogenous leukemia (CML). In some embodiments, the leukemia is hairy cell leukemia (HCL), T-cell prolymphocytic leukemia (T-PLL), large granular lymphocytic leukemia, or adult T-cell leukemia.

In some embodiments, the lymphoma is a Hodgkin lymphoma or a non-Hodgkin lymphoma. In some embodiments, the lymphoma is precursor T-cell leukemia/lymphoma, f, d, mantle cell lymphoma, B-cell chronic lymphocytic leukemia/lymphoma, MALT lymphoma, Burkitt's lymphoma, mycosis fungoides, peripheral T-cell lymphoma-not-otherwise-specified, nodular sclerosis form of Hodgkin lymphoma, or mixed-cellularity subtype of Hodgkin lymphoma.

In some embodiments, the myeloma is IgG, IgE, IgA, IgM, IgD, light chain, or non-secretory myeloma. In some embodiments, the myeloma is multiple myeloma.

In some embodiments, the invention relates to myelodysplastic/myeloproliferative neoplasm (MDS/MPN) or a disease related thereto. MDS is a group of diseases that affect the bone marrow and blood. In MDS, the blood-forming cells in the marrow slow down, or even stop, making blood cells. Many patients with MDS will develop anemia and may need blood transfusions. Some patients also have low numbers of white blood cells and platelets. Some types of MDS are mild and easily managed, while other types are severe and life-threatening. Mild MDS can grow more severe over time and may develop into a blood-based cancer, such as acute myelogenous leukemia (AML). Although MDS can affect people of any age, the majority of sufferers are older than 60 years. Exposure to certain industrial chemicals (e.g. tobacco smoke, pesticides, fertilizers, and solvents, such as, for example, benzene, and heavy metals, such as, for example, mercury and lead) or radiation can increase the risk of developing MDS. In some cases, MDS is labeled secondary MDS and is caused by chemotherapy used to treat a different disease.

In some embodiments, the MDS is one or more of refractory anemia (RA), refractory cytopenia with unilineage dysplasia (RCUD), refractory anemia with ringed sideroblasts (RARS), refractory cytopenia with multilineage dysplasia (RCMD), refractory anemia with excess blasts-1 (RAEB-1), refractory anemia with excess blasts-2 (RAEB-2), myelodysplastic syndrome, unclassified (MDS-U), and myelodysplastic syndrome associated with isolated del(5q).

In some embodiments, the cancer to be treated or prevented is a breast cancer. Breast cancer is a type of cancer originating from breast tissue, including the inner lining of milk ducts (ductal carcinomas) or the lobules that supply the ducts with milk (lobular carcinomas). Breast cancer occurs in humans and other mammals. Most human cases occur in women, male breast cancer can also occur. In some embodiments, the present invention pertains to a female human breast cancer subject. In some embodiments, the present invention pertains to a male human breast cancer subject.

In some embodiments, the present invention relates to breast cancers that are classified by one or more grading systems, which may, influence the prognosis and can affect treatment response. Histopathology, describes the classification of breast cancer by its histological appearance. Most breast cancers are derived from the epithelium lining the ducts or lobules, and these cancers are classified as ductal or lobular carcinoma. Carcinoma in situ is growth of low grade cancerous or precancerous cells within a particular tissue compartment such as the mammary duct without invasion of the surrounding tissue. By contrast, invasive carcinoma does not confine itself to the initial tissue compartment. Grading compares the appearance of breast cancer cells to the appearance of normal breast tissue. In some embodiments, cancerous cells lose the differentiation and orderly arrangement that characterizes normal cells and normal populations of cells. Further, cell division may become uncontrolled and cell nuclei may become less uniform. Cells can be binned as well differentiated (low grade), moderately differentiated (intermediate grade), and poorly differentiated (high grade) as the cells progressively lose the features seen in normal breast cells. Poorly differentiated cancers (the ones whose tissue is least like normal breast tissue) have a worse prognosis. Breast cancer staging can be undertaken using the TNM system, which is based the size of the tumor (T), whether or not the tumor has spread to the lymph nodes (N) in the armpits, and whether the tumor has metastasized (M). Larger size, nodal spread, and metastasis have a larger stage number and a worse prognosis. The main stages are: stage 0 is a pre-cancerous or marker condition, either ductal carcinoma in situ (DCIS) or lobular carcinoma in situ (LCIS); stages 1-3 are within the breast or regional lymph nodes; and stage 4 is metastatic cancer that often has a less favorable prognosis. DNA testing of various types including DNA microarrays may also be used to compare normal cells to breast cancer cells. The specific changes in a particular breast cancer can be used to classify the cancer in several ways, and may assist in choosing the most effective treatment for that DNA type.

Further, receptor status is important for classifying cancers, and the receptor status can be important for determining the optimum course of treatment. Breast cancer cells have receptors on their surface and in their cytoplasm and nucleus. Chemical messengers such as hormones bind to receptors, and this causes changes in the cell. Breast cancer cells of the present invention may or may not have at least five important receptors: estrogen receptor (ER), progesterone receptor (PR), and HER2, androgen receptor (AR), and the prolactin receptor (PRLr). In some embodiments, the present invention relates to the treatment of a breast cancer that is one or more of $ER^+$, $PR^+$, $HER2^+$, $AR^+$, and $PRLr^+$. In some embodiments, the present invention relates to the treatment of a breast cancer that is one or more of $ER^-$, $PR^-$, $HER2^-$, $AR^-$, and $PRLr^-$.

As used herein, the term subject or patient refers to any vertebrate including, without limitation, humans and other primates (e.g., chimpanzees and other apes and monkey species), farm animals (e.g., cattle, sheep, pigs, goats, and horses), domestic mammals (e.g., dogs and cats), laboratory animals (e.g., rodents such as mice, rats, and guinea pigs), and birds (e.g., domestic, wild and game birds such as chickens, turkeys and other gallinaceous birds, ducks, geese, and the like). In some embodiments, the subject is a mammal. In some embodiments, the subject is a human.

Another embodiment of the present invention is a pharmaceutical composition, or use of pharmaceutical composition, comprising an inhibitor of an miRNA, such as miR-22, and a pharmaceutically acceptable carrier. Where clinical applications are contemplated, pharmaceutical compositions may be prepared in a form appropriate for the intended application. Generally, this will entail preparing compositions that are essentially free of pyrogens, as well as other impurities that could be harmful to humans or animals.

In one embodiment, a pharmaceutical composition comprises an effective dose of an miRNA inhibitor, by way of non-limiting example, an antisense oligonucleotide directed to miR-22, and a pharmaceutically acceptable carrier. An effective dose is an amount sufficient to affect a beneficial or desired clinical result. An effective dose of an miRNA inhibitor of the invention may be from about 1 mg/kg to about 100 mg/kg, about 2.5 mg/kg to about 50 mg/kg, or about 5 mg/kg to about 25 mg/kg. The precise determination of what would be considered an effective dose may be based on factors individual to each patient, including their size, age, type of cancer, and nature of inhibitor or agonist (non-limiting examples include antagomir, expression construct, antisense oligonucleotide, polynucleotide duplex, etc.). Therefore, dosages can be readily ascertained by those of ordinary skill in the art from this disclosure and the knowledge in the art. For example, doses may be determined with reference *Physicians' Desk Reference*, 66th Edition, PDR Network; 2012 Edition (Dec. 27, 2011), the contents of which are incorporated by reference in its entirety.

A beneficial or desired clinical result may include, inter alia, a reduction in tumor size and/or tumor growth and/or a reduction of a cancer marker that is associated with the presence of cancer as compared to what is observed without administration of the inhibitor. A beneficial or desired clinical result may also include, inter alia, an increased presence of a marker that is associated with a reduction of cancer as compared to what is observed without administration of the inhibitor. Also included in a beneficial or desired clinical result is, inter alia, an increased amount of a gene comprising a marker linked to cancer etiology as compared to what is observed without administration of the inhibitor. The gene comprising a marker linked to cancer etiology may include, for example, TET2.

Colloidal dispersion systems, such as macromolecule complexes, nanocapsules, microspheres, beads, and lipid-based systems including oil-in-water emulsions, micelles, mixed micelles, and liposomes, may be used as delivery vehicles for the oligonucleotide inhibitors of oncogenic miRNA function, polynucleotides encoding tumor suppressor miRNA agonists, or constructs expressing particular miRNA inhibitors or agonists. Commercially available fat emulsions that are suitable for delivering the nucleic acids of the invention to cancer tissues include INTRALIPID®, LIPOSYN®, LIPOSYN® II, LIPOSYN® III, Nutrilipid, and other similar lipid emulsions. A colloidal system for use as a delivery vehicle in vivo is a liposome (i.e., an artificial membrane vesicle). The preparation and use of such systems is well known in the art. Exemplary formulations are also disclosed in U.S. Pat. No. 5,981,505; U.S. Pat. No. 6,217,900; U.S. Pat. No. 6,383,512; U.S. Pat. No. 5,783,565; U.S. Pat. No. 7,202,227; U.S. Pat. No. 6,379,965; U.S. Pat. No. 6,127,170; U.S. Pat. No. 5,837,533; U.S. Pat. No. 6,747,014; and WO03/093449, which are herein incorporated by reference in their entireties.

One will generally desire to employ appropriate salts and buffers to render delivery vehicles stable and allow for uptake by target cells. Aqueous compositions of the present invention comprise an effective amount of the delivery vehicle comprising the inhibitor polynucleotides (e.g., liposomes or other complexes or expression vectors) dissolved or dispersed in a pharmaceutically acceptable carrier or aqueous medium. The phrases pharmaceutically acceptable or pharmacologically acceptable refer to molecular entities and compositions that do not produce adverse, allergic, or other untoward reactions when administered to an animal or a human. As used herein, pharmaceutically acceptable carrier includes solvents, buffers, solutions, dispersion media, coatings, antibacterial and antifungal agents, isotonic and absorption delaying agents and the like acceptable for use in formulating pharmaceuticals, such as pharmaceuticals suitable for administration to humans. The use of such media and agents for pharmaceutically active substances is well known in the art. Except insofar as any conventional media or agent is incompatible with the active ingredients of the present invention, its use in therapeutic compositions is contemplated. Supplementary active ingredients also can be incorporated into the compositions, provided they do not inactivate the vectors or polynucleotides of the compositions.

The active compositions of the present invention may include classic pharmaceutical preparations. Administration of these compositions according to the present invention may be via any common route so long as the target tissue is available via that route. This includes oral, nasal, or buccal. Alternatively, administration may be by intradermal, subcutaneous, intramuscular, intraperitoneal or intravenous injection, or by direct injection into cancer tissue. The agents disclosed herein may also be administered by catheter systems. Such compositions would normally be administered as pharmaceutically acceptable compositions as described herein.

The active compounds may also be administered parenterally or intraperitoneally. By way of illustration, solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations generally contain a preservative to prevent the growth of microorganisms.

The pharmaceutical forms suitable for injectable use or catheter delivery include, for example, sterile aqueous solutions or dispersions and sterile powders for the extemporaneous preparation of sterile injectable solutions or dispersions. Generally, these preparations are sterile and fluid to the extent that easy injectability exists. Preparations should be stable under the conditions of manufacture and storage and should be preserved against the contaminating action of microorganisms, such as bacteria and fungi. Appropriate solvents or dispersion media may contain, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions may be prepared by incorporating the active compounds in an appropriate amount into a solvent along with any other ingredients (for example as enumerated above) as desired, followed by filtered sterilization. Generally, dispersions are prepared by incorporating the various sterilized active ingredients into a sterile vehicle which contains the basic dispersion medium and the desired other ingredients, e.g., as enumerated above. In the case of sterile powders for the preparation of sterile injectable solutions, the preferred methods of preparation include vacuum-drying and freeze-drying techniques which yield a powder of the active ingredient(s) plus any additional desired ingredient from a previously sterile-filtered solution thereof.

Upon formulation, solutions may be administered in a manner compatible with the dosage formulation and in such amount as is therapeutically effective. The formulations may easily be administered in a variety of dosage forms such as injectable solutions, drug release capsules and the like. For parenteral administration in an aqueous solution, for example, the solution generally is suitably buffered and the liquid diluent first rendered isotonic with, for example, sufficient saline or glucose. Such aqueous solutions may be used, for example, for intravenous, intramuscular, subcutaneous and intraperitoneal administration. Preferably, sterile aqueous media are employed as is known to those of skill in the art, particularly in light of the present disclosure. By way of illustration, a single dose may be dissolved in 1 ml of isotonic NaCl solution and either added to 1000 ml of hypodermoclysis fluid or injected at the proposed site of infusion (see, e.g, *Remington's Pharmaceutical Sciences*, 15th Edition, pages 1035-1038 and 1570-1580, the contents of which are hereby incorporated by reference). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by the FDA Office of Biologics standards.

In another embodiment of the present invention includes a method of treating or preventing cancer in a subject in need thereof comprising administering to the subject: a first inhibitor of a first miRNA, wherein the miRNA is miR-22 and a second inhibitor of a second miRNA, wherein the miRNA is a regulator of a cancer-related gene. In some embodiments, the second miRNA is a known miR inhibitor, including, by way of non-limiting example, those disclosed in International Patent Publication No. WO 2012/142313, the contents of which are hereby incorporated by reference in their entirety. In some embodiments, the first and second inhibitors may be administered in either order (e.g. first then second or second then first) or concurrently.

In another embodiment of the present invention includes a method of treating or preventing cancer in a subject in need thereof comprising administering to the subject a first agent that is or comprises an inhibitor of miR-22 and a second agent that is or comprises at least one other cancer biologic, therapeutic, chemotherapeutic or drug. In some embodiments, the first and second inhibitors may be administered in either order (e.g. first then second or second then first) or concurrently.

In some embodiments, the present invention includes various cancer biologics, therapeutics, chemotherapeutics, or drugs know in the art. For exemplary purposes only, and not intending to be limiting, the following drugs may be used in the present invention:

| Drug Name | Alternative Nomenclature |
|---|---|
| Altretamine | HEXALEN ®, hydroxymethylpentamethyl-melamine (HMPMM) |
| Bleomycin | BLENOXANE ® |
| Carboplatin | PARAPLATIN ® |
| Carmustine | BCNU, BICNU ® |
| Cisplatin | PLATINOL ®, CDDP |
| Cyclophosphamide | CYTOXAN ®, NEOSAR ®, 4-hydro-peroxycyclophosphamide, 4-HC |
| Docetaxel | TAXOTERE ®, D-Tax |
| Doxorubicin | ADRIAMYCIN ®, RUBEX ®, DOXIL ® |
| Epirubicin | ELLENCE ® |
| Erlotinib | TARCEVA ®, OSI-774 |
| Etoposide | VEPESID ®, ETOPOPHOS ®, VP-16 |
| Fluorouracil | ADRUCIL ®, 5-FU, EFUDEX ®, FLUOROPLEX ®, Capecitabine, XELODA ® |
| Gemcitabine | GEMZAR ® |
| Ifosfamide | IFEX ®, 4-hydroperoxyifosfamide, 4-HI |
| Irinotecan/SN-38 | CAMPTOSAR ®, CPT-11, SN-38 |
| Leucovorin | WELLCOVORIN ® |
| Lomustine | CCNU, CEENU ® |
| Melphalan | ALKERAN ®, L-PAM |
| Mitomycin | MUTAMYCIN ®, MITOZYTREX ®, Mitomycin-C |
| Oxaliplatin | ELOXATIN ® |
| Paclitaxel | TAXOL ®, ABRAXANE ® |
| Procarbazine | MATULANE ®, PCZ |
| Temozolomide | TEMODAR ® |
| Topotecan | HYCAMTIN ® |
| Vinblastine | VELBAN ®, EXAL ®, VELBE ®, VELSAR ®, VLB |
| Vincristine | ONCOVIN ®, VINCASAR PFS ®, VCR |
| Vinorelbine | NAVELBINE ®, NVB |

Another embodiment of the present invention includes a method of treating or preventing cancer in a subject in need thereof comprising administering an inhibitor of an oncogenic miRNA, including but not limited to miR-22, and/or a second inhibitor of an oncogenic miRNA, or a cancer biologic, therapeutic, chemotherapeutic or drug, which includes the further step of diagnosing a patient to identify the regulated tumor suppressor before treatment. Such diagnosis can include, among others, actually making the evaluation of tumor suppressor regulation or ordering that such a determination be made. Further, the selection of miRNA inhibitor and/or cancer biologic, therapeutic, chemotherapeutic or drug would be educated by the diagnosis.

In some embodiments, the present invention provides a method of evaluating a subject's cancer, including but not limited to diagnosis, prognosis, and response to treatment. In some embodiments, miR-22 is correlated with poor survival rates in patients with various cancers such as leukemia, MDS, and breast cancer. In some embodiments, the present invention relates to a method of evaluating a cancer based on measurement of miR-22 levels. In one embodiment, detection of miR-22 is associated with an aggressive cancer and an aggressive treatment regime is employed, optionally including adjuvant and neoadjuvant therapies. Adjuvant therapy, also called adjuvant care, is treatment that is given in addition to the primary, main or initial treatment. By way of non-limiting example, adjuvant therapy may be an additional treatment usually given after surgery where all detectable disease has been removed, but where there remains a statistical risk of relapse due to occult disease. In certain embodiments, neoadjuvant therapy refers to therapy to shrink and/or downgrade the tumor prior to any surgery. In some embodiments, neoadjuvant therapy means chemotherapy administered to cancer patients prior to surgery. In some embodiments, neoadjuvant therapy means an agent described herein administered to cancer patients prior to surgery. In another embodiment, detection of miR-22 is associated with an aggressive cancer and these circumstances may direct cessation of aggressive treatment and the use of palliative care, to avoid unnecessary toxicity from ineffective chemotherapies for a better quality of life.

The invention also provides kits that can simplify the administration of any agent described herein, such as an inhibitor of an oncogenic miRNA, including antisense oligonucleotide directed to miR-22. An exemplary kit of the invention comprises any composition described herein in unit dosage form. In one embodiment, the unit dosage form is a container, such as a pre-filled syringe, which can be sterile, containing any agent described herein and a pharmaceutically acceptable carrier, diluent, excipient, or vehicle. The kit can further comprise a label or printed instructions instructing the use of any agent described herein. The kit may also include a lid speculum, topical anesthetic, and a cleaning agent for the administration location. The kit can further comprise one or more additional agent, such as a second inhibitor of an oncogenic miRNA, or a biologic, therapeutic, chemotherapeutic or drug described herein. In one embodiment, the kit comprises a container containing an effective amount of a composition of the invention and an effective amount of another composition, such those described herein.

This invention is further illustrated by the following additional examples that should not be construed as limiting. Those of skill in the art should, in light of the present disclosure, appreciate that many changes can be made to the specific embodiments which are disclosed and still obtain a like or similar result without departing from the spirit and scope of the invention.

EXAMPLES

Figure 1B:
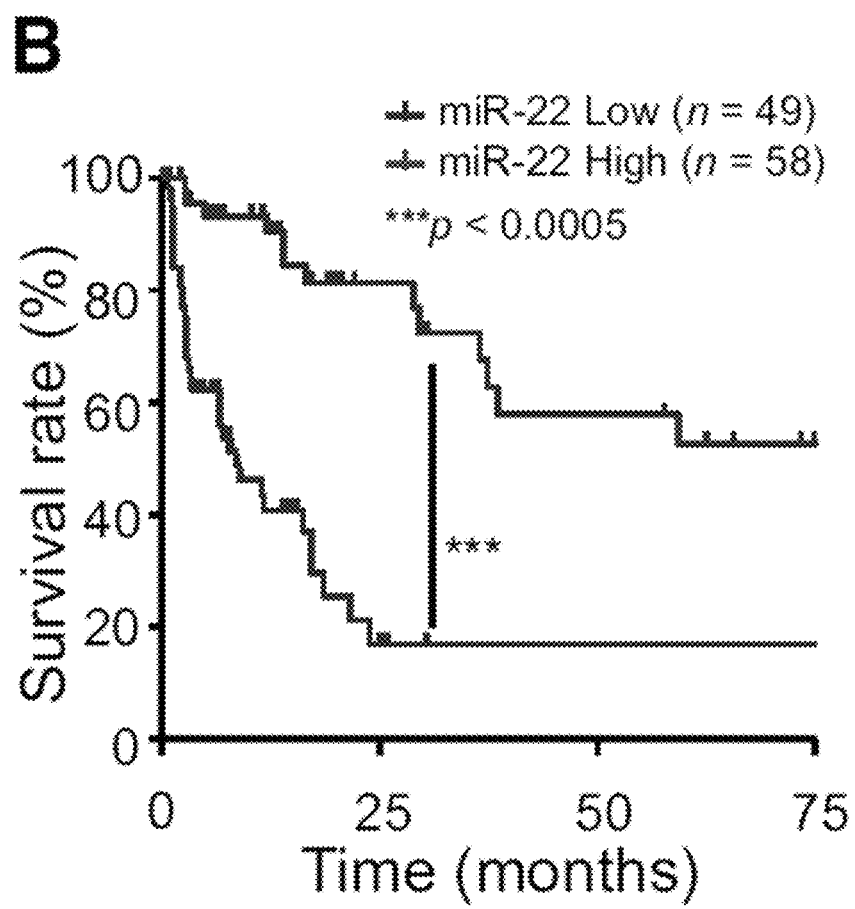

Example 1: miR-22 is Highly Expressed in Human Hematological Malignancies and Increases the Replating Ability of HSCs Expression analysis for miR-22 by in situ hybridization in a large set of patient samples, which included bone marrow with no sign of disease (n=37), early stage MDS (refractory anemia [RA], 5q syndrome [5q-], refractory cytopenia with multilineage dysplasia [RCMD], and RA with ringed sideroblasts [RARS]) (n=40), and RA with excess blasts (RAEB) (n=67) was performed. This analysis revealed that miR-22 is highly expressed in patients with MDS (FIG. 1A). The survival rates of the sets of MDS patients was estimated by using a Kaplan-Meier analysis and applying a log-rank test to compare the survival rates of MDS patients on the basis of miR-22 expression levels. Aberrant expression of miR-22 was found to directly correlate with poor survival rates in patients (FIG. 1B). A significant correlation between miR-22 levels and poor survival rates was observed within each WHO classification, as well as among MDS patients harboring a normal karyotype. This indicates that the poorer survival expectancy linked to miR-22 overexpression does not simply reflect confounding factors such as blast count and cytogenetic karyotype.

To explore the function of miR-22 in hematopoiesis and leukemia, mouse hematopoietic stem/progenitor cells (HSPCs; c-KitposSca-1posLinneg, hereafter referred to as KSL cells) isolated from wild-type donor mice were transduced with either a retroviral vector encoding miR-22 and a green fluorescent protein (GFP) or a control vector encoding GFP only. The GFP-expressing KSL cells were then resorted by flow cytometry and plated in methylcellulose for an in vitro colony-forming unit (CFU) assay. In the first plating it was observed that the cells expressing miR-22 produced fewer colonies compared to control cells; however, when GFP+KSL cells were resorted and replated, miR-22-transduced cells produced more colonies in the second plating. These cells also maintained this ability throughout serial replatings: whereas control cells only formed colonies in the first two platings, miR-22-expressing KSL cells were able to produce colonies after being replated at least seven times. Microscopic analysis of the cells from these colonies revealed a homogenous blast-like morphology. Consistent with these results, miR-22-expressing KSL cells maintained their characteristics and c-Kit expression (a marker of undifferentiated cells) during their replatings. To ensure that miR-22-transduced and control cells were subjected to the same experimental treatment, in vitro competitive colony assay was also performed by mixing GFP+ KSL cells expressing miR-22 and GFP– control KSL cells. This analysis confirmed that miR-22-expressing GFP+, but not GFP–, KSL cells remained mostly in colonies through consecutive replatings (FIG. S1L, bottom). Taken together, these data suggest that miR-22 can drive aberrant replating capacity of HSPCs and may contribute to malignant transformation.

Example 2: miR-22 Affects HSC Biology In Vivo

Figure 1C:
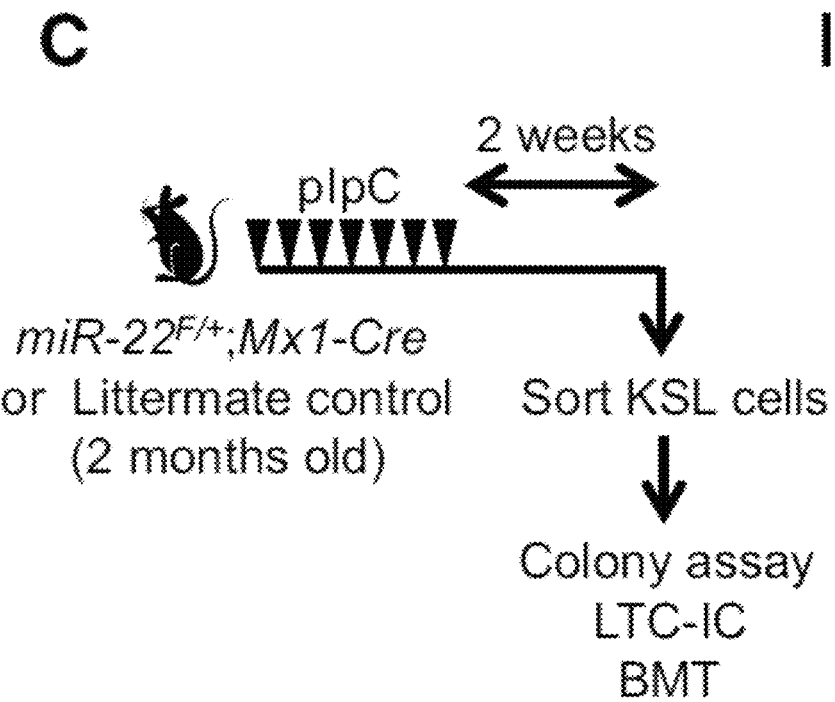
Figure 1D:
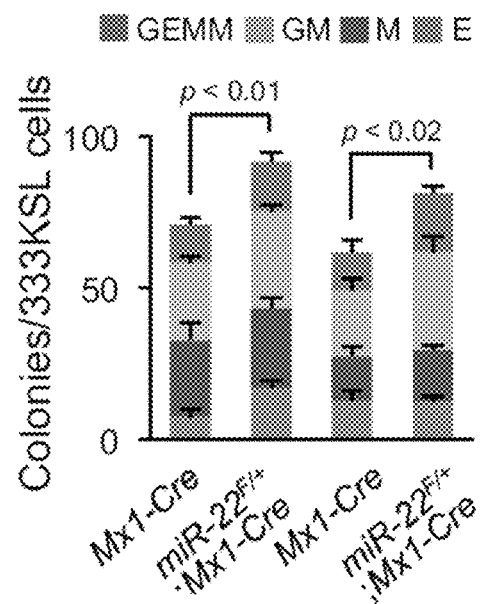
Figure 1E:
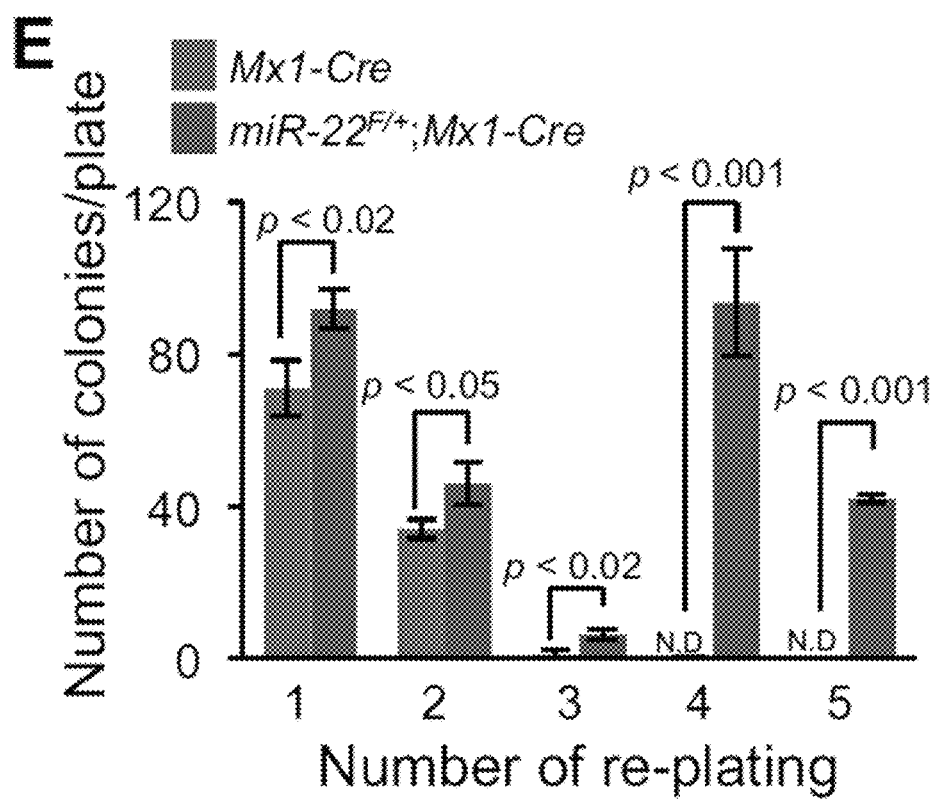
Figure 1F:
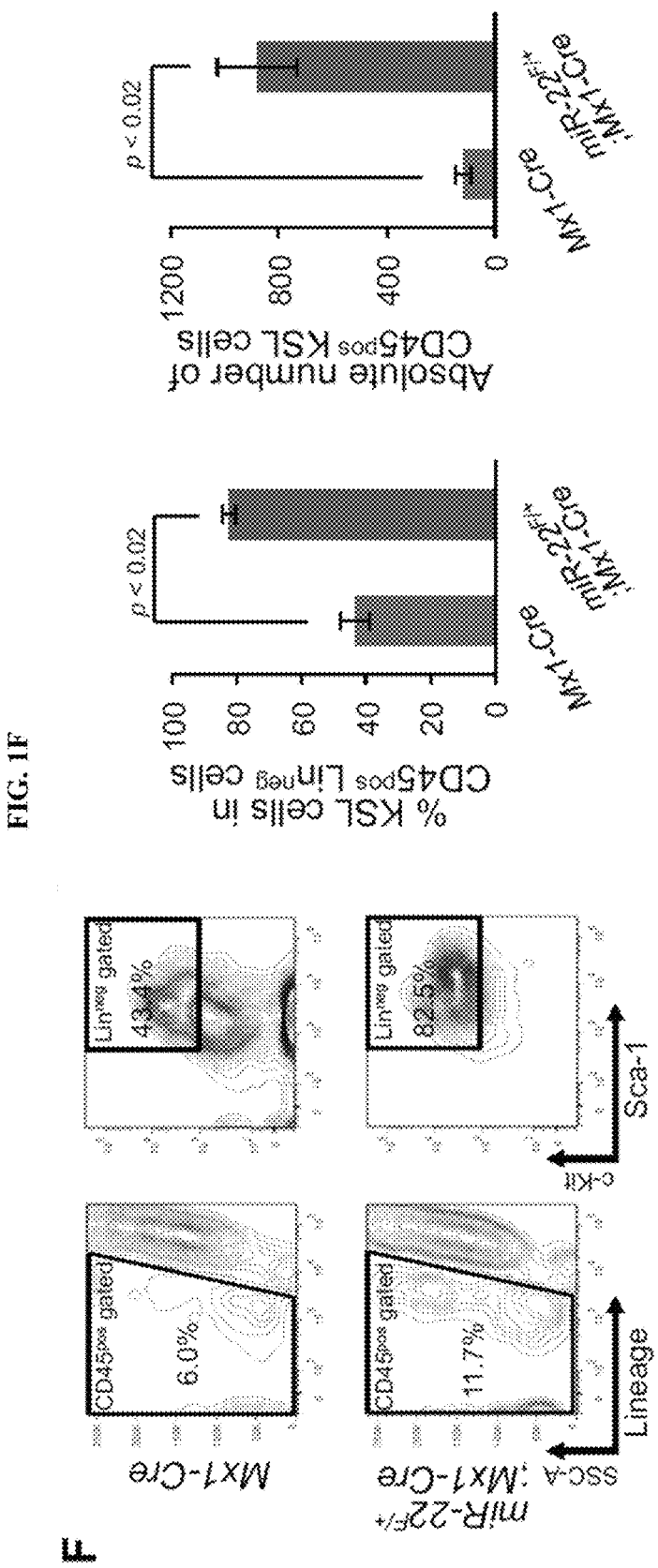

The biological effects of miR-22 in vivo were analyzed. A conditional transgenic mouse model overexpressing miR-22 in the hematopoietic compartment was generated. miR-22 expression was induced by Mxl-Cre-mediated excision of a LoxP flanked transcriptional STOP cassette by administration of seven doses of polyinosine-polycytidine (pIpC) over 14 days. Two weeks after pIpC administration, KSL cells were isolated from miR-22F/+;Mxl-Cre mice and Mxl-Cre littermate controls and their properties analyzed by using CFU and long-term culture initiating cell (LTC-IC) assays (FIGS. 1C-1G). KSL cells from miR-22F/+;Mxl-Cre transgenic mice displayed an enhanced replating potential (FIGS. 1D and 1E). Furthermore, ectopic expression of miR-22 caused a robust increase in the number of both KSL and mature myeloid cells, as determined by LTC-IC assay, indicating that miR-22 enhances HSPC maintenance and predisposes those cells to differentiate into the myeloid lineage (FIGS. 1F and 1G).

Figure 2A:
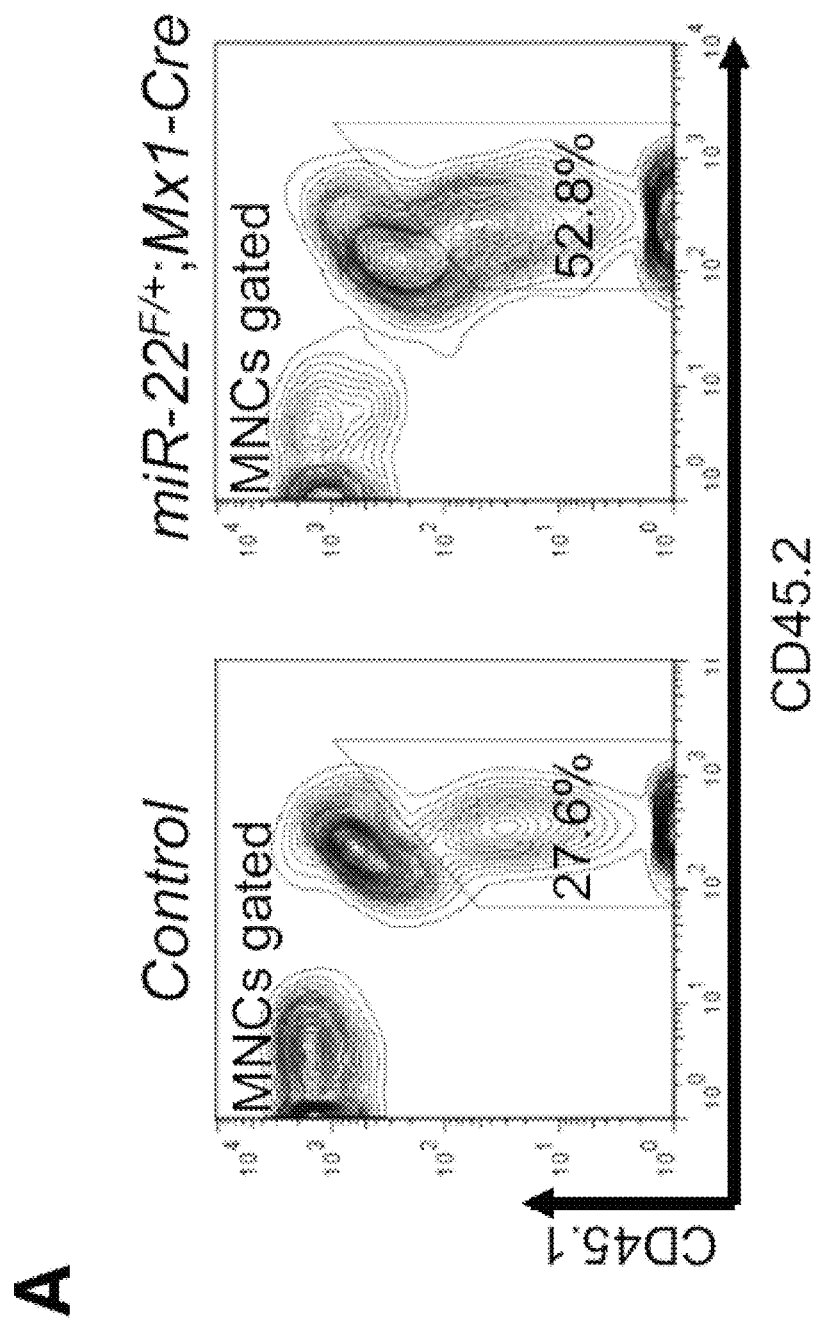
FIGS. 2A-F show that miR-22 leads to an enhanced repopulating capacity of HSPCS in vivo.
Figure 2B:
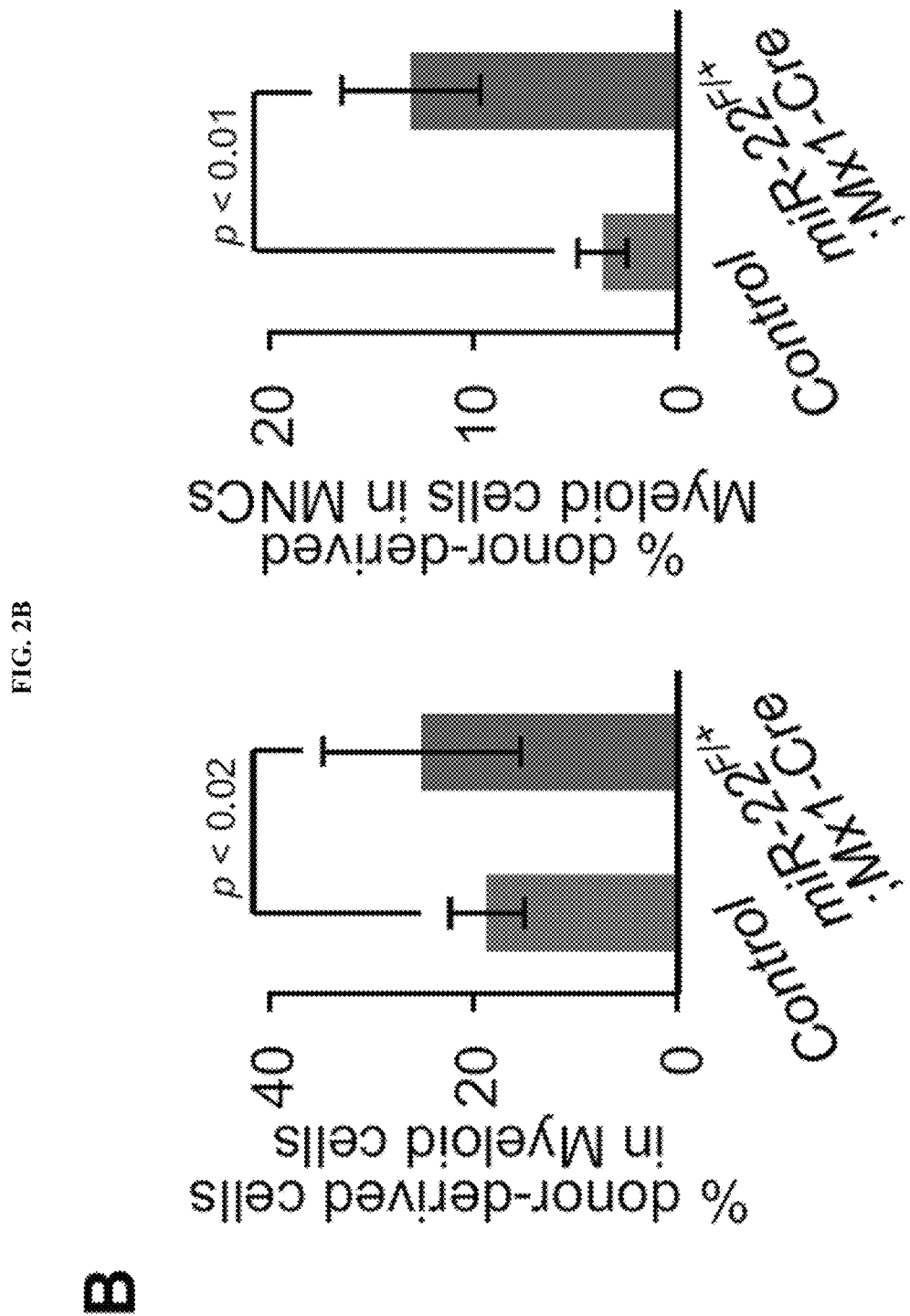
Figure 2C:
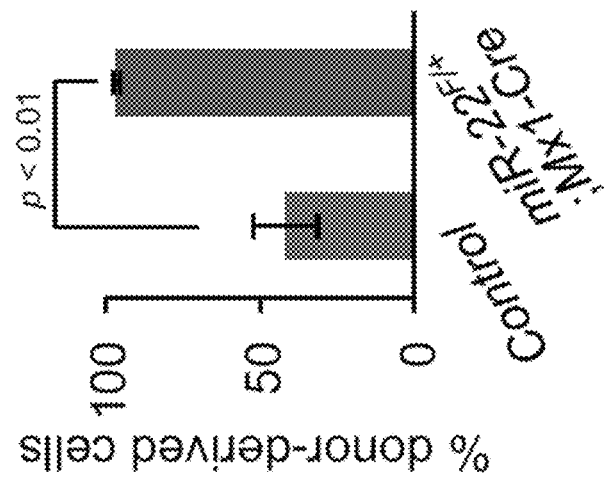
Figure 2C:
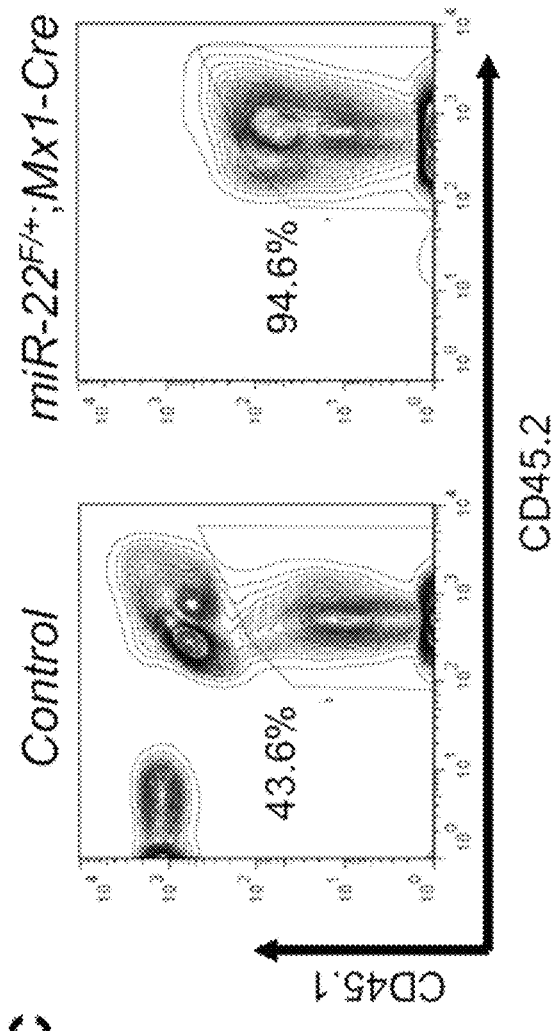
Figure 2D:
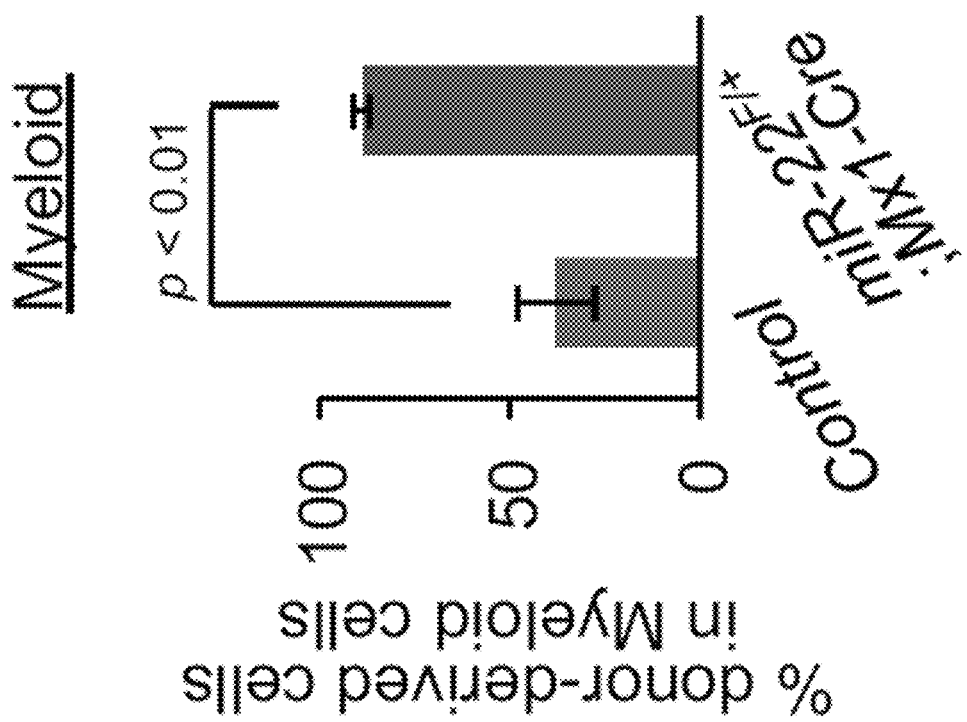
Figure 2E:
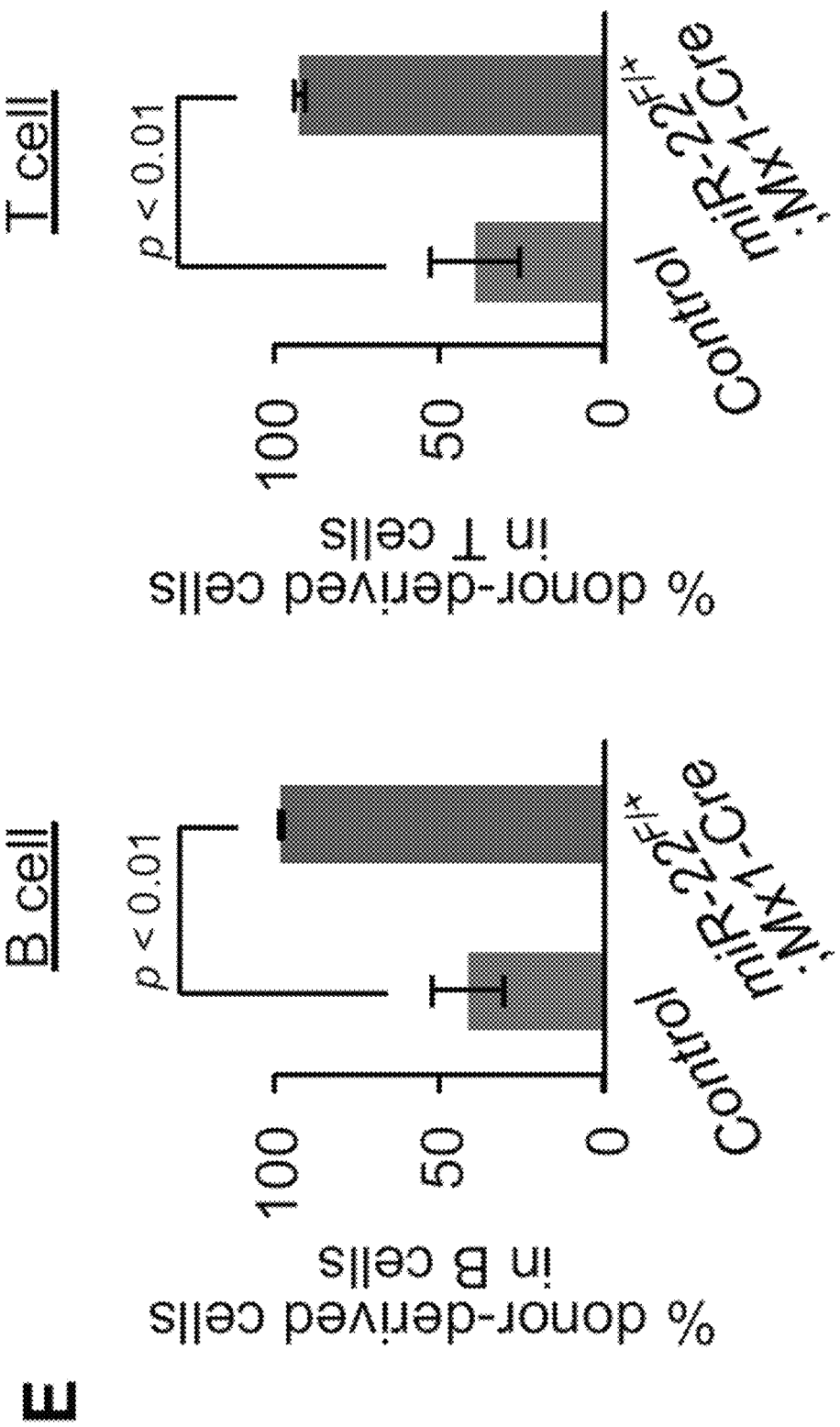
Figure 2F:
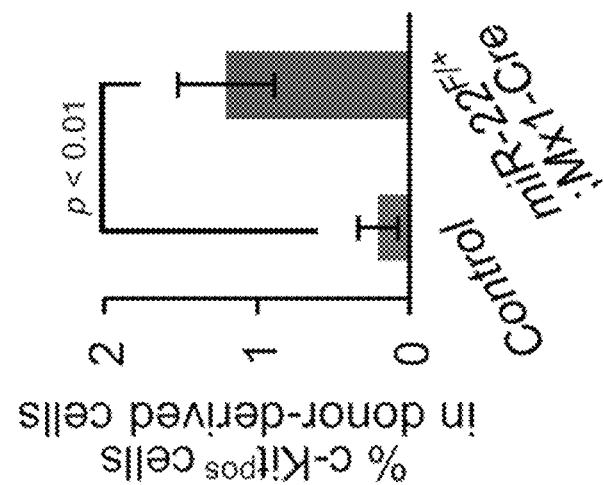
Figure 2F:
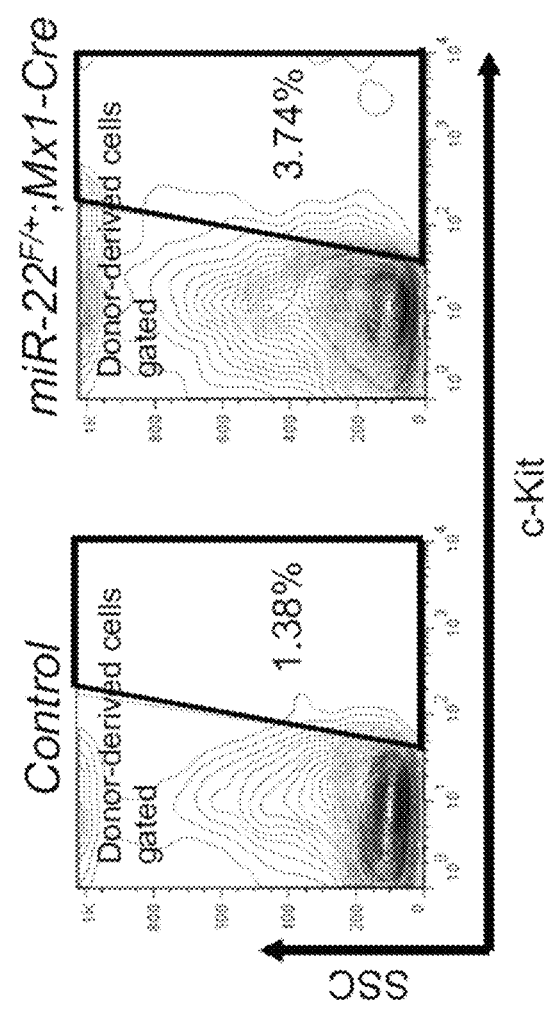
Figure 3A:
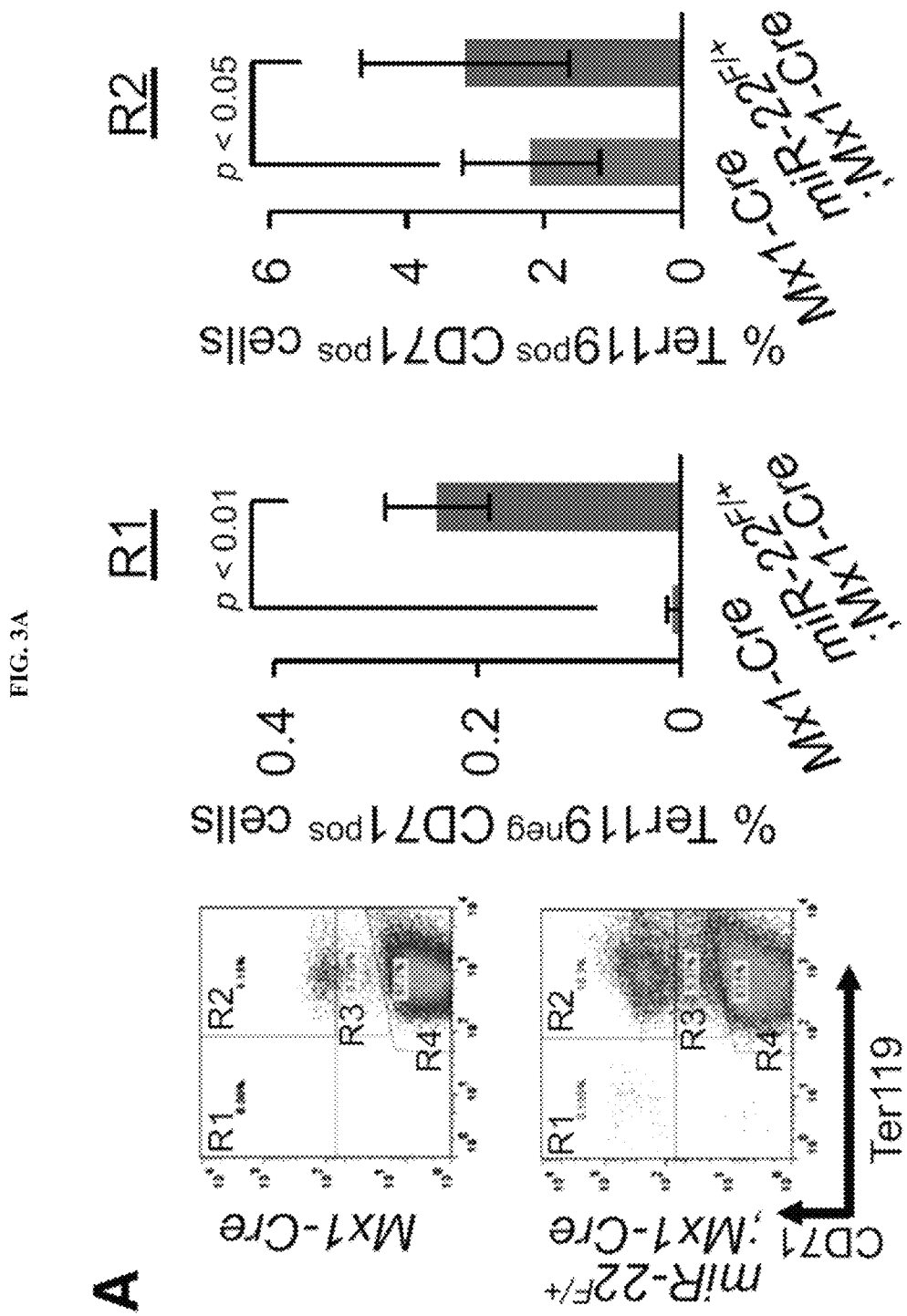
FIGS. 3A-E show miR-22 overexpression is linked to the development of hematological syndromes. All error bars indicate ±SD.
Figure 3B:
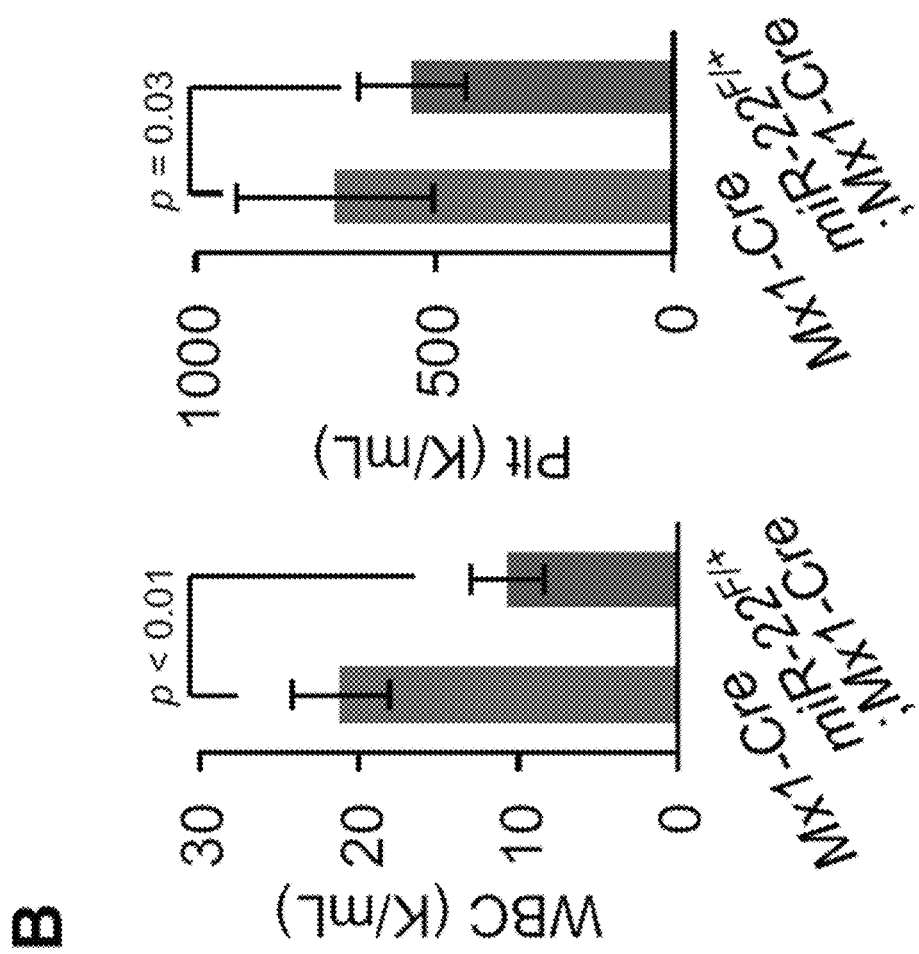
Figure 3C:
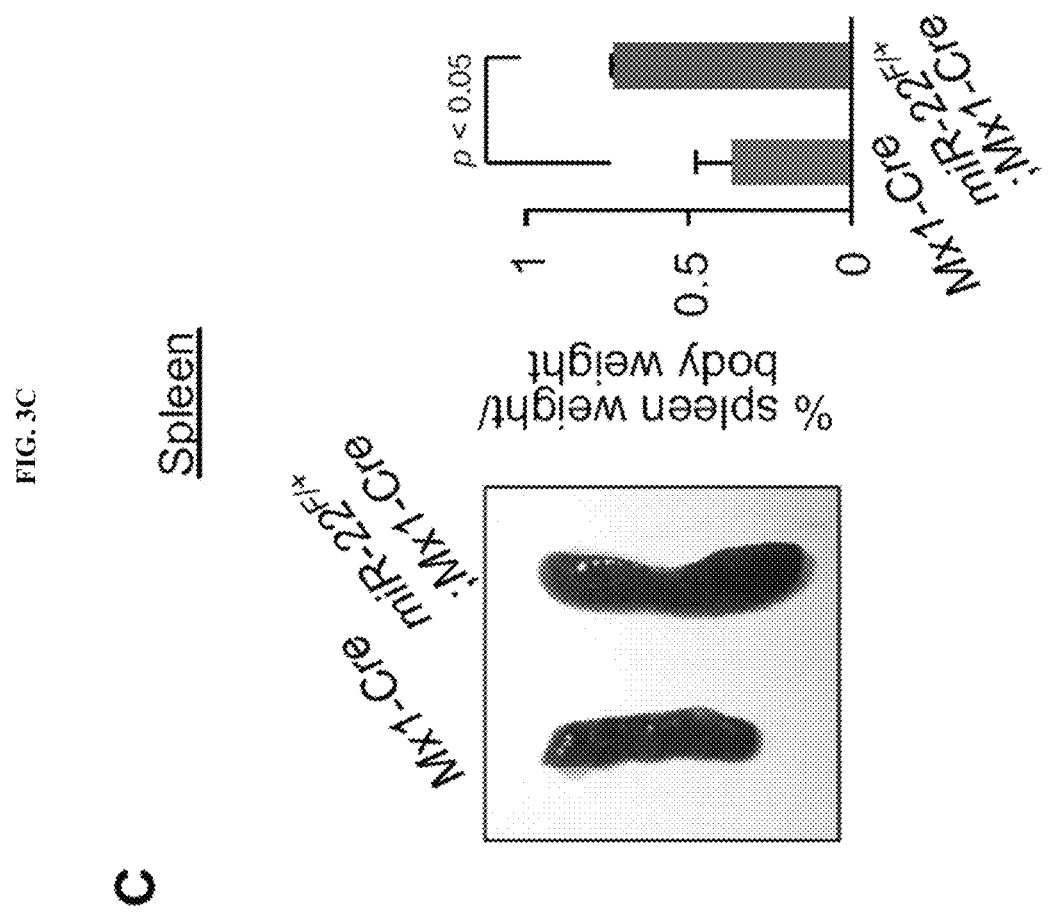
Figure 3D:
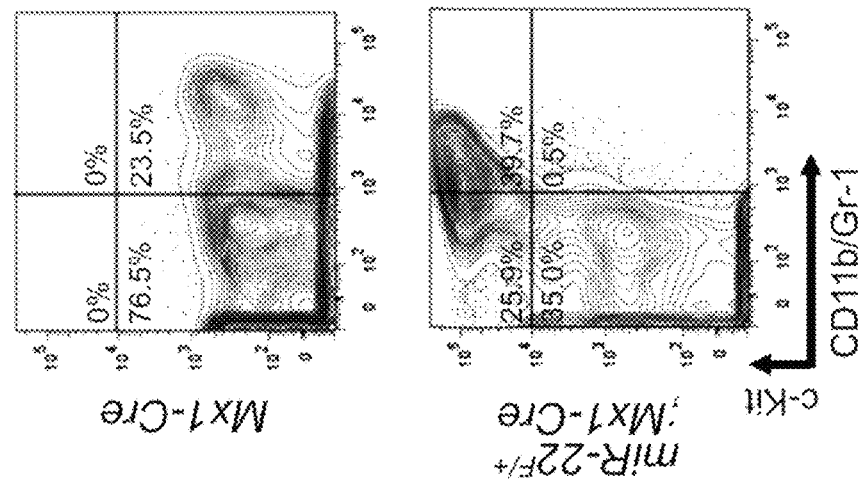
Figure 3E:
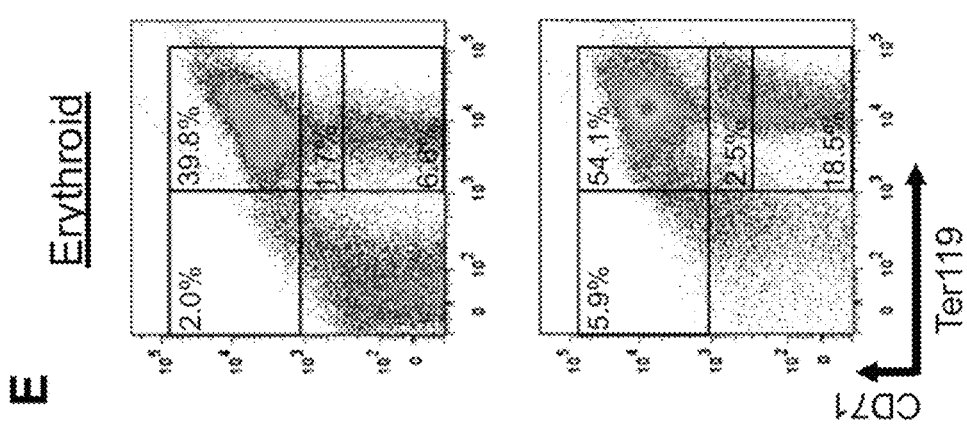

Next, the ability of miR-22-overexpressing HSPCs to compete with wild-type counterparts in vivo was examined by utilizing an in vivo competitive transplantation assay. KSL cells from miR-22F/+;Mxl-Cre and Mxl-Cre mice (Ly45.2) were purified 2 weeks after pIpC administration, mixed with Ly45.1/Ly45.2 competitor bone marrow mononuclear cells (BM MNCs), and transplanted into lethally irradiated Ly45.1 congenic recipient mice. The ability of donor cells to contribute to the reconstitution was then determined by flow cytometric analysis of peripheral blood stained for Ly45.1 and Ly45.2. Within 3 weeks of transplantation, donor cells from miR-22F/+;Mxl-Cre mice exhibited a slight increase in chimerism compared to those from control animals. Over time this difference became more pronounced as miR-22F/+;Mxl-Cre KSL cells outcompeted their wild-type counterparts (FIGS. 2A-2C). At 6 weeks post-transplantation, an increased chimerism was observed in all BM MNCs as well as within the myeloid fraction, and by 9 weeks this effect was also evident in the c-Kitpos fraction (FIGS. 2A-2F). These data show that miR-22 enhances the self-renewal capacity of HSPCs in vivo.

Figure 4A:
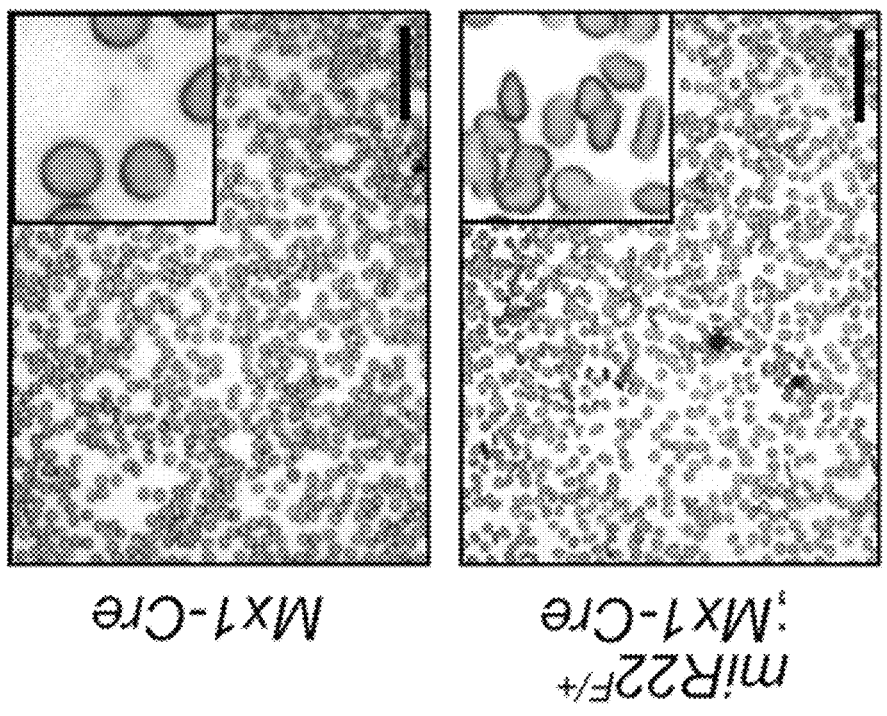
FIGS. 4A-G show that miR-22 transgenic mice develop primary hematological diseases. All error bars indicate ±SD.
Figure 4B:
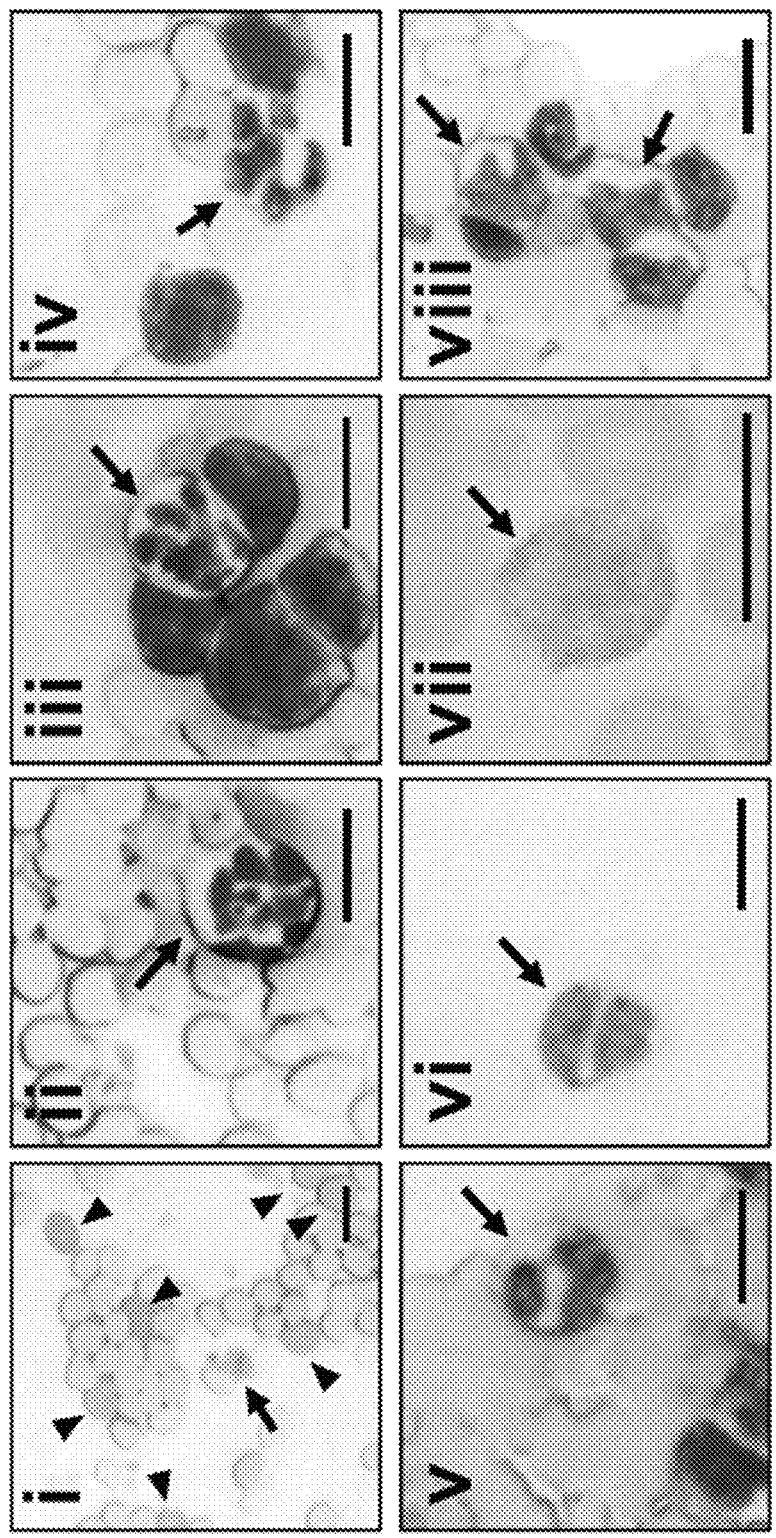
Figure 4C:
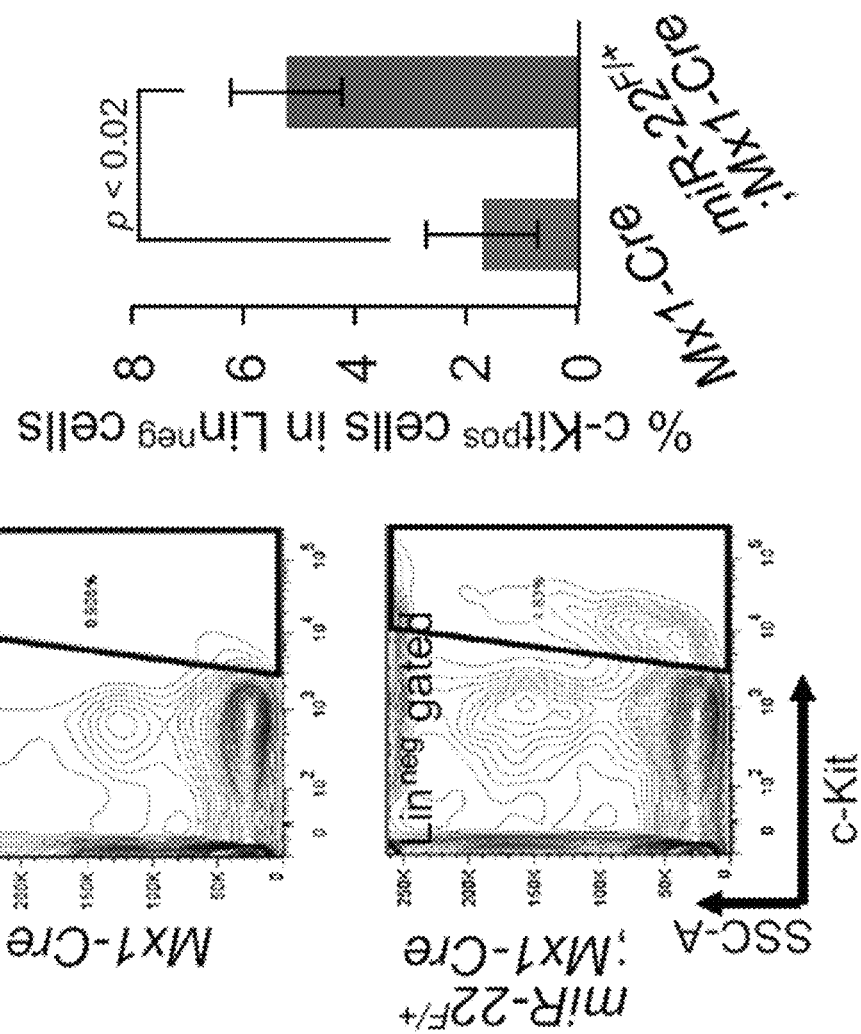
Figure 4D:
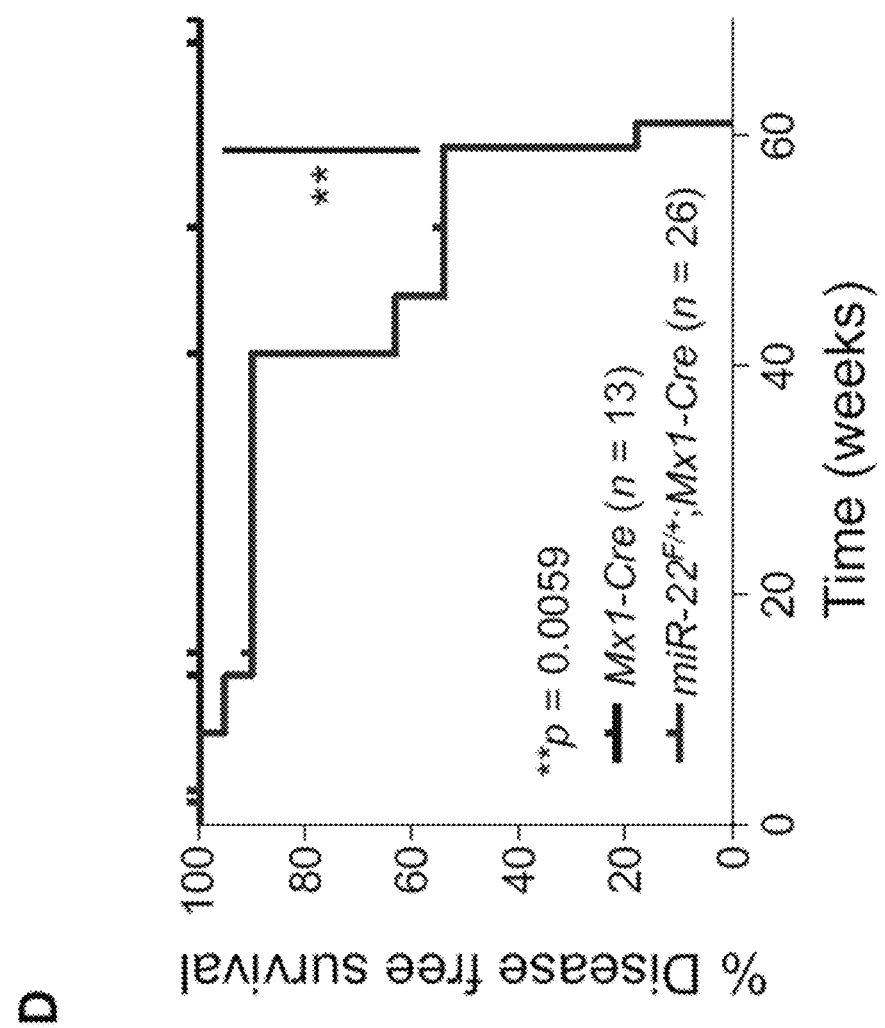
Figure 4E:
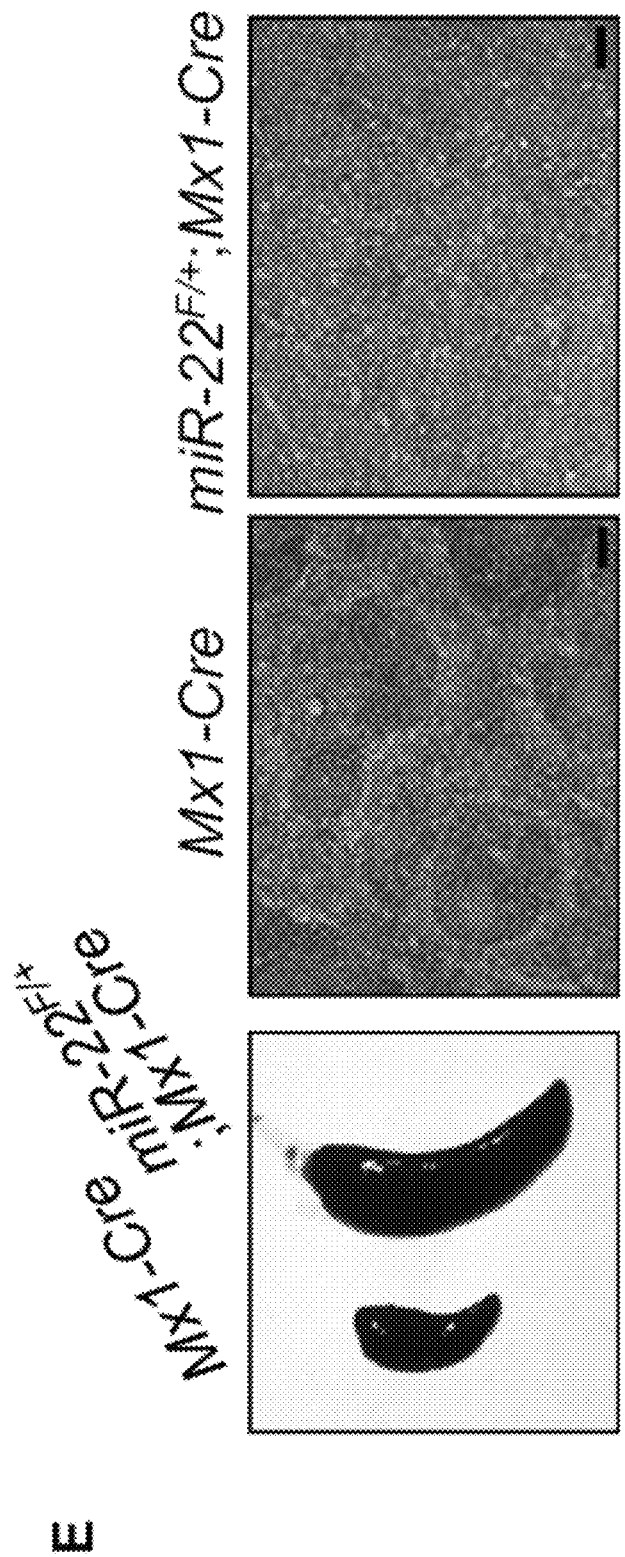
Figure 4F:
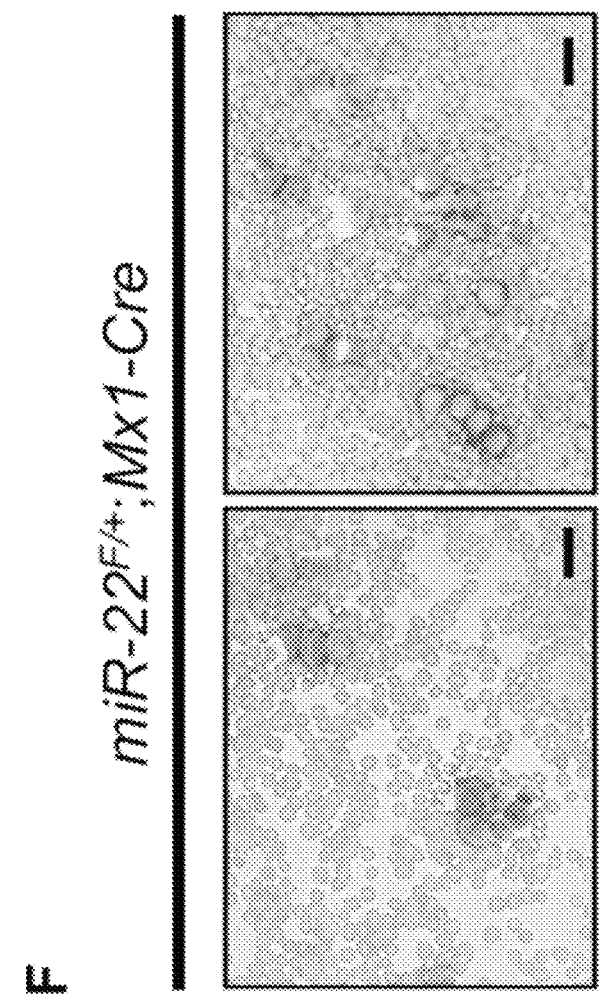
Figure 4G:
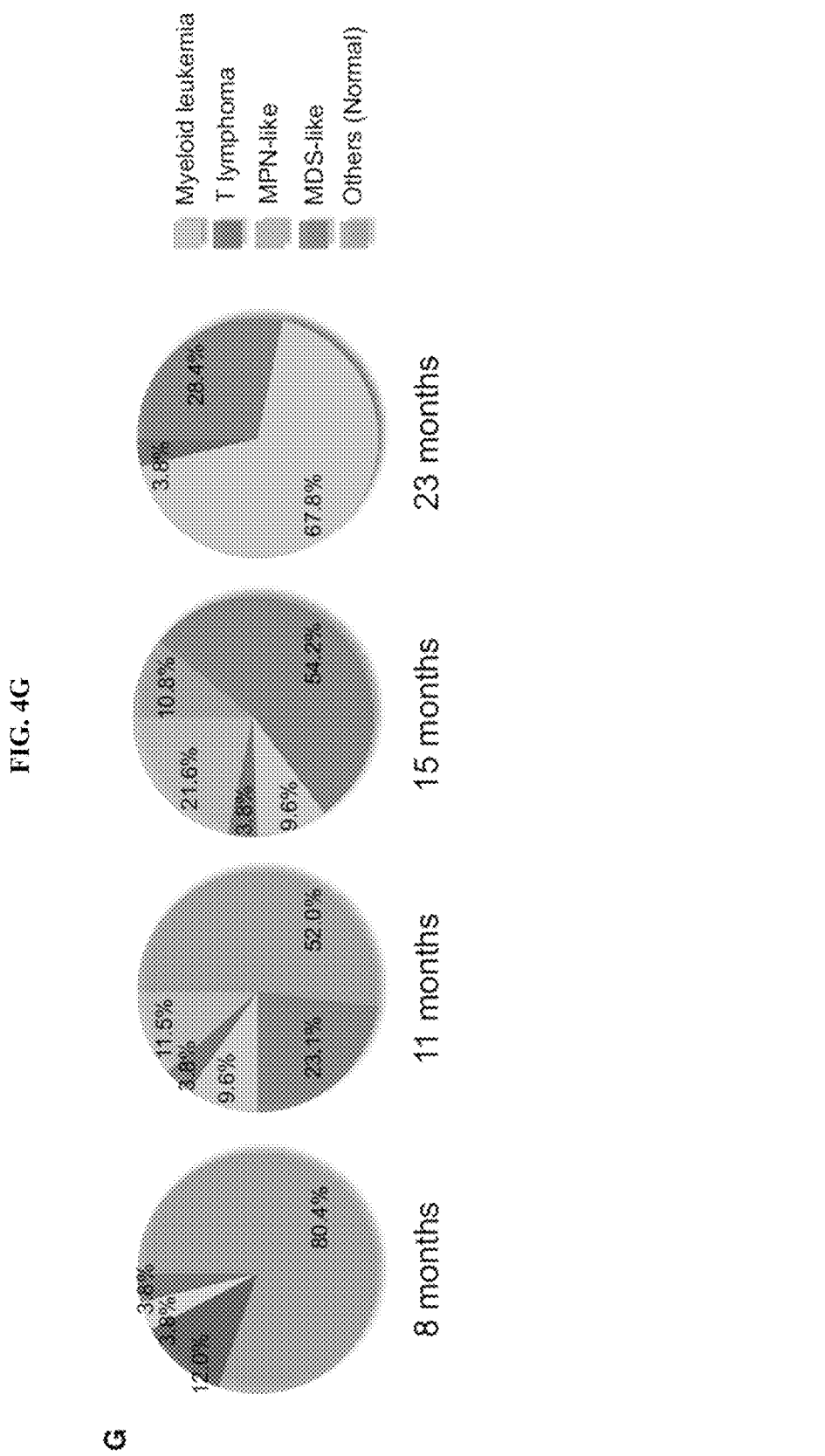

Example 3: miR-22 Triggers MDS-Like Syndromes and Hematological Malignancies In Vivo To further study that increased aberrant hematopoiesis is caused by miR-22 overexpression and ultimately progresses to malignant hematological disease, follow up on primarily transplanted recipients was continued. Notably, at 12 weeks post-transplantation, recipient mice transplanted with KSL cells from miR-22F/+;Mxl-Cre donors, but not from Mxl-Cre donors, developed an illness that closely resembled human MDS, as characterized by defective erythroid maturation and anemia, splenomegaly with myeloid infiltration, low white blood cell (WBC) counts, and dysplastic myeloid cells in the peripheral circulation (FIG. 3). To determine whether this disorder is transplantable, the donor-derived KSL cells resorted from primary recipient mice were subjected to a secondary transplantation using fresh competitor cells. All secondary recipients developed a lethal hematological disease within 4 weeks after secondary transplantation. Furthermore, disease onset and progression to malignancy in miR-22 transgenic mice was also monitored. The development of disease similar to that found in the chimeric transplantation model was observed in miR-22F/+;Mxl-Cre mice but not Mxl-Cre littermate controls at 8 months after pIpC administration. The hallmarks of this distress included dysplasia in many lineages including erythroid, myeloid, and platelet; splenomegaly; and an increased number of c-Kitpos undifferentiated blastic cells in the peripheral blood (FIGS. 4A-4C). By 16 months after pIpC administration, all miR-22 transgenic mice had developed MDS, affecting multilineage hematopoiesis. About 13% of mice succumbed to myeloid leukemia as well as T cell lymphoma by 11 months, and all miR-22 transgenic mice suffered from hematological abnormality by 16 months.

About 70% of miR-22 transgenic mice developed myeloid leukemia within 2 years (FIGS. 4D-4G). It was also confirmed that the disease was triggered by miR-22 from KSL cells sorted from miR-22-expressing colonies. To this end, miR-22-expressing cells were subjected to consecutive colony replating and at the sixth replating, the residual c-KitposLinneg (KL) cells were transplanted into lethally irradiated recipient mice. By 14 weeks after transplantation, recipient mice transplanted with miR-22-expressing cells developed myeloid leukemia, as characterized by increased myeloid blasts in the peripheral blood, defective erythroid maturation and anemia, splenomegaly with the infiltration of myeloid blasts, and increased c-Kitpos blasts in bone marrow. Taken together, these show that miR-22 can enhance HSPC function and contribute to leukemia development in vivo.

Example 4: miR-22 Directly Targets TET2 and Affects the Epigenetic Landscape of the Hematopoietic Compartment In Vivo To identify relevant molecular targets of miR-22, a bioinformatic analysis was undertaken using TargetScan 6.0 (Lewis et al., Conserved seed pairing, often flanked by adenosines, indicates that thousands of human genes are microRNA targets. Cell 120, 15-20.), microRNA.org (Betel et al., The microRNA.org resource: targets and expression. Nucleic Acids Res. 36(Database issue), D149-D153.), and miRBase (Griffiths-Jones et al., miRBase: microRNA sequences, targets and gene nomenclature. Nucleic Acids Res. 34 (Database issue), D140-D144.). Among various potential targets, the focus was on ten eleven translocation 2 (TET2) as it possesses critically conserved nucleotides indicative of a legitimate target. A direct interaction of miR-22 with the 30UTR region of the TET2 gene was shown by luciferase reporter assay.

It was also tested whether miR-22 could act as an authentic TET2-targeting miRNA in the hematopoietic compartment by utilizing the conditional transgenic mouse model. To this end, Tet2 expression was measured in the peripheral blood and bone marrow of miR-22F/+;Mxl-Cre or Mxl-Cre littermate mice at 2-3 weeks after pIpC administration. Real-time qPCR and western blot analyses revealed a marked reduction in levels of Tet2 mRNA and protein, respectively, in miR-22F/+;Mxl-Cre mice compared to littermate controls (FIGS. 5A, 5B, 5E-5G).

Figure 5A:
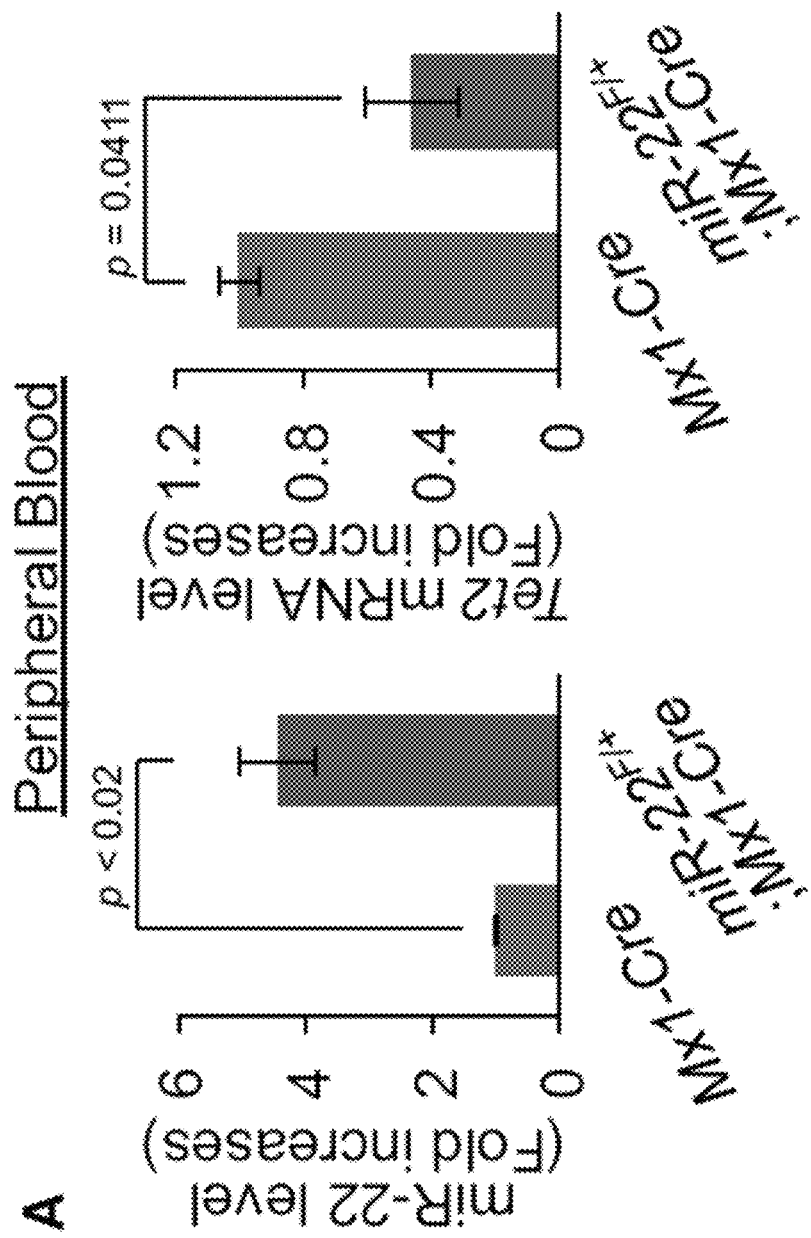
FIGS. 5A-G show that miR-22 acts as an epigenetic modifier by directly targeting TET2.
Figure 5B:
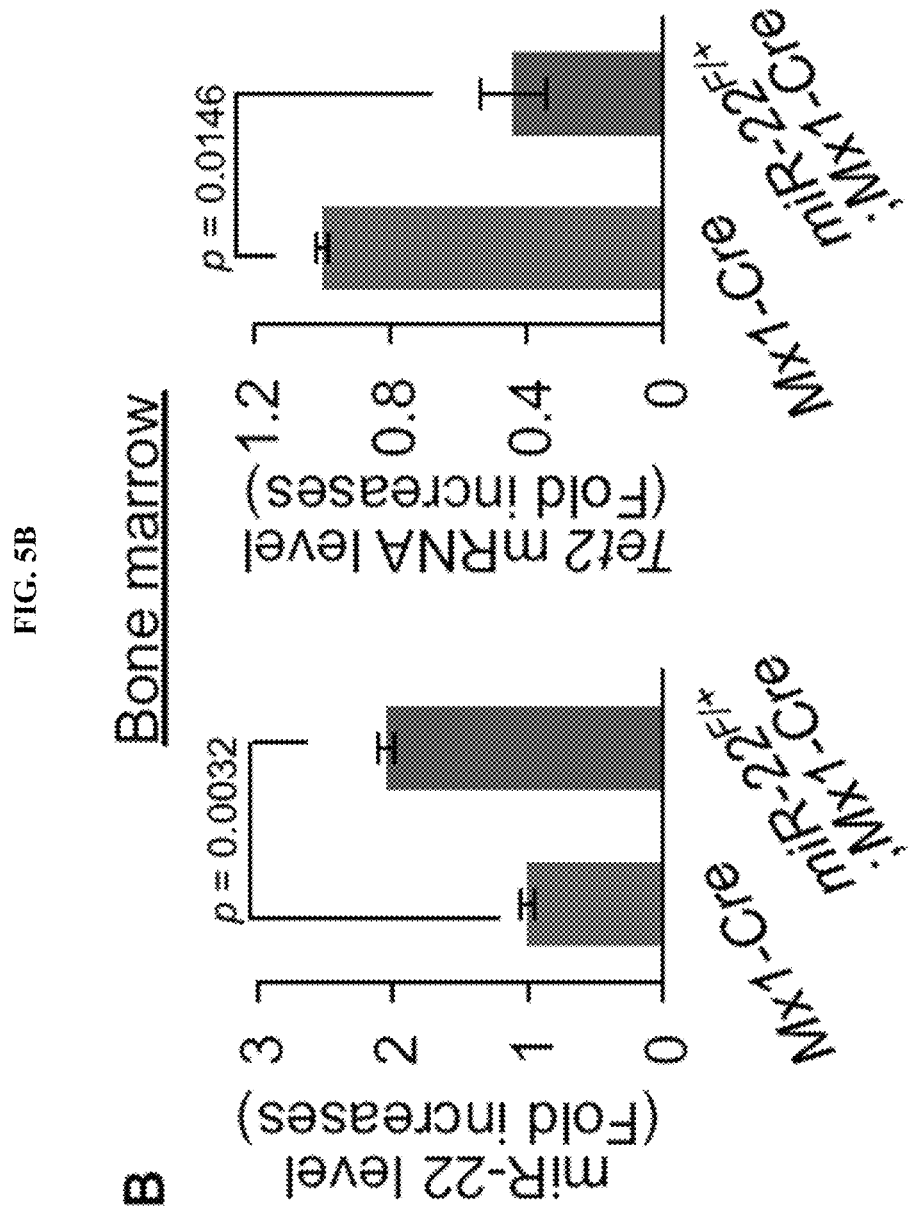
Figure 5C:
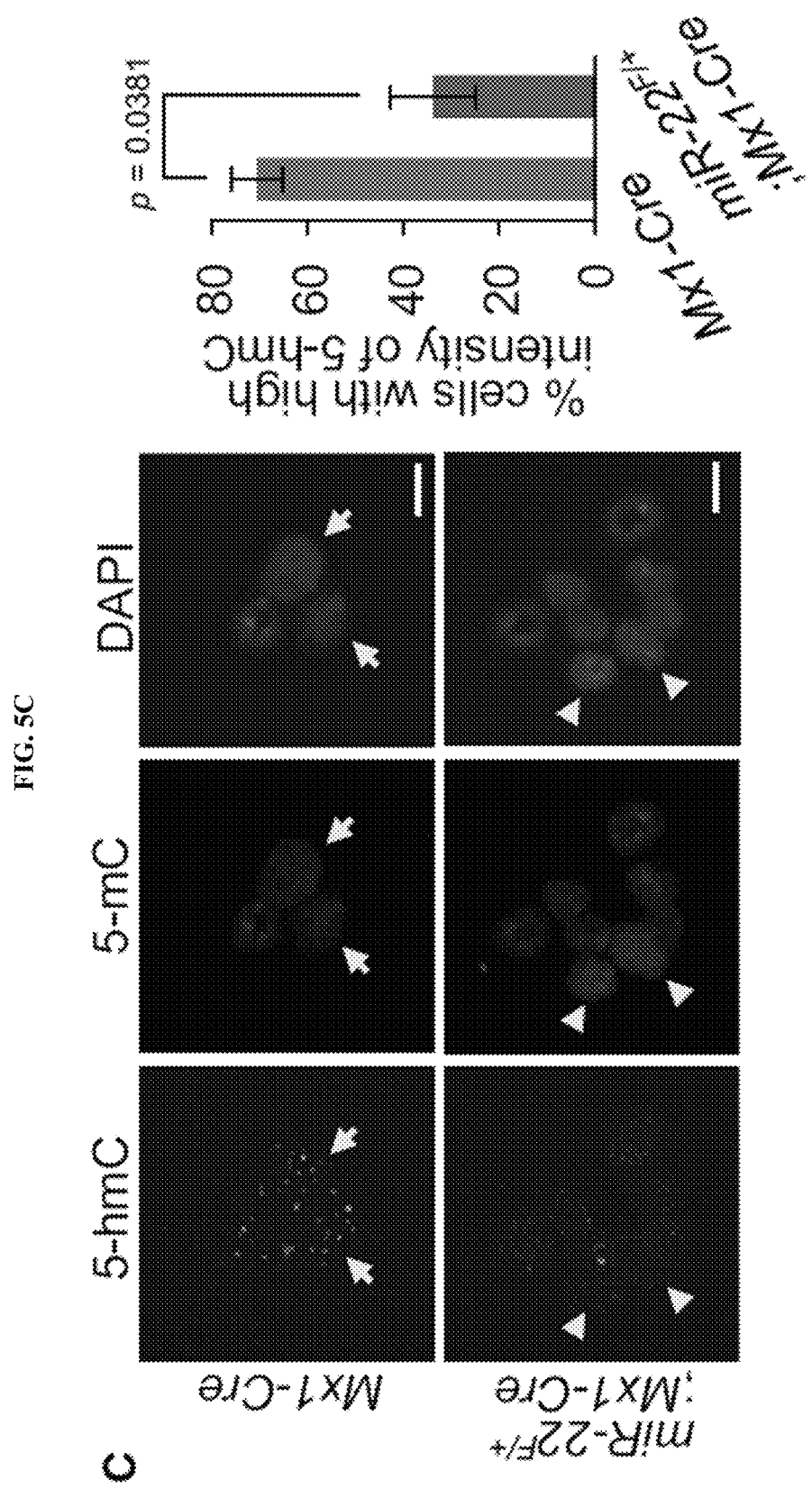
Figure 5D:
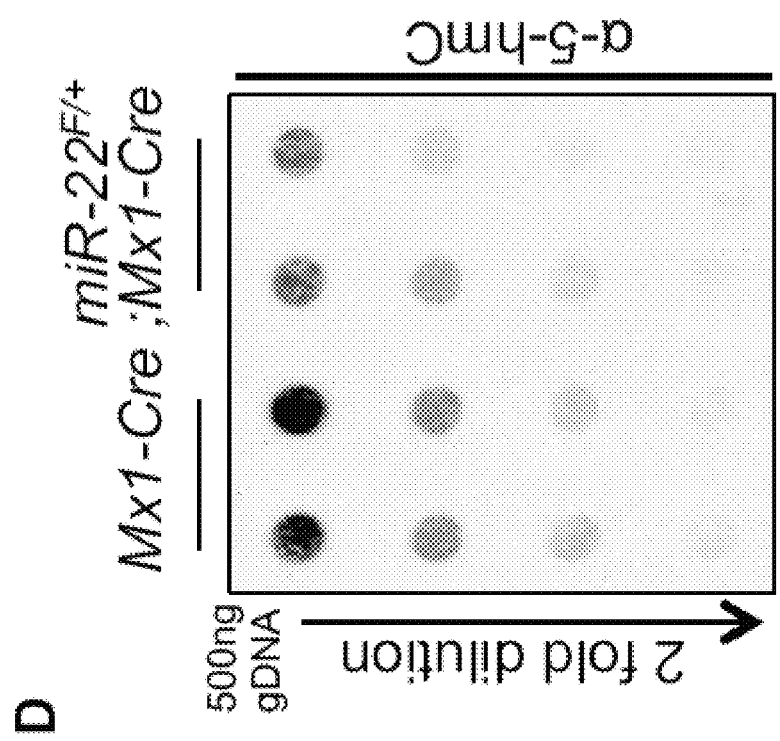
Figure 5E:
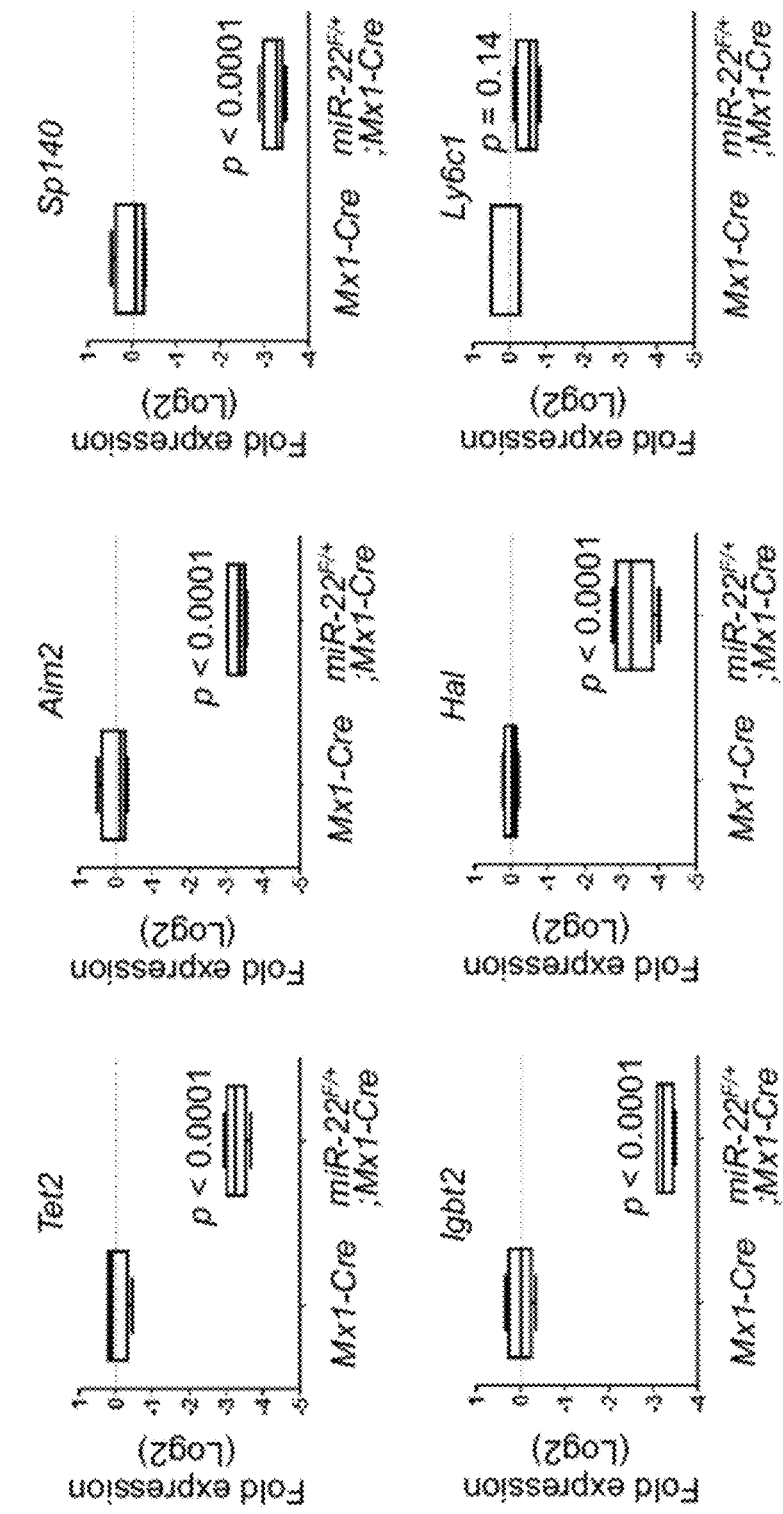
Figure 5F:
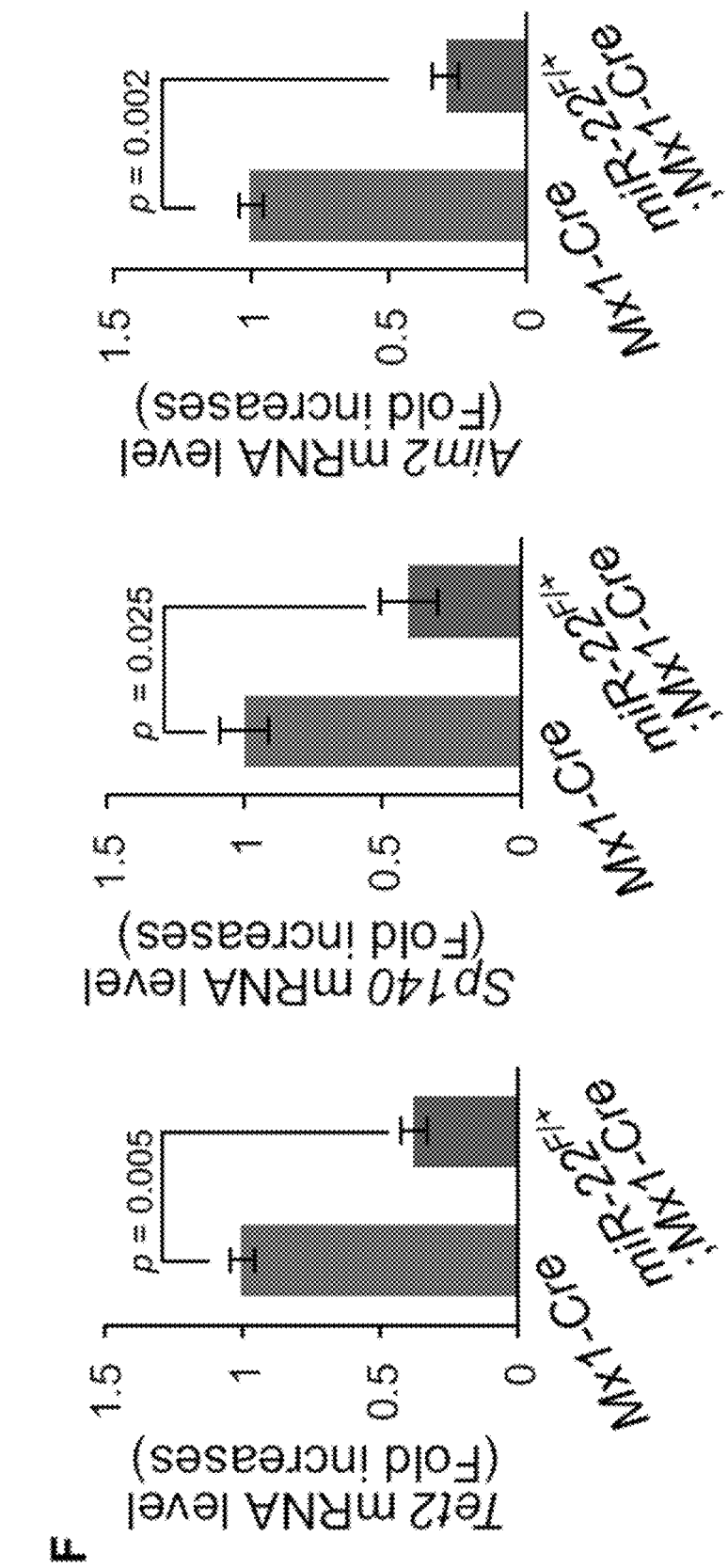
Figure 5G:
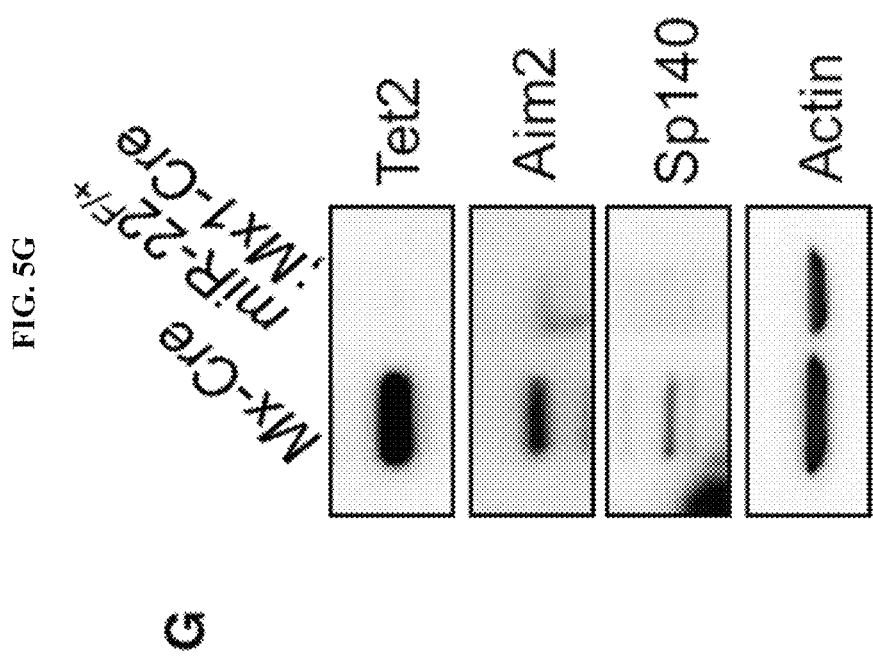

It was then determined whether miR-22-mediated TET2 inactivation is sufficient to impact the global epigenetic landscape in blood cells. 5-hmC and 5-mC levels in the genomic DNA of miR-22F/+;Mxl-Cre mice were analyzed. Immunofluorescence and dot blot analyses revealed a more than 2-fold reduction in 5-hmC levels and a concomitant increase in 5-mC levels in bone marrow of these mice (FIGS. 5C and 5D), suggesting that changes in an important epigenetic mark (e.g., 5-hmC) may contribute to the ability of miR-22 to affect hematopoiesis and leukemogenesis. To further understand the consequences of repression of TET2 by miR-22 in hematopoiesis, the effects of miR-22 overexpression on putative targets of TET2 were examined. A comprehensive real-time qPCR analysis revealed that the expression levels of a substantial number of putative Tet2 target genes, including Aim2, Hal, Igbt2, and Sp140, were markedly decreased in the HSC compartment ($CD150^{pos}CD48^{neg}Flt3^{neg}CD34^{neg}KSL$ cells) purified from miR-22F/+;Mxl-Cre mice (FIG. 5E). Absence in myeloma 2 (AIM2) has a role in the reduction of cell proliferation by cell cycle arrest and is highly methylated in MDS, especially in CMMoL patients with TET2 mutations. Polymorphisms of SP140 (SP140 nuclear body protein) have been found to correlate with chronic lymphoid leukemia, and its hypermethylation has been also demonstrated in CMMoL patients with TET2 mutations, and hence its hypermethylation may influence the risk of leukemogenesis. It was shown that the expression of Aim2 and Sp140 was drastically reduced at the levels of mRNA and protein in the bone marrow of miR-22F/+;Mxl-Cre mice compared to littermate controls, and this reduction was associated with an increase in promoter methylation (FIGS. 5F and 5G). These results suggest that miR-22 represses TET2 expression and thereby can remodel the epigenetic landscape with global changes in 5-hmC levels and alteration in the expression of putative TET2 target genes including AIM2 and SP140.

Example 5: miR-22 Enhances Stem Cell Function and Triggers Hematological Transformation Through Repression of TET2

Figure 6A:
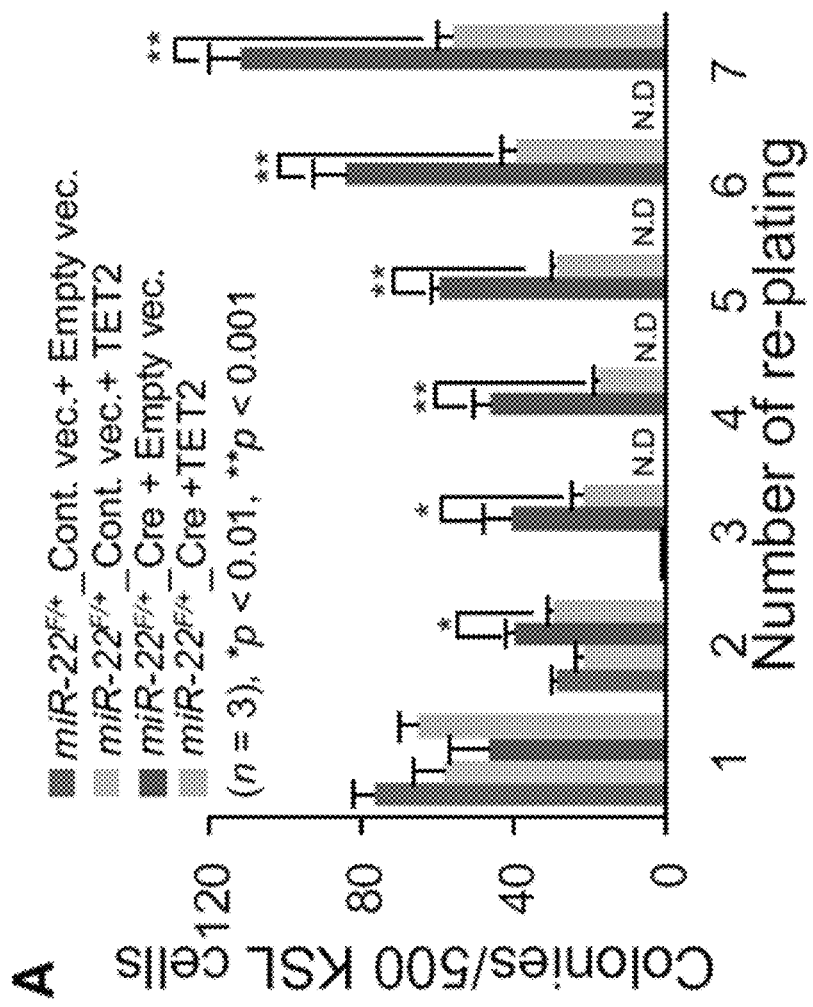
FIGS. 6A-J show that the miR-22/TET2 regulatory network affects HSC function and hematological transformation. All error bars indicate ±SD.
Figure 6B:
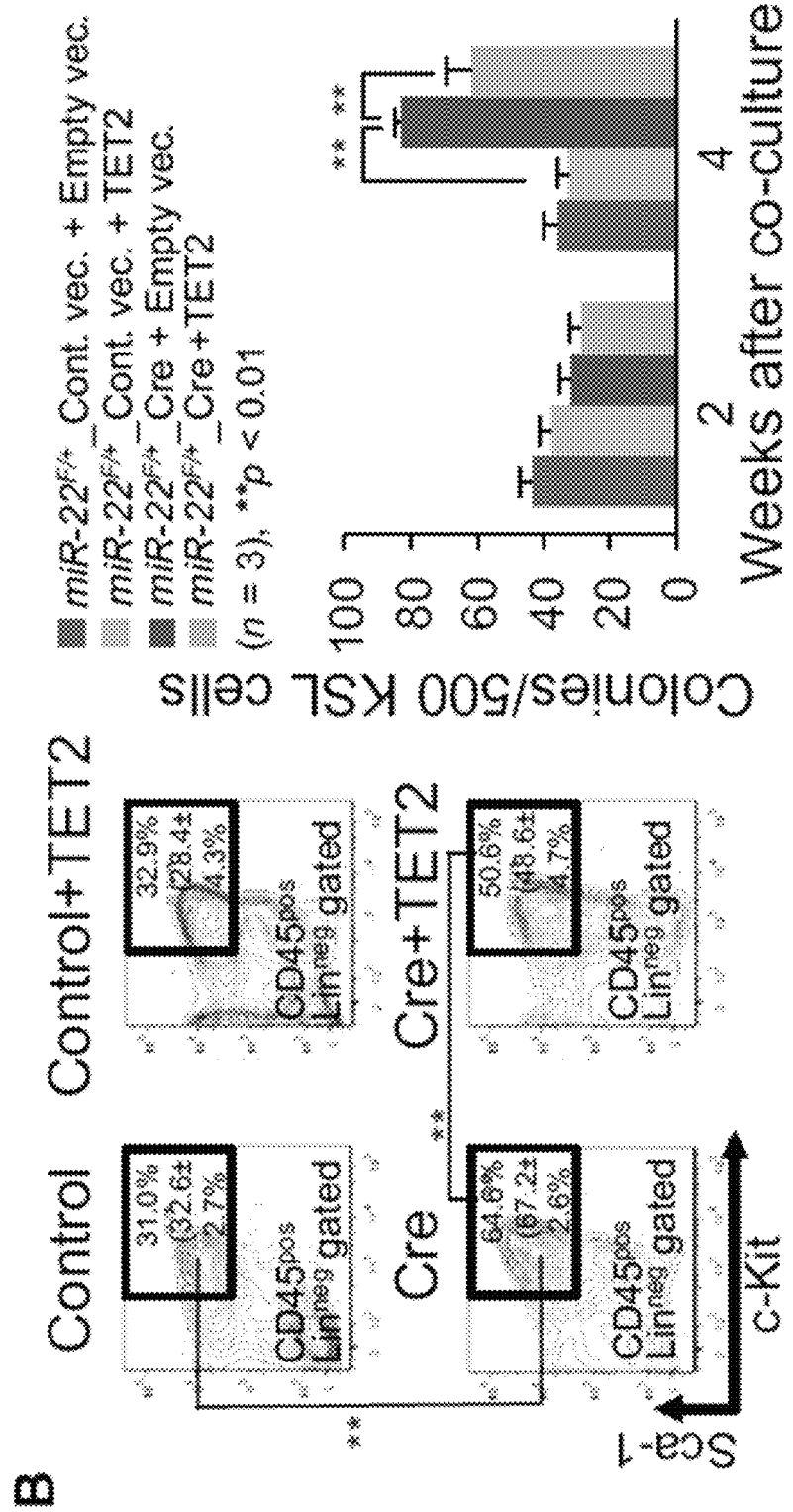
Figure 6C:
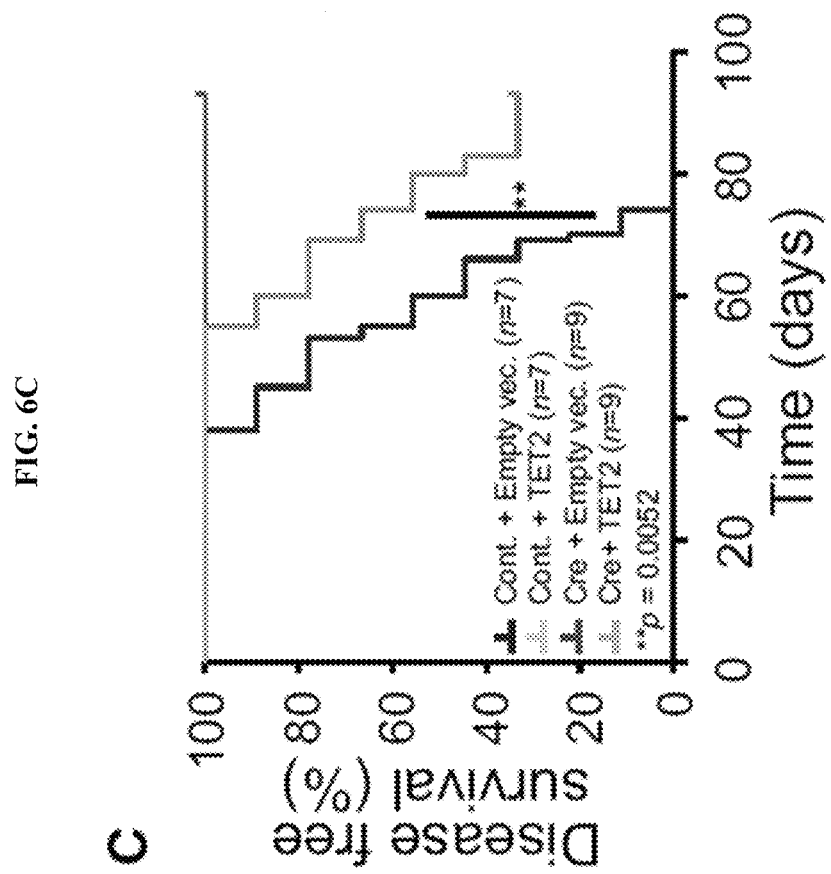

The relevance of the crosstalk between miR-22 and TET2 in hematopoiesis and hematological malignancies was also explored. To test whether TET2 directly contributes to the function of miR-22 in the hematopoietic compartment, KSL cells isolated from wild-type mice were infected with a retroviral vector encoding miR-22 and GFP. After the resorting, GFP+KSL cells were additionally infected with a TET2-expressing lentiviral particle. In vitro colony replating and LTC-IC assays demonstrated that the phenotypes caused by miR-22 overexpression in hematopoietic compartment are potently suppressed by ectopic expression of TET2. Notably, an in vivo transplantation assay revealed that ectopic expression of TET2 leads to survival advantages for recipient mice transplanted with miR-22-expressing KSL cells. To further examine this interaction, KSL cells from miR-22 transgenic mice were purified and infected with a retroviral vector encoding Cre recombinase and GFP. After the resorting of GFP+KSL cells, cells were additionally infected with a TET2-expressing lentiviral particle and the resulting phenotypes were analyzed. In vitro colony replating and LTC-IC analyses demonstrated that the oncogenic function of miR-22 was antagonized by ectopic expression of TET2 (FIGS. 6A and 6B). When KSL cells of miR-22F/+ mice were simultaneously coinfected with a Cre recombinase construct and a TET2-expressing construct, ectopic expression of TET2 more strikingly impaired the replating potential of GFP+KSL cells. In line with these observations, an in vivo transplantation assay revealed significant survival advantages in recipient mice transplanted with miR-22F/+ KSL cells coinfected with Cre and TET2 compared to those with miR-22F/+KSL cells coinfected with Cre and control vector (FIG. 6C). The positive survival effect drawn by ectopic expression of TET2 was more pronounced in secondary transplantation.

Figure 6D:
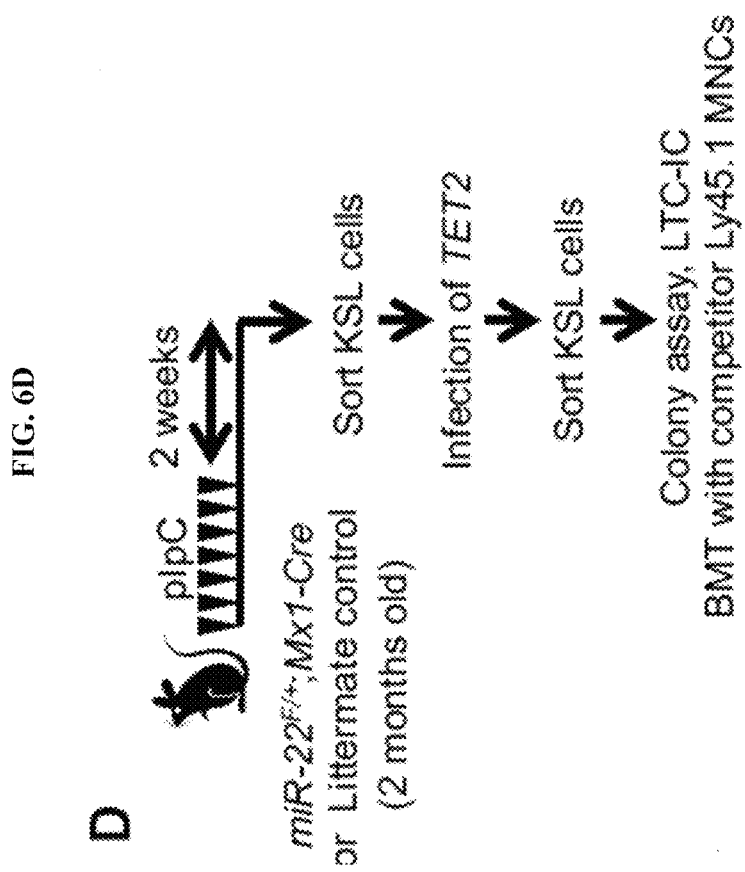
Figure 6E:
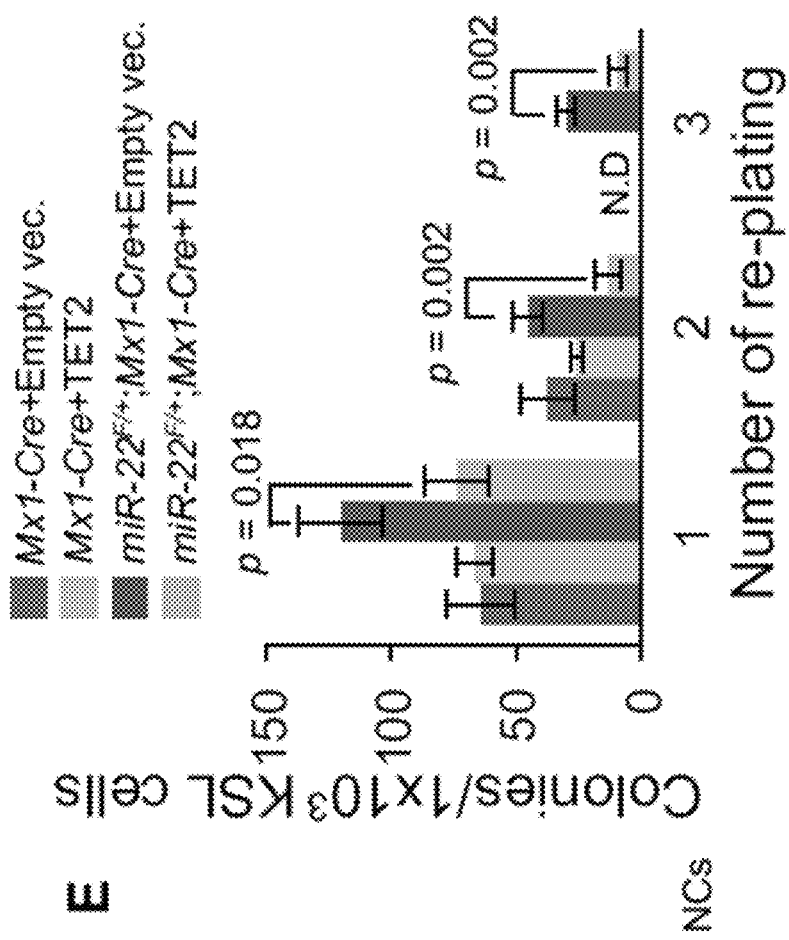
Figure 6F:
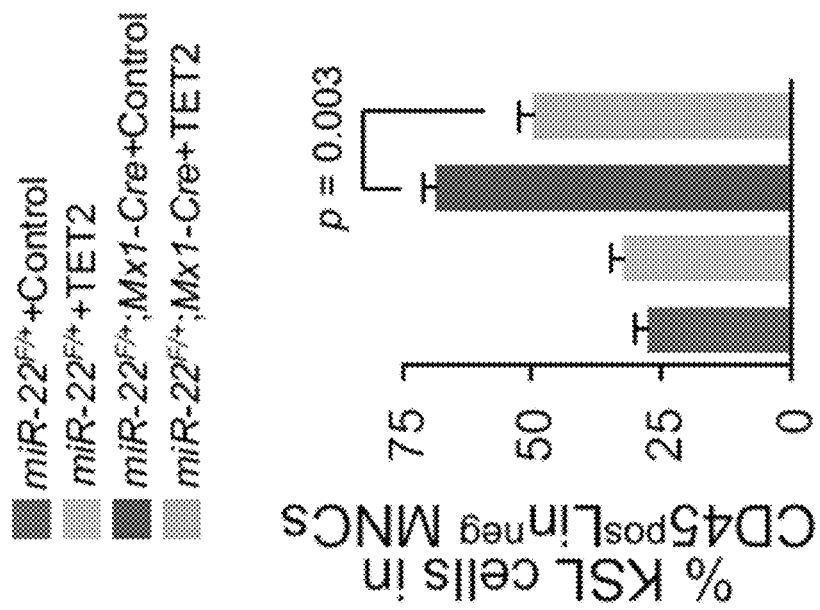
Figure 6F:
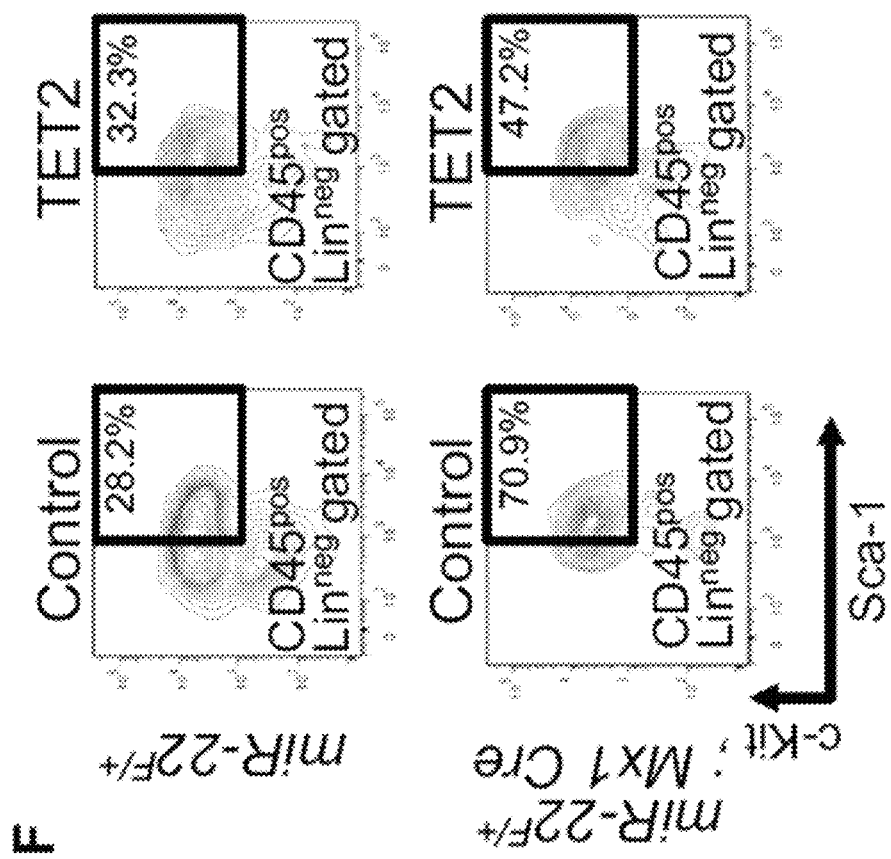
Figure 6G:
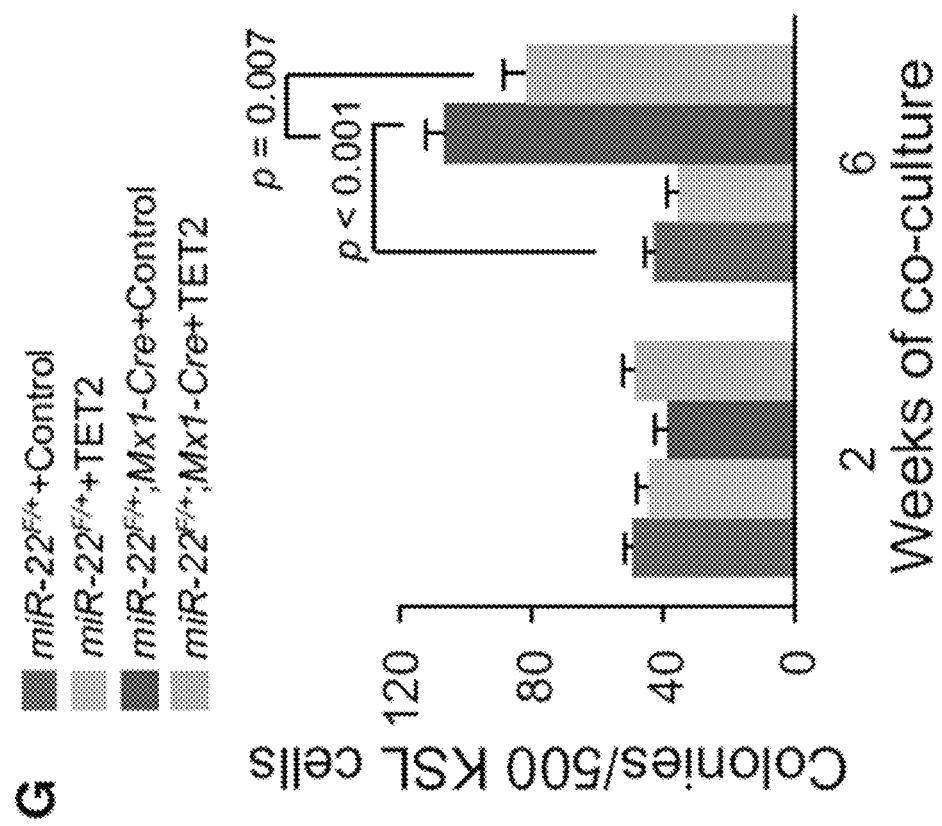
Figure 6H:
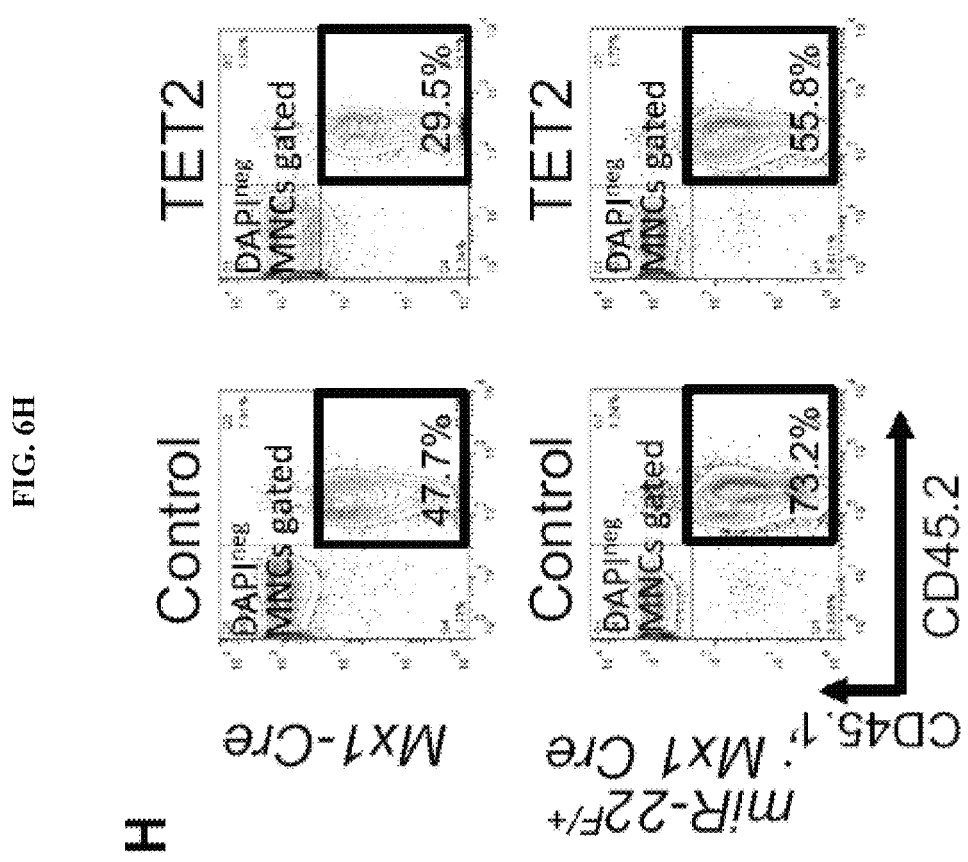

KSL cells from miR-22 transgenic mice after pIpC administration were purified, infected with a TET2-expressing lentiviral particle, and evaluated the resulting phenotypes (FIG. 6D). All the phenotypes elicited by an elevation of miR-22 in vitro and in vivo in hematopoietic compartment, including repression of the expression of Aim2 and Sp140 in bone marrow, were also significantly suppressed by ectopic expression of TET2 (FIGS. 6E-6H). Importantly, KSL cells from primary miR-22 transgenic mice and infected them with TET2 followed by in vivo transplantation together with competitor cells were purified, ectopic expression of TET2 delayed the onset of hematological disorder and was accompanied by significant advantages in disease-free survival. These data suggest that TET2 is one of the major targets responsible for the miR-22 proto-oncogenic function in hematopoiesis and the development of hematological malignancies.

Figure 6I:
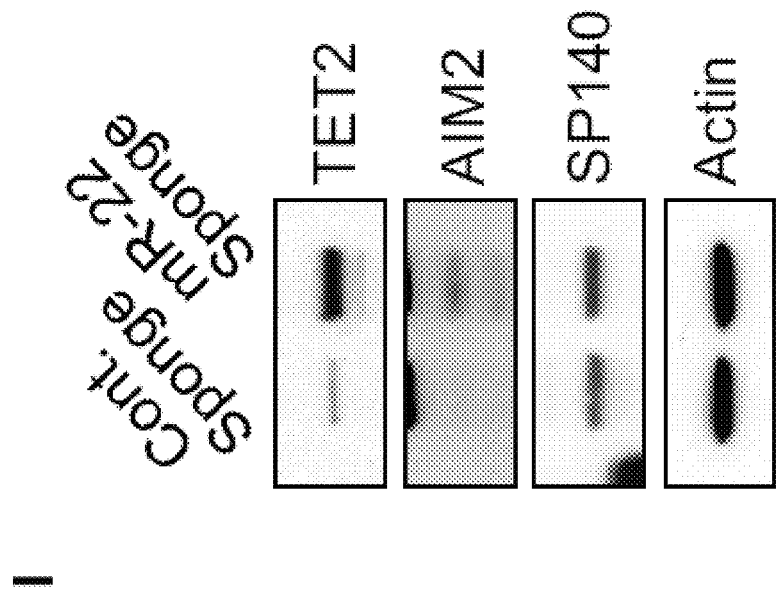
Figure 6J:
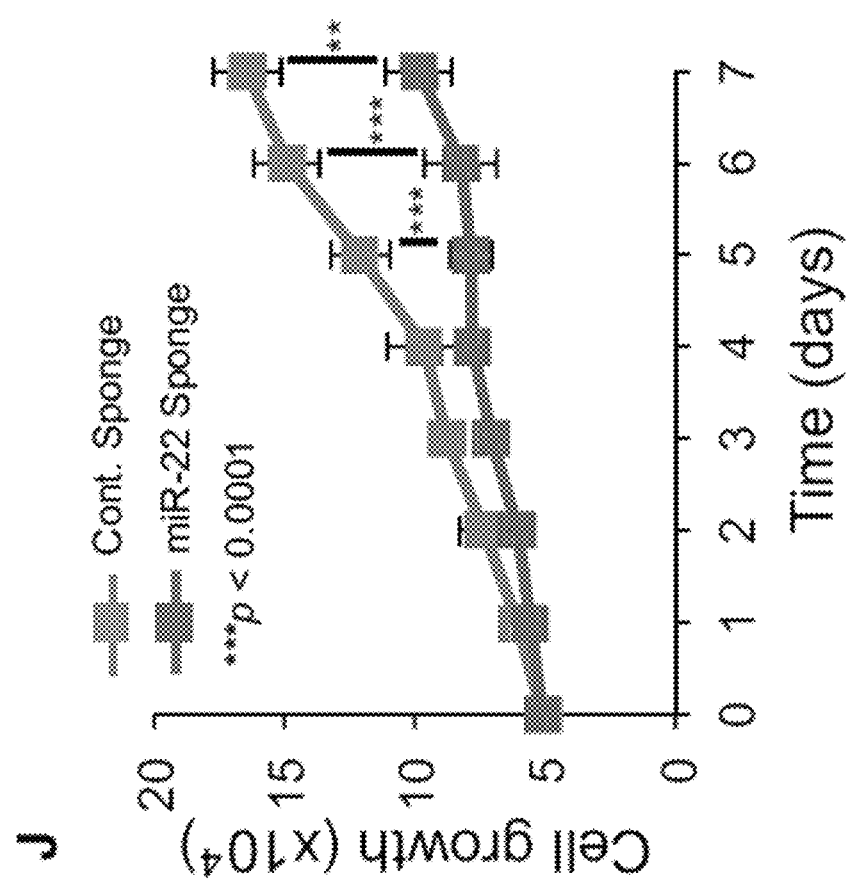
Figure 7A:
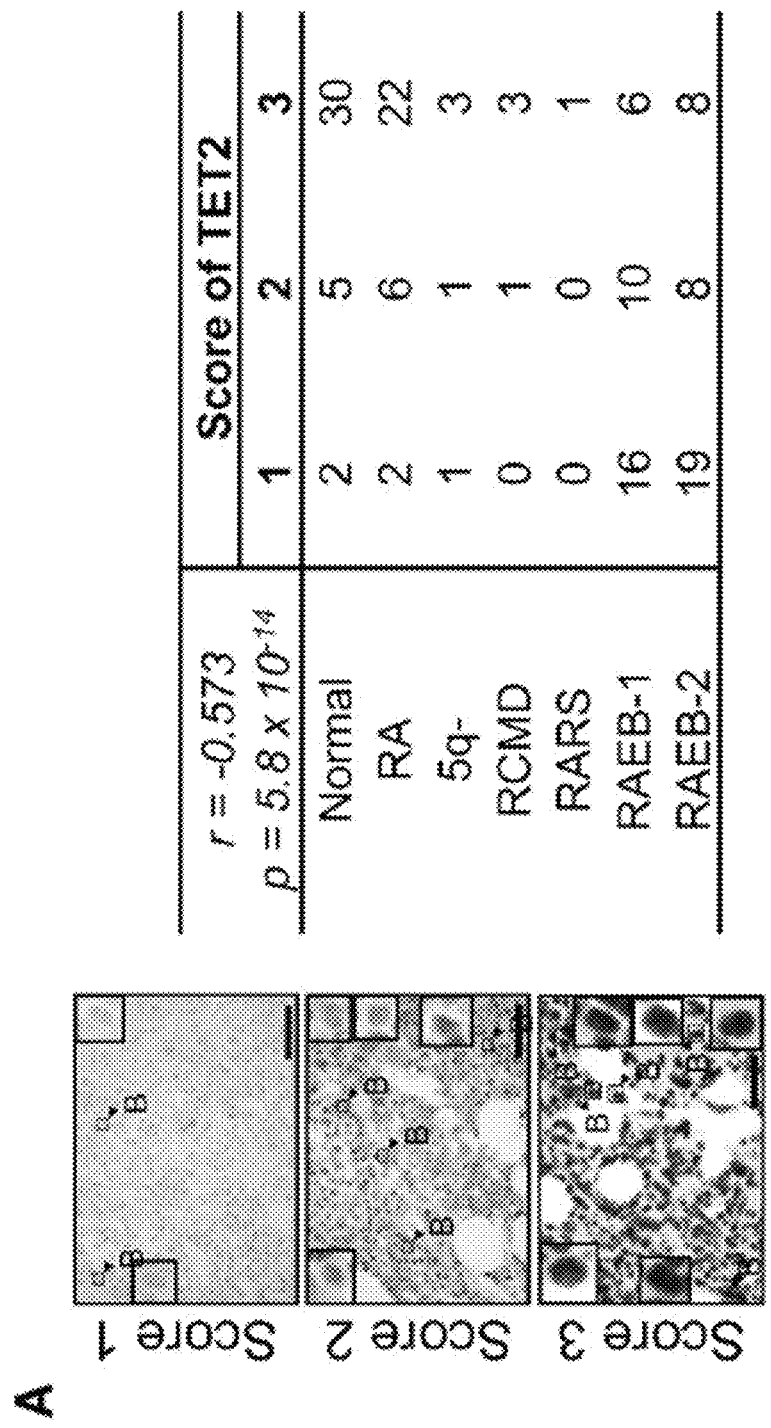
Figure 7B:
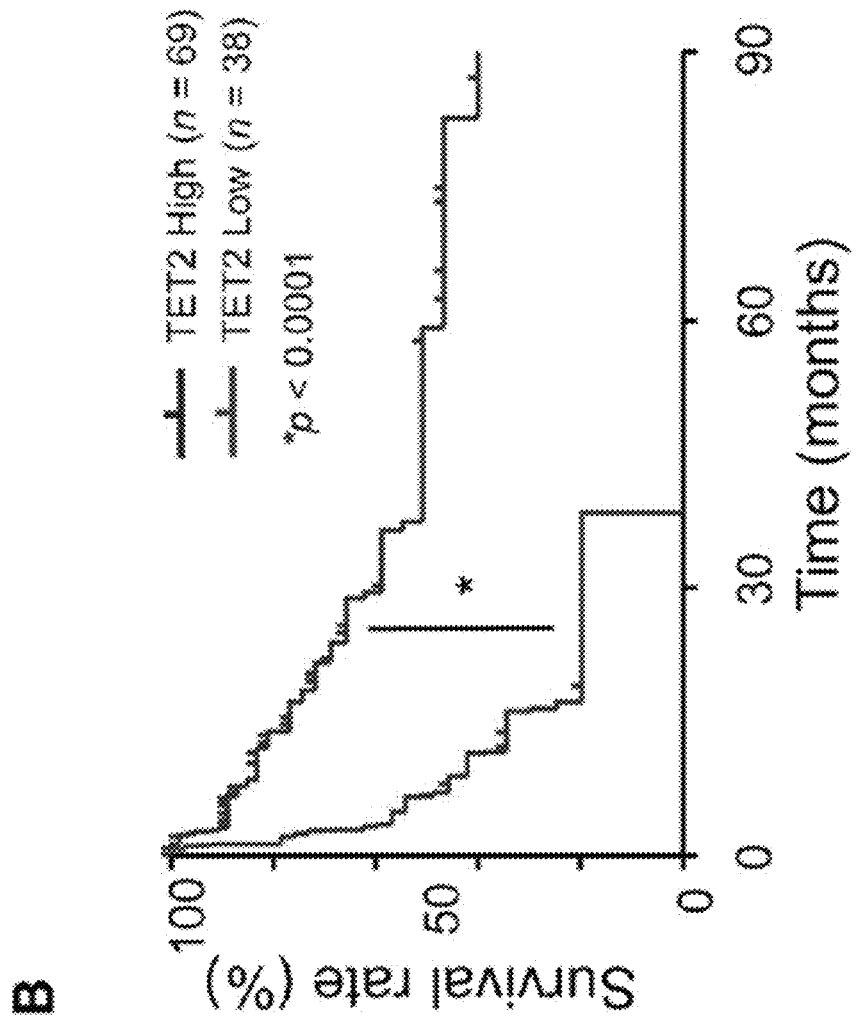
Figure 7C:
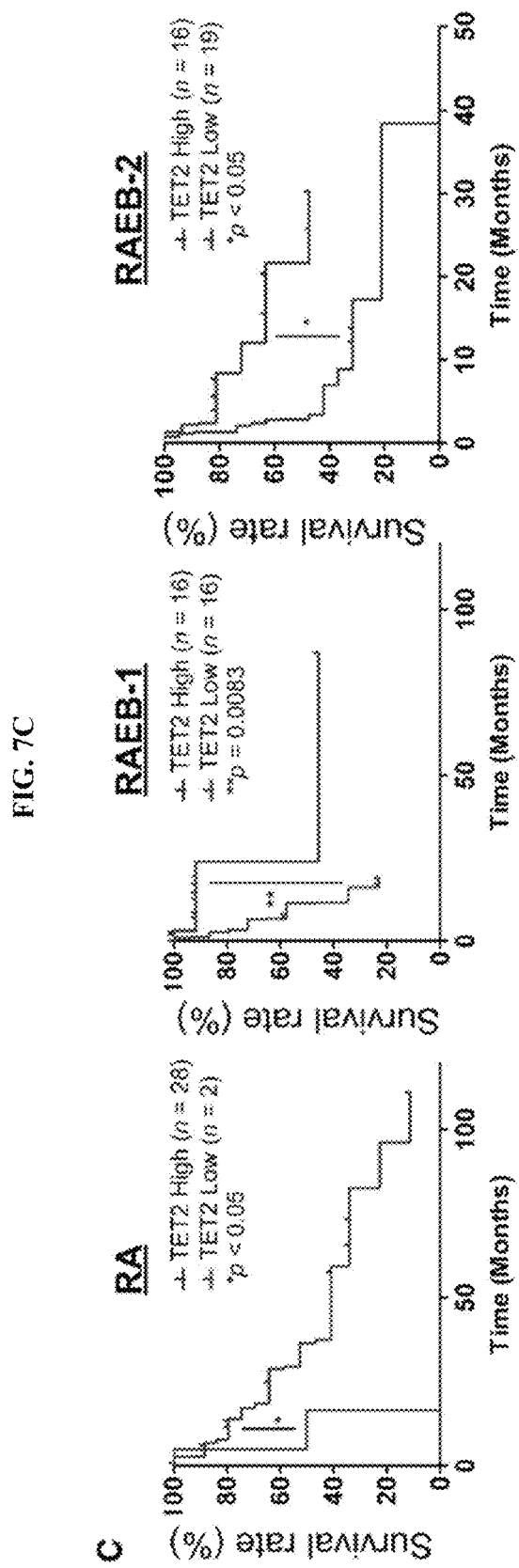
Figure 7F:
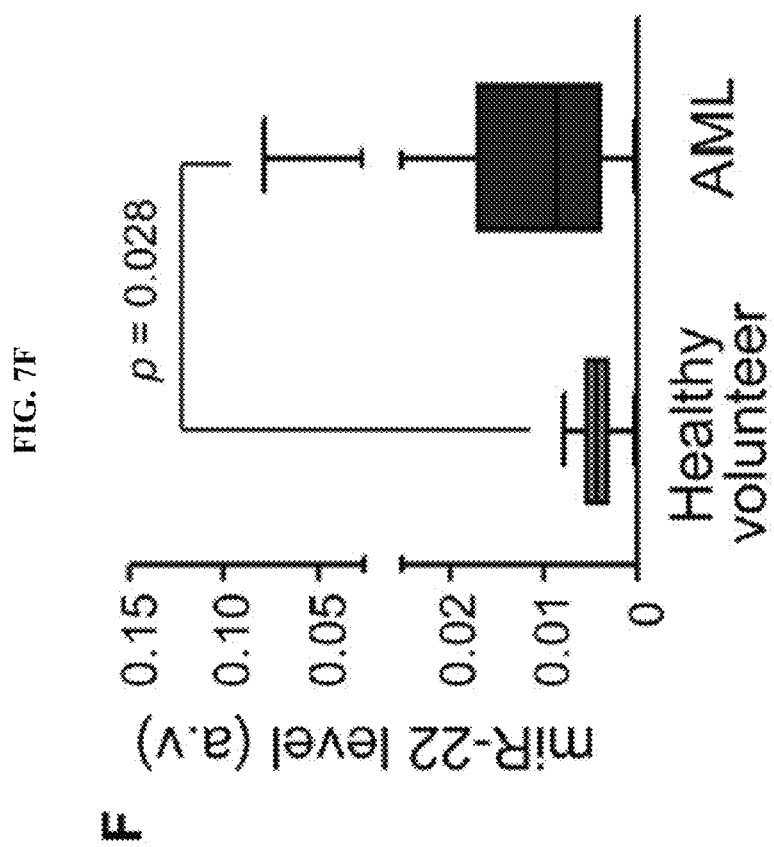
Figure 7G:
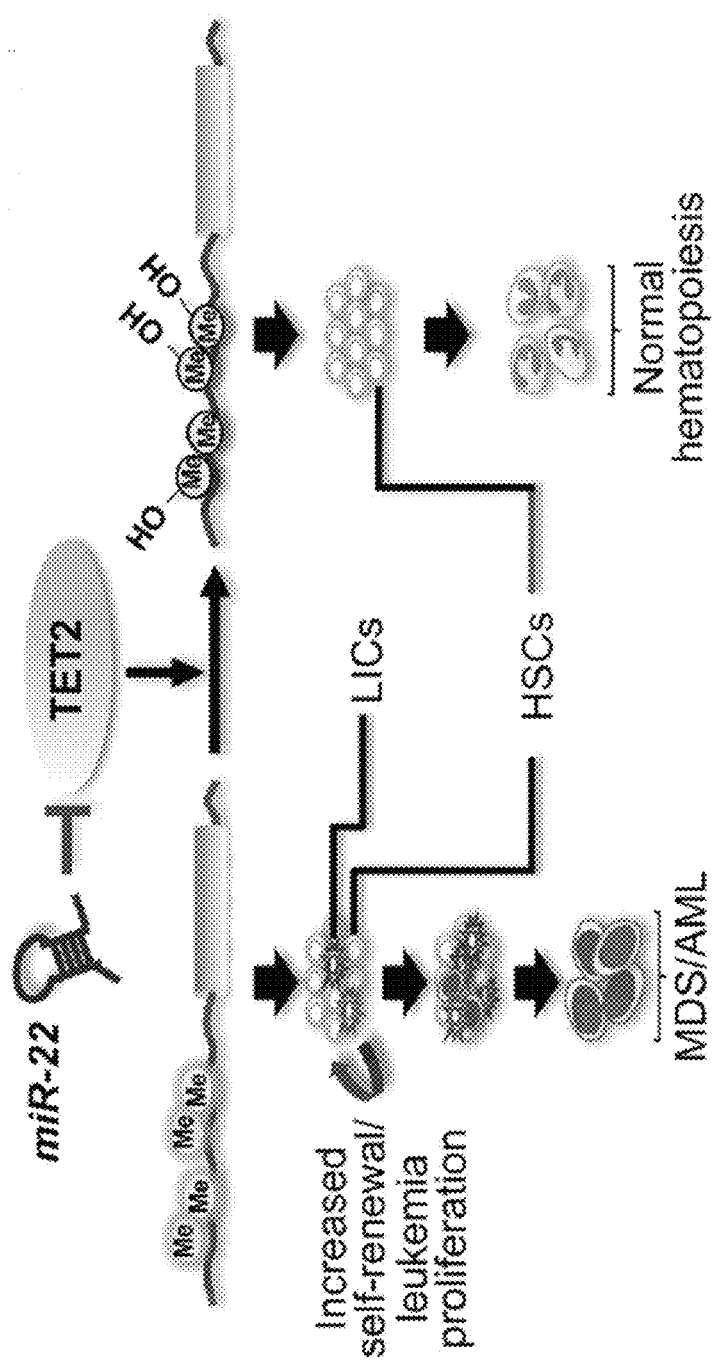

Example 6: miR-22 Decoying Offers Therapeutic Opportunities and its Overexpression Correlates with the Silencing of TET2 Protein in MDS and AML Patients Whether the miR-22/TET2 interaction may offer a therapeutic opportunity for the treatment of hematological malignancies was also explored. Whether inhibition of miR-22 affects TET2 expression and activity, as well as the biology of leukemias was tested. miR-22 in human leukemia cell lines, K562 and U937, both of which express relatively high levels of miR-22 was inhibited by using a miR-22 retroviral sponge or a custom-made locked nucleic acidmiR-22 decoy as the miR-22 sponge. Inhibition of miR-22 in human leukemic cells resulted in a significant reduction in cell proliferation and an elevation of the expression of TET2 and its targets, AIM2 and SP140 (FIGS. 6I and 6J). The U937 cell line harbors phosphatase and tensin homolog (PTEN) mutant with premature termination of coding sequence; hence in this setting the effects observed upon miR-22 decoying are not mediated by the ability of miR-22 to downregulate PTEN expression. In full agreement with these observations, an in vitro colony replating assay revealed that the inhibition of miR-22 by a miR-22 retroviral sponge in KSL cells purified from miR-22 transgenic mice led to a reduction in their colony-forming capability. These data provide a rationale for the therapeutic potential of targeting miR-22 with LNA miR-22 inhibitors in the treatment of hematological malignancies.

miR-22-dependent reduction in the levels of TET2 plays a key role in the development of myeloid malignancies as shown herein. A large cohort of patients with MDS was investigated by an immunohistochemical analysis. This analysis revealed that about 60% of 107 MDS patients analyzed displayed a reduction in the levels of TET2 (36% of 107 MDS patients show Score 1 and 24% show Score 2) and that this reduction was directly correlated with poor survival rates of patients (FIGS. 7A and 7B). A significant correlation was found between TET2 expression and poor survival rates within each WHO classification, as well as among MDS patients harboring a normal karyotype, suggesting that the poorer survival expectancy linked to TET2 downregulation does not simply reflect confounding factors, such as blast count and cytogenetic karyotype (FIG. 7C). These results suggest that the contribution of TET2 to the pathogenesis of hematological malignancies extends far beyond the initial impact of its mutations. Combined in situ hybridization and immunohistochemical analyses revealed that miR-22 expression was directly anti-correlated with the levels of TET2 in a large-cohort data set of MDS patients (n=107) (Pearson's r=−0.47, p=2.4 3 $10^{-7}$): 28% of MDS patients that showed the reduced levels of TET2 (Score 1) also exhibited high miR-22 levels (Score 3) (FIG. 7D; FIG. 1A). Furthermore, because the in vivo analysis demonstrated that miR-22 triggers overt leukemia (FIG. 4G), the miR-22/TET2 interactive relationship in AML with multiple lineage dysplasia (MLD) was investigated (n=18). Combined analyses of in situ hybridization and immunohistochemistry revealed a clear anti-correlation between miR-22 expression and the levels of TET2 (Pearson's r=−0.75, p=2.9 3 $10^{-4}$); in addition, 22.2% of AML with MLD patients showing the reduced levels of TET2 (Score 1) displayed a high expression of miR-22 (Score 3) (FIG. 7E). Western blot and real-time qPCR analyses also corroborated a relationship between miR-22 and TET2 in primary AML patients. Finally, these findings were confirmed by analyzing the expression levels of miR-22 in a very large cohort of AML patients from a previously reported real-time qPCR database (Jongen-Lavrencic et al., MicroRNA expression profiling in relation to the genetic heterogeneity of acute myeloid leukemia. Blood 111, 5078-5085.). Here miR-22 was found highly expressed in 58.1% of 214 AML patient samples compared to normal bone marrow from healthy donors (p=0.028, FIG. 7F). These data strongly suggest that aberration of the miR-22-TET2 regulatory network is one of the common events in hematopoietic malignancies.

Example 7: miR-22 Promotes EMT and Tumor Invasion and Metastasis

Figure 8A:
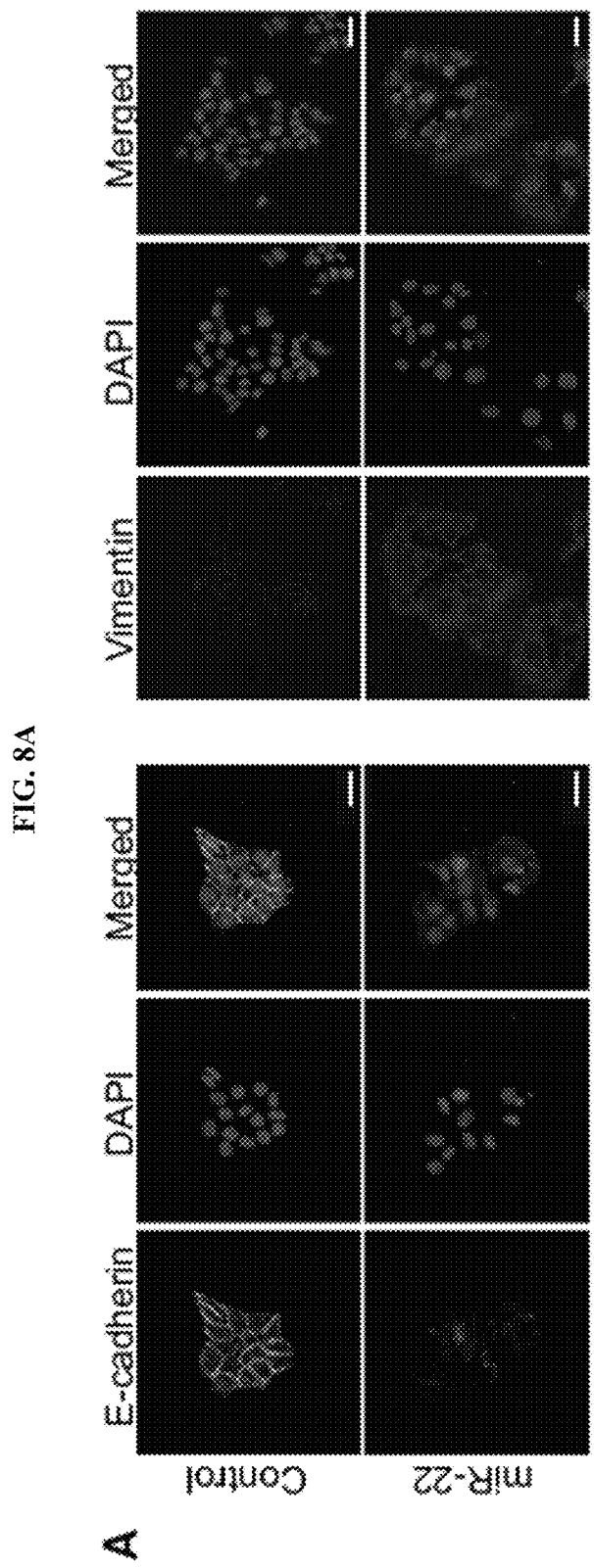

A retroviral vector encoding the human mir-22 gene was transduced into immortalized human breast epithelial cells, HMEC and MCF-10A. It was determined that ectopic expression of miR-22 results in an increased cell motility in an in vitro assay. A dramatic morphological change was also observed in miR-22-overexpressing cells, in which the typical cobblestone-like appearance of normal epithelium was replaced by a spindle-like, fibroblastic morphology. In agreement with these observations, wit was found that miR-22-overexpressing cells displayed a silenced expression of the key epithelial marker E-cadherin, and the upregulations of the mesenchymal markers N-cadherin, Vimentin and Fibronectin (FIGS. 8A and 1B). The epithelial-mesenchymal transition (EMT) is known to be a central mechanism responsible for invasiveness and metastasis of breast cancer and is also associated with normal and malignant mammary stem cell function. miR-22 expression increased the ability of MCF-10A cells to develop into mammosphere structures, suggesting that miR-22 triggers EMT and stemness (FIG. 1C).

Figure 8B:
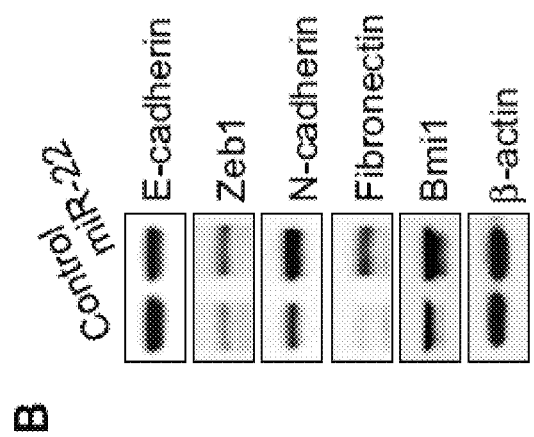
Figure 8C:
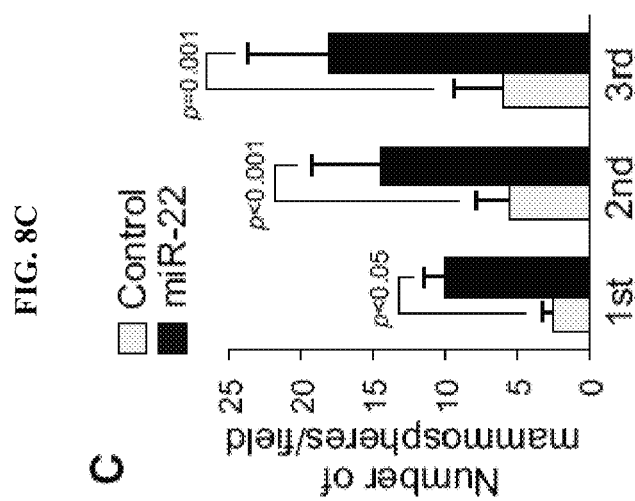
Figure 8E:
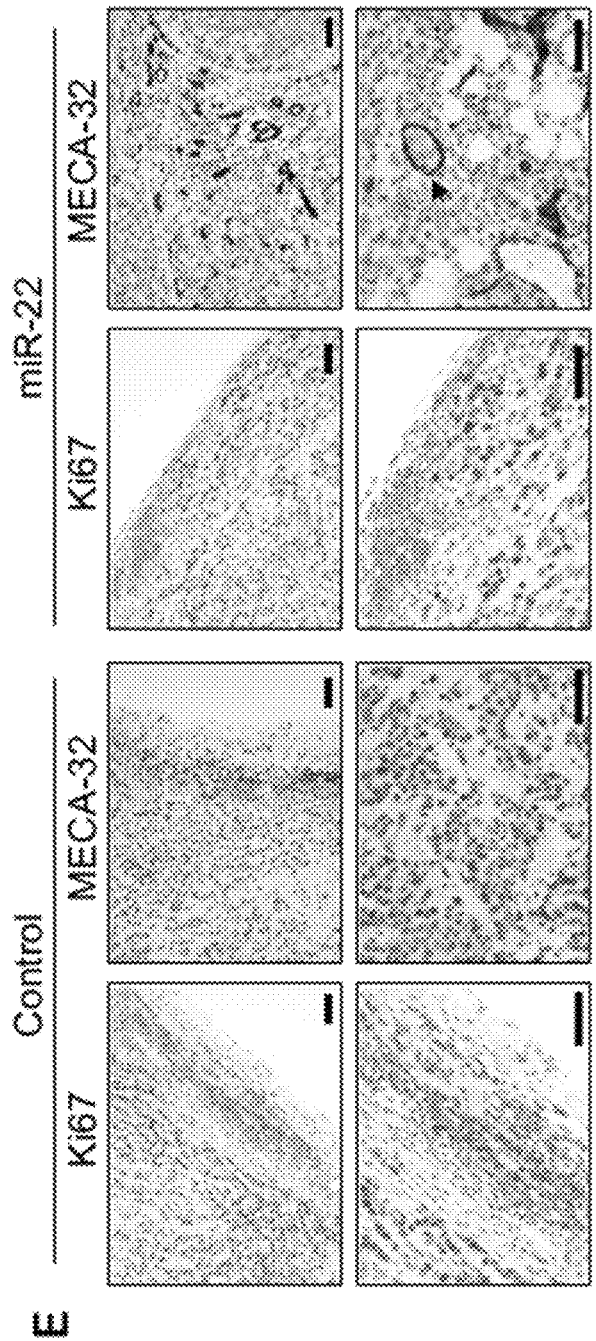
Figure 8F:
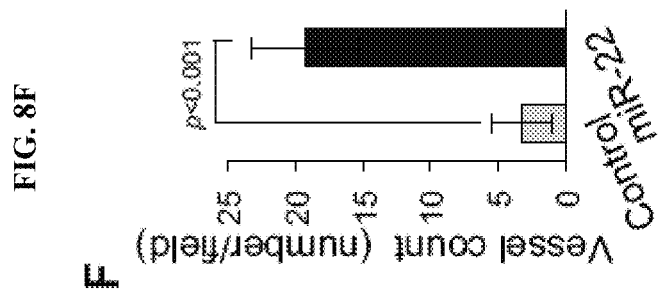
Figure 8G:
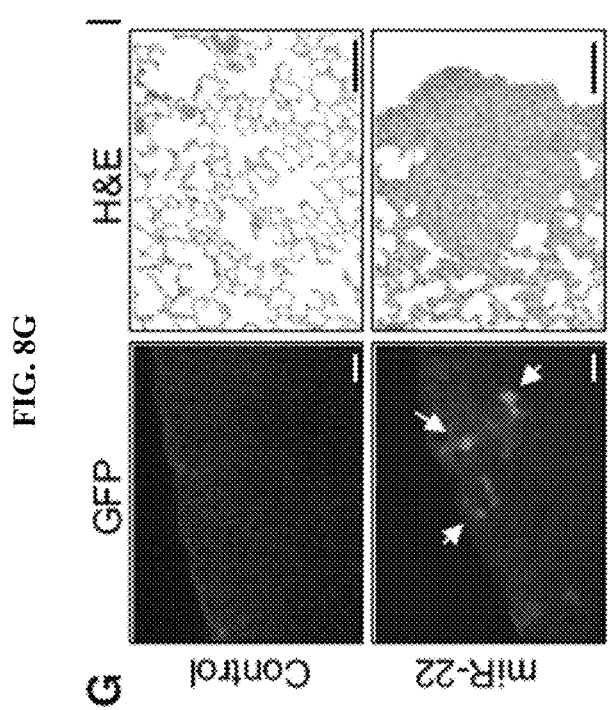

To determine whether miR-22 could induce similar effects in vivo, a xenograft model was established using the non-metastatic breast cancer cell line MCF-7. A miR-22/GFP expressing retroviral vector was used to transduce MCF-7 cells. These cells were implanted into cleared mammary fat pads of Nu/Nu immunodeficient mice. Within three weeks of injection, recipient mice developed macroscopic GFP$^+$ tumors with expansive and infiltrative growth patterns; by 12 weeks, in 2 of 6 cases massive lymphatic invasions were also observed in the adjacent normal breast tissues (FIG. 8D). In comparison, at the same time point, MCF-7 control tumors were strictly non-invasive. The distribution, but not the total number of Ki67$^+$ (proliferating) cells in miR-22-overexpressing tumors, was also distinct from that seen in the control tumors: in the former, large necrotic centers were apparent and Ki67$^+$ cells were enriched in the highly vascularized invasive regions, whereas in the latter the vascularization was poor and the Ki67$^+$ cells were evenly distributed (FIG. 8E). Furthermore, the vessels associated with the invasive regions of miR-22-overexpressing tumors were observed not only in the stroma (peritumoral), but also within the epithelial tumor masses (intratumoral) (FIGS. 8E and 8F).

Figure 8H:
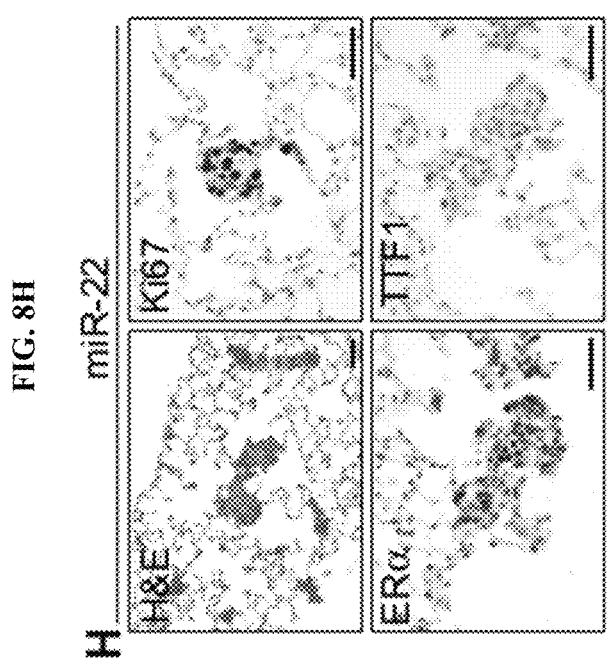
Figure 8I:
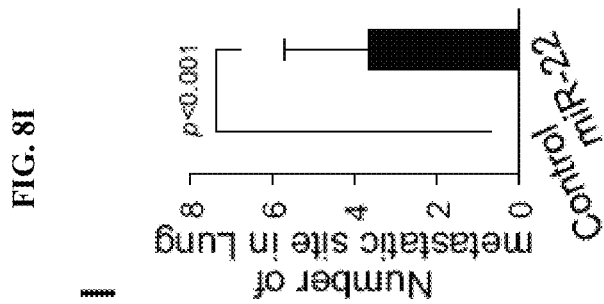

To determine whether miR-22-overexpressing MCF-7 cells could metastasize to distant sites, a detailed pathological analysis of the major organs of our implanted recipients was undertaken. 6 out of 6 mice that received the orthotopic implantation of miR-22-overexpressing cells displayed numerous lung metastases that were readily detectable by both GFP fluorescence and histological analysis (FIG. 1G). These clusters of cells were stained positive for Ki67 and estrogen receptor α (ERα), and negative for thyroid transcription factor 1 (TTF1; a marker of primary lung adenocarcinoma), further confirming their origin (FIG. 8H). In contrast, no metastases were found in control animals (FIG. 8I). Therefore, miR-22 can contribute to cell proliferation, invasion and angiogenesis, and importantly, can impart metastatic properties on otherwise non-metastatic cells.

Figure 9A:
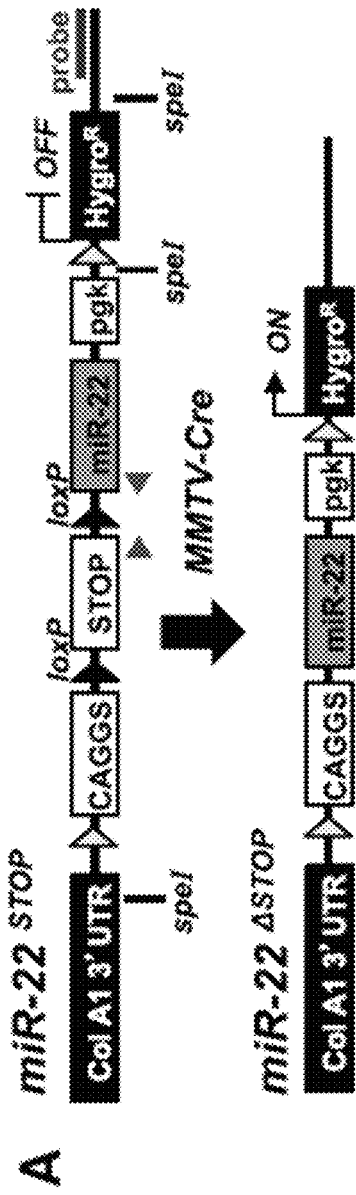
Figure 9C:
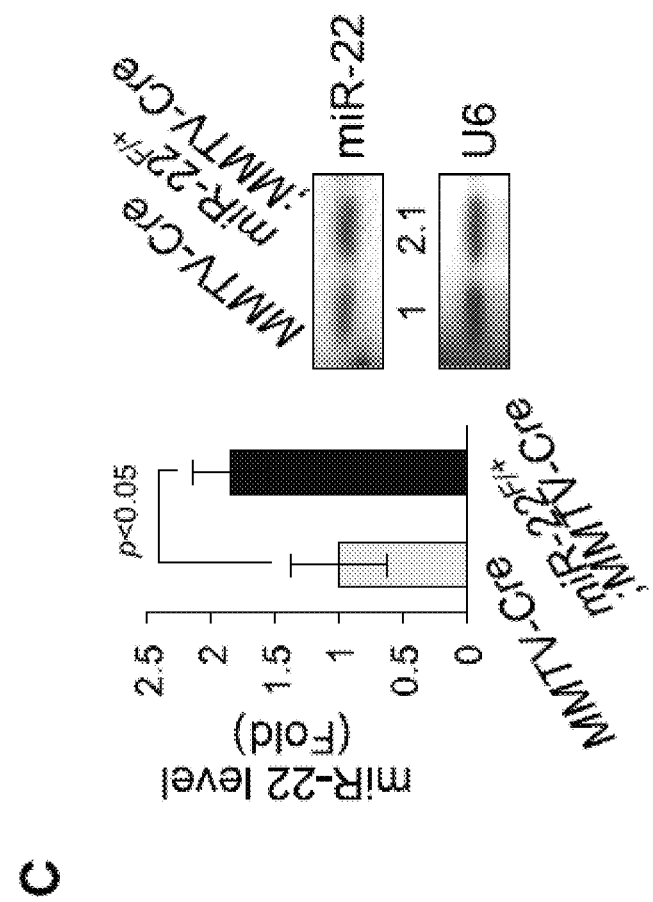

Example 8: miR-22 Increases Mammary Stem Population, and Promotes Tumorigenesis and Metastasis In Vivo in Transgenic Mice Mice that harbored within their Collagen A1 locus the CAGGS promoter and the mir-22 genomic sequence separated by a LoxP flanked transcriptional STOP cassette (hereafter referred to as miR-22$^{F/+}$) were engineered (FIGS. 9A and 9B). By crossing these mice with mice that express the Cre recombinase under the control of the mouse mammary tumor virus promoter (MMTV-Cre), targeted expression of miR-22 in the mammary glands was induced. Real-time quantitative PCR and Northern blot analyses revealed that miR-22 expression was increased 2-3 fold in miR-22$^{F/+}$; MMTV-Cre mice compared to littermate controls (FIG. 9C).

Figure 9D:
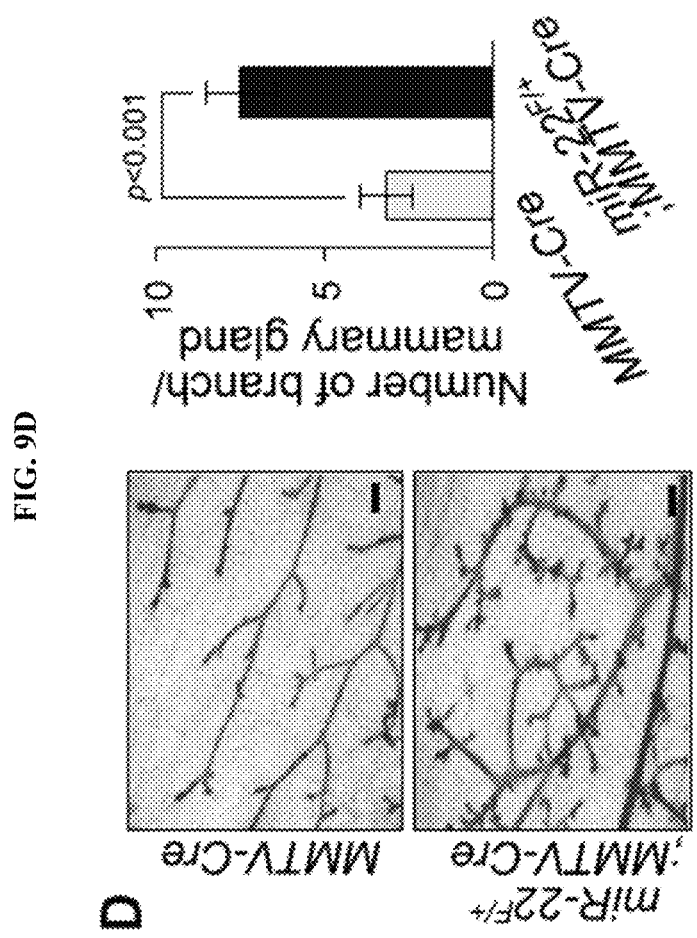
Figure 9E:
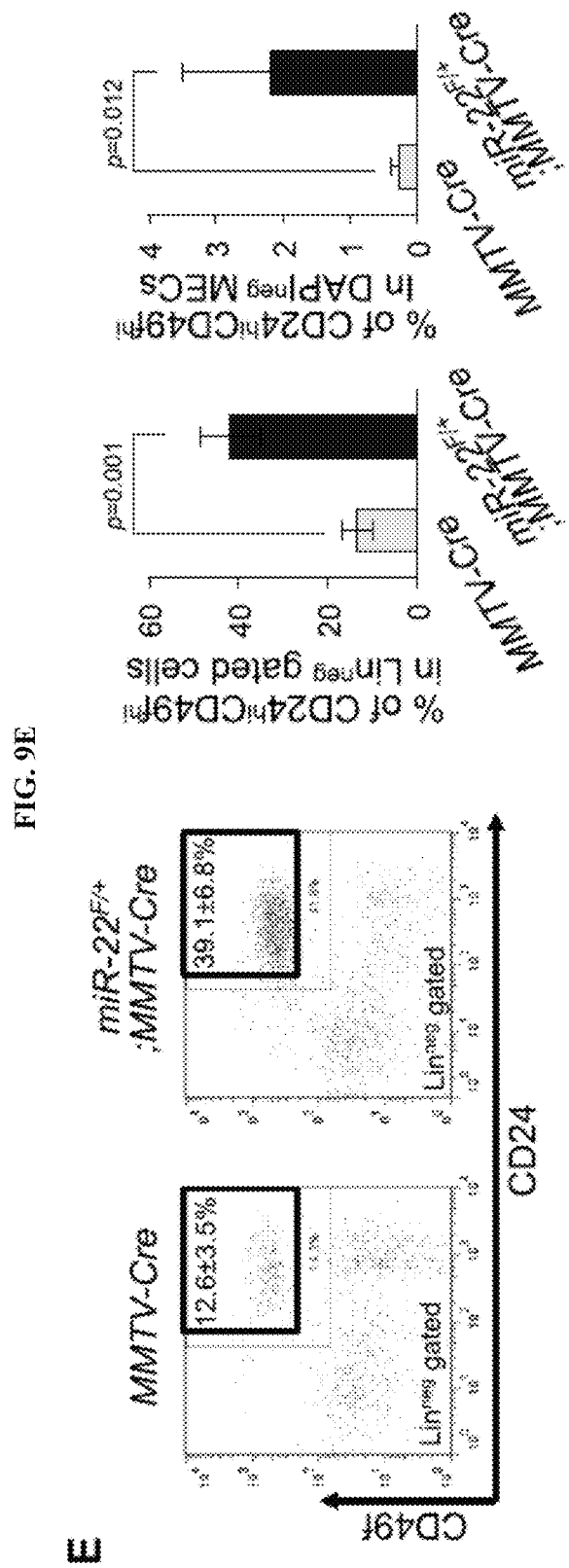
Figure 9F:
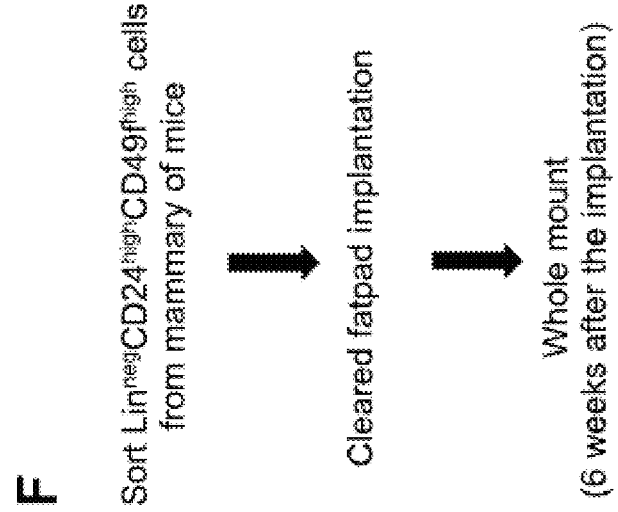

Epithelial cell migration and Western blot analyses in breast epithelium obtained from miR-22$^{F/+}$;MMTV-Cre and control mice revealed a marked increase in EMT features in cells from the transgenic animals at young age. By 7 weeks of age, miR-22 transgenic mice demonstrated an increased ductal side-branching (p<0.001, FIG. 9D), higher numbers of mammary stem cells (MSCs; defined as CD24$^{high}$CD49f$^{high}$) (p=0.001, FIG. 9E), and cells from these mice displayed an increased ability to form mammospheres—three-dimensional structures in culture (p=0.019). Limiting dilution transplantation experiments with CD24$^{high}$CD49f$^{high}$ MSCs revealed that the increase in lobuloalveolar structures in miR-22 transgenic mice directly relates to MSCs, but not to aberrant hormonal signaling during the oestrus cycle (FIGS. 9F and 9G).

Figure 10A:
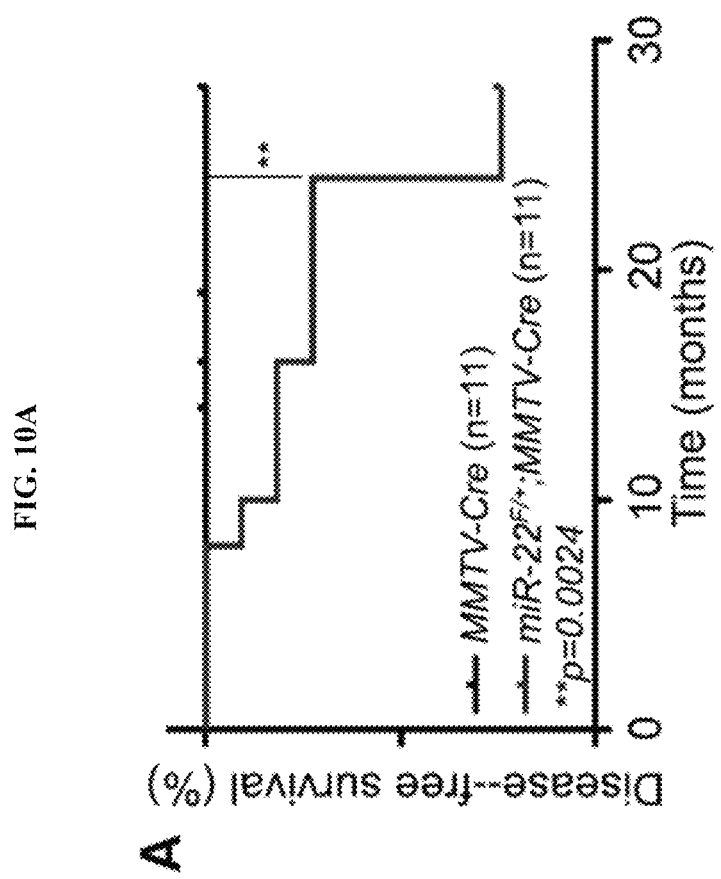
FIGS. 10A-10I show that miR-22 induces mammary tumorigenesis and metastasis in vivo in transgenic mice.
Figure 10B:
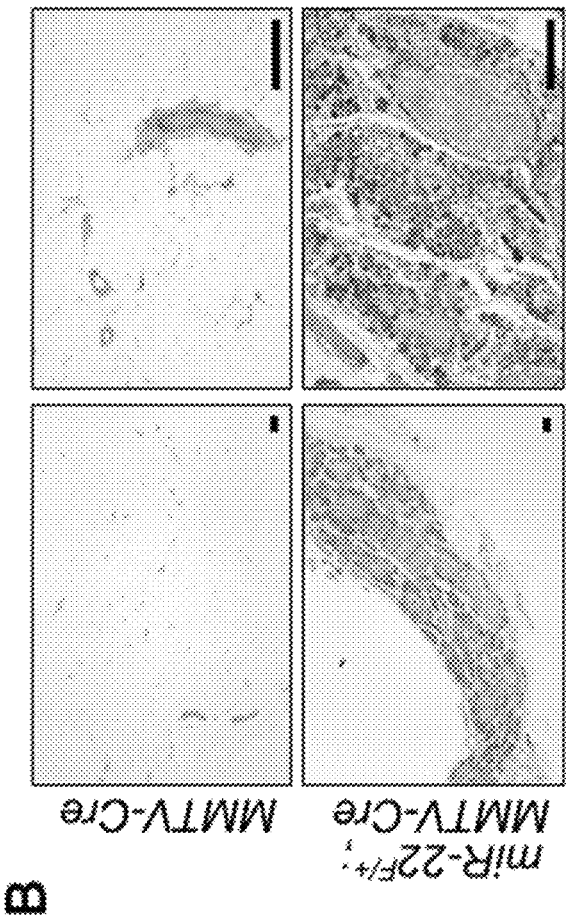
Figure 10C:
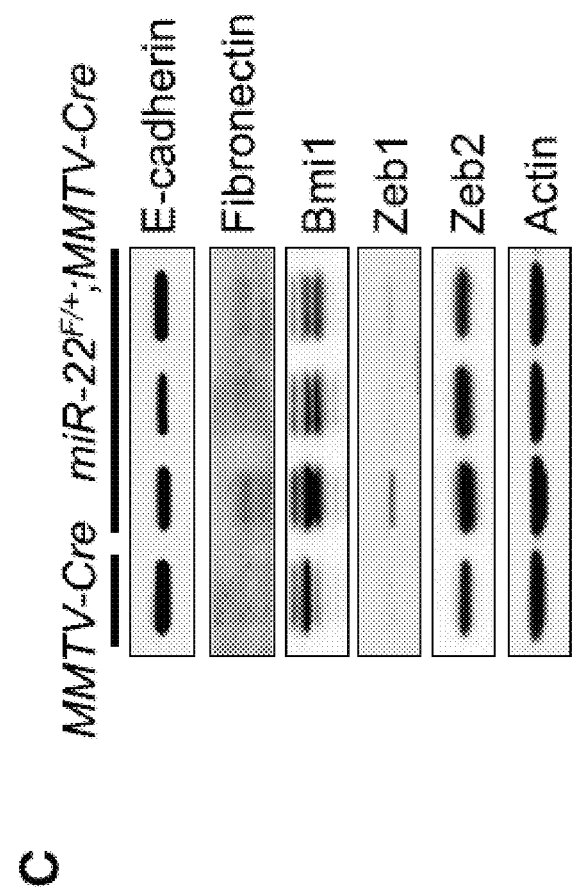
Figure 10D:
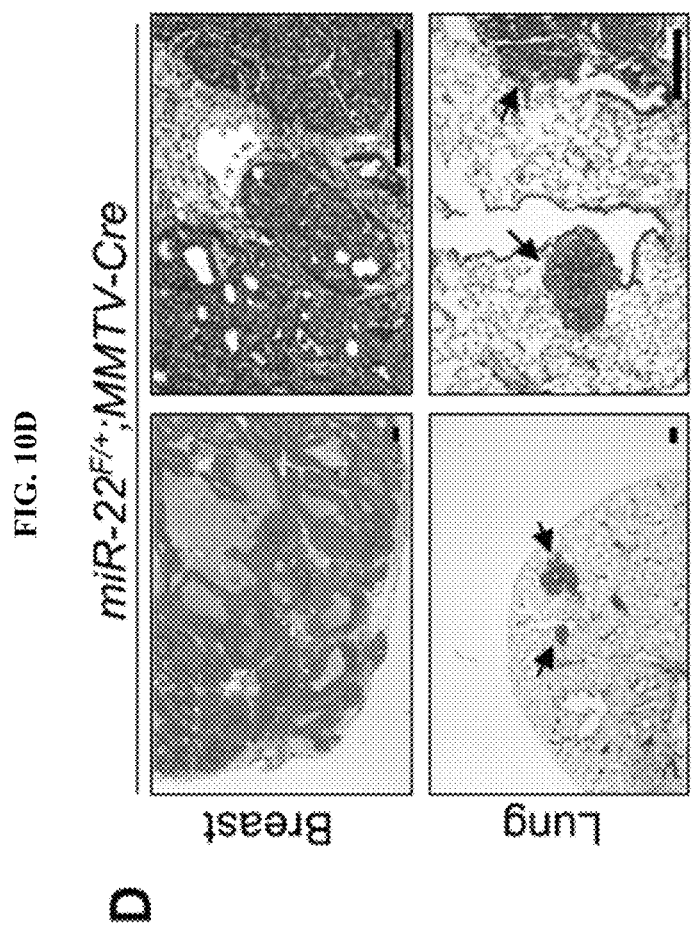
Figure 10E:
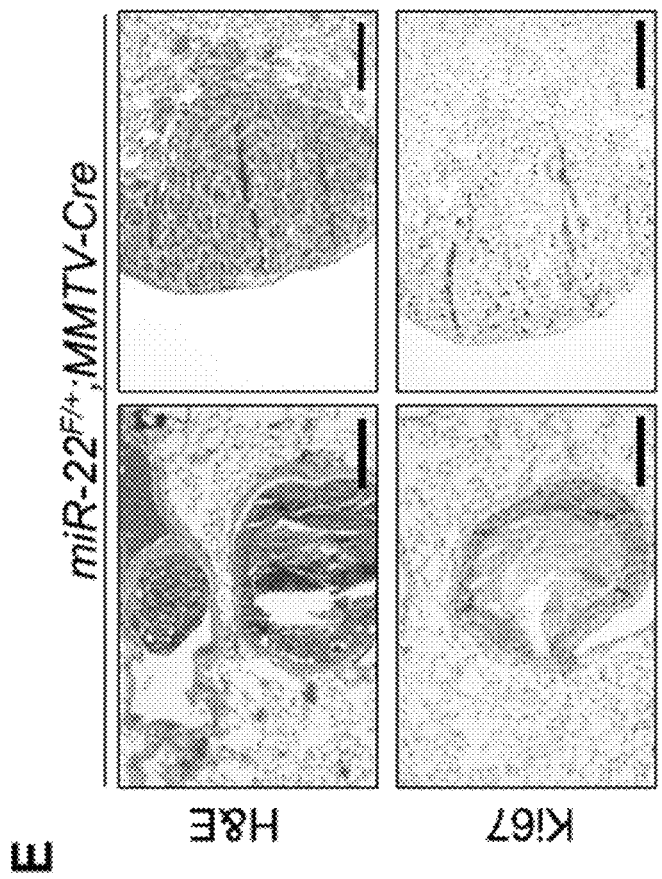

A long-term evaluation of spontaneous mammary tumorigenesis and metastasis in vivo in miR-22 transgenic mice was also performed. miR-22 overexpression in mice resulted in a progressive decrease in the disease-free survival rate at the age of 8-24 months (n=11) (p=0.0024, FIG. 10A). Diffuse alveolar and ductal hyperplasia, focal mammary ductal ectasia, impaction of thick materials, and more importantly, focal ductal carcinomas were observed in virgin female miR-22$^{F/+}$;MMTV-Cre mice (at approximately 60% incidence), whereas neither hyperplasia nor tumor was observed in control mice (FIG. 10B). Noticeably, miR-22$^{F/+}$;MMTV-Cre mice displayed EMT-related breast tumor phenotypes (FIG. 10C) and their primary tumors represented both luminal (cytokeratin 8-positive and cytokeratin 14-negative) and mixed luminal-basal (cytokeratin 8-positive and cytokeratin 14-positive) cell fates. Most strikingly, post-pregnant miR-22$^{F/+}$;MMTV-Cre mice developed lung metastases at 8 to 10 months of age (at 100% incidence) mostly in the peri-bronchiolar lymphatic space (n=3) (FIGS. 10D and 10E).

In addition, by utilizing a series of genetically engineered mouse models, miR-22's promotion of breast cancer and metastasis in vivo was further shown. MMTV-PyVT transgenic mice are known to develop multifocal mammary tumors that spontaneously metastasize to the lung and therefore these mice were first crossed with the miR-22$^{F/+}$;MMTV-Cre mice and an analysis of the resultant compound mutants for development of primary tumors and lung metastases was performed. Although miR-22 overexpression had no significant effect on the development or size of primary mammary gland lesions in this model, the penetrance of metastatic cancer, analyzed at different time points (8 to 12 weeks), was increased in MMTV-PyVTmiR-22$^{F/+}$;MMTV-Cre mice when compared to MMTV-PyVT controls.

Figures 10F, 10G:
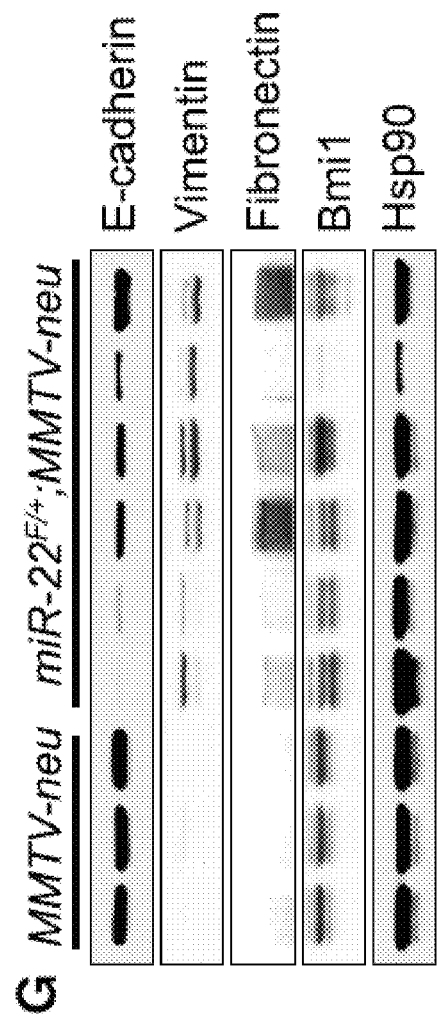
Figure 10H:
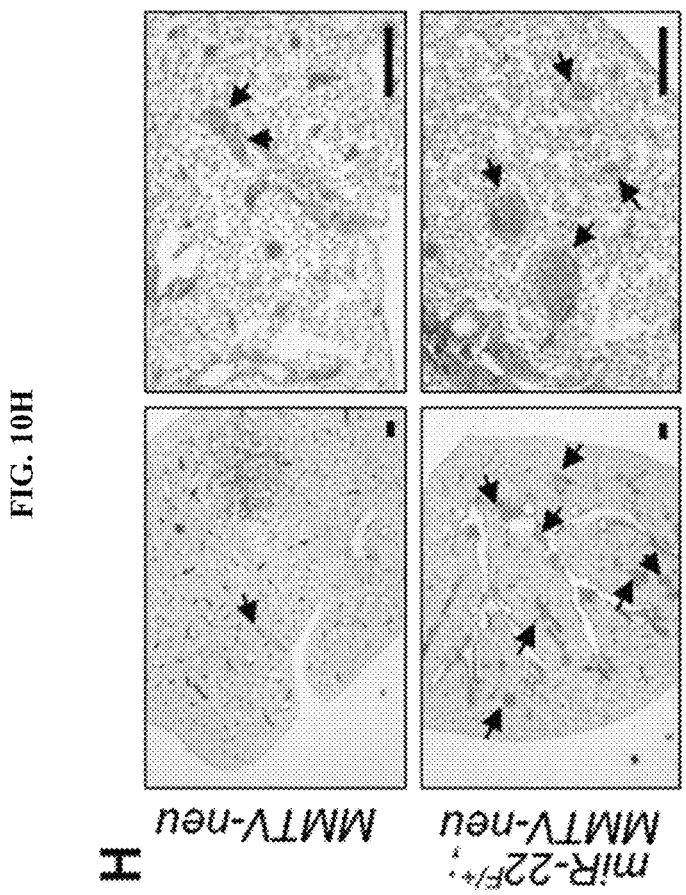
Figure 10I:
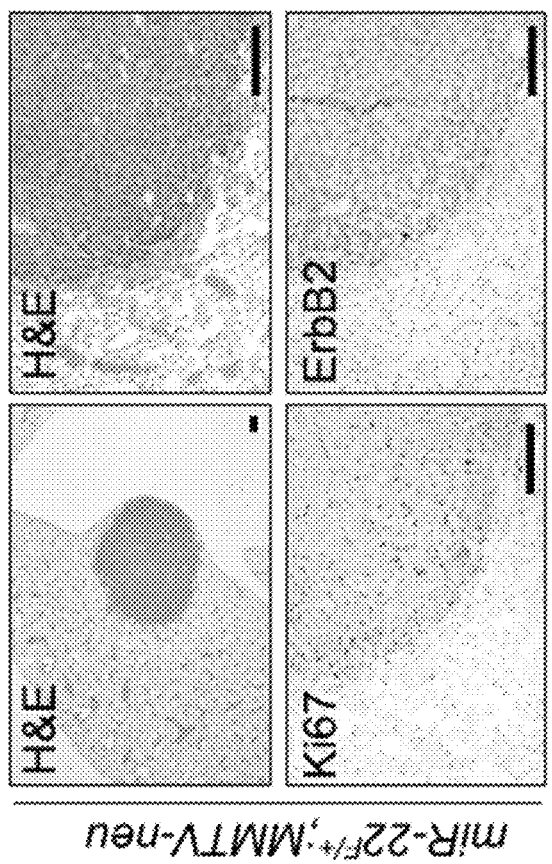

As MMTV-PyVT animals are difficult to compare precisely due to their very early onset of lung metastases, MMTV-neu;miR-22$^{F/+}$;MMTV-Cre mice were next generated and analyzed, taking advantage of the fact that MMTV-neu mice express unactivated neu (c-ErbB2) and show less aggressive mammary tumors and lung metastases. The development of primary mammary gland lesions as well as the incidence of lung metastases was significantly increased in MMTV-neu;miR-22$^{F/+}$;MMTV-Cre mice, by ~19 months of age, when compared to MMTV-neu controls (FIG. 10F). MMTV-neu;miR-22$^{F/+}$;MMTV-Cre mice exhibited EMT-related breast tumor phenotypes (FIG. 10G). A significant number of MMTV-neu;miR-22$^{F/+}$;MMTV-Cre breast tumors were both cytokeratin 8-positive and cytokeratin 14-positive, whereas MMTV-neu control primary tumors were cytokeratin 8-positive and cytokeratin 14-negative, suggesting that miR-22 induces a significant luminal-to-basal cell fate change in breast tumor cells in the presence of neu oncogene insult. MMTV-neu;miR-22$^{F/+}$;MMTV-Cre breast tumors also presented a significant increase in the population of CD24$^{pos}$CD90$^{pos}$ cancer stem cells (CSCs) compared to MMTV-neu control tumors. Finally, the penetrance of metastases to the lung were greatly increased in MMTV-neu;miR-22$^{F/+}$;MMTV-Cre mice when compared to MMTV-neu control mice of the same age (FIGS. 10H and 10I).

These data indicate that miR-22 plays a crucial role in breast stem cell biology, tumorigenesis and metastasis in vivo.

Example 9: miR-22 Triggers Methylation-Dependent Silencing of miR-200

Figure 11A:
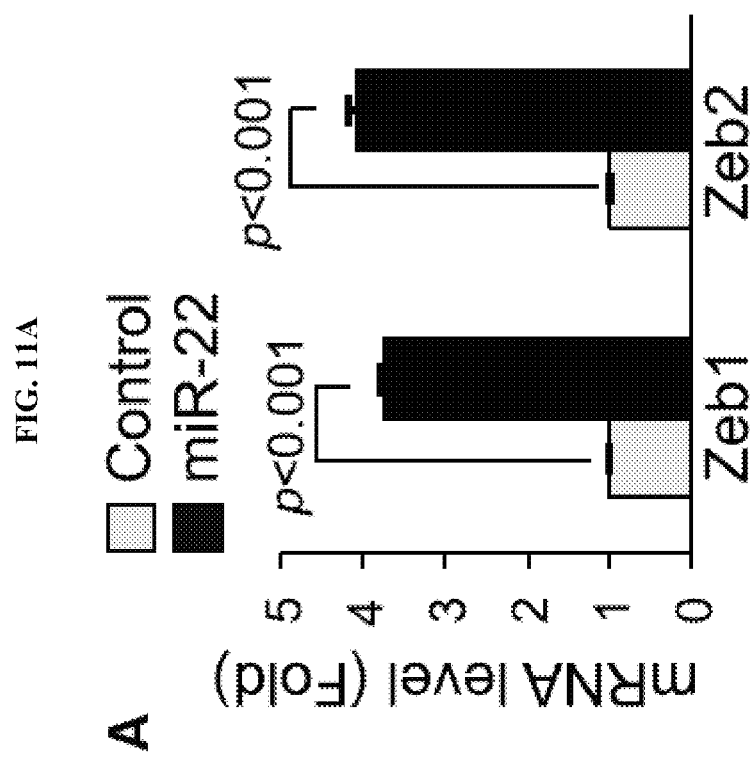
Figure 11B:
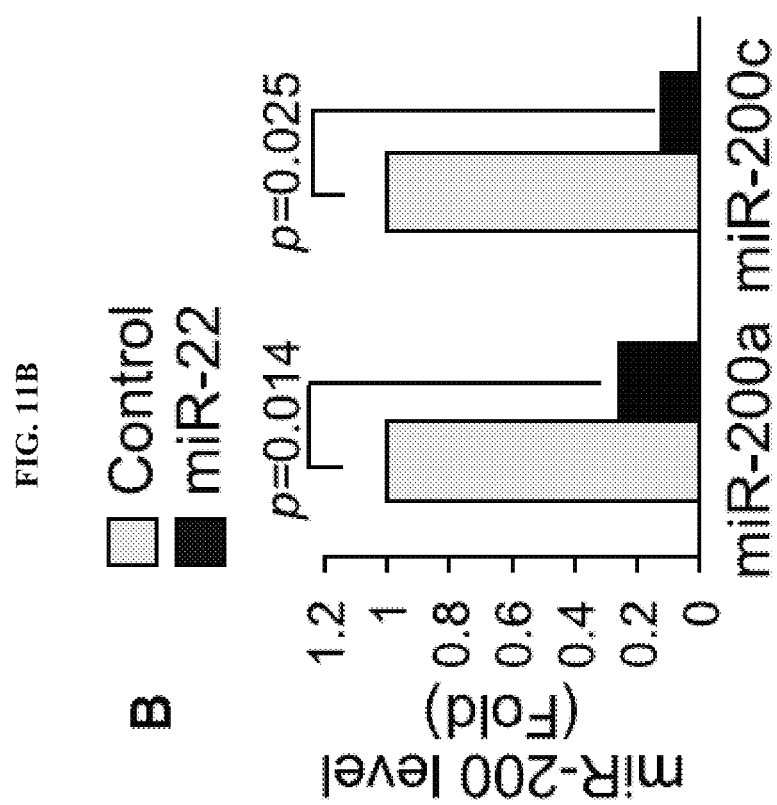
Figure 11C:
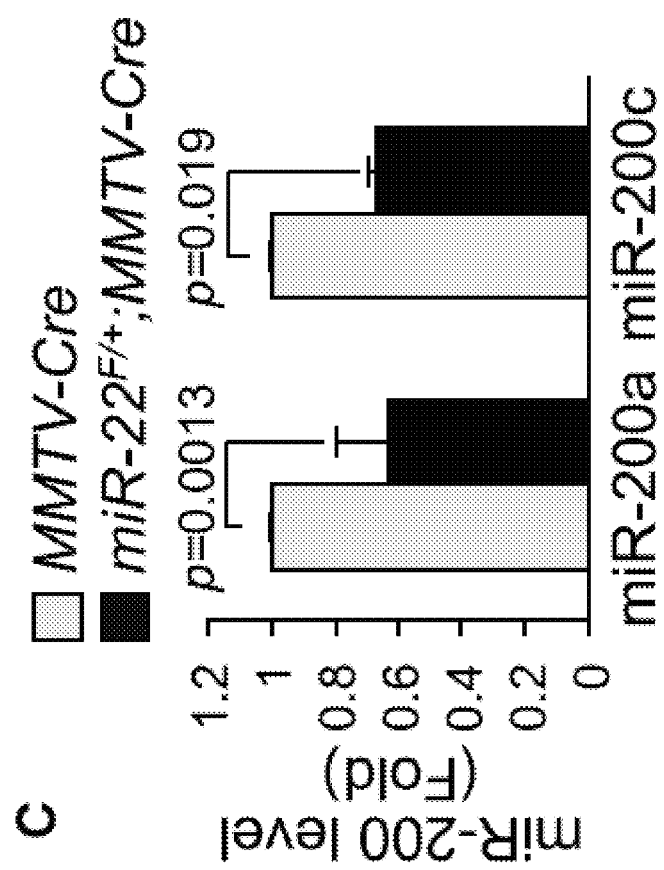

The E-box-binding transcription factors Zeb1 (also known as TCF8 and δEF1) and Zeb2 (also known as ZFXH1B and SMAD-interacting protein 1 [SIP1]), and the miR-200 family members have been shown to regulate EMT in multiple cancer types. Zeb1 and Zeb2 are key transcriptional repressors of E-cadherin, while the miR-200 family is known as important regulators of both EMT and mammary stem cell function through direct targeting of the mRNA of both Zeb1/Zeb2 and Bmi1. It is shown herein that miR-22 is able to repress miR-200a and miR-200c expression, leading to upregulation of Zeb1, Zeb2 and Bmi1 in both human breast epithelial cells and mouse mammary epithelium prepared from miR-22$^{F/+}$;MMTV-Cre mice (FIG. 8B; FIGS. 11A-11C). Taken together, these data suggest that in mammary epithelial cells miR-22 induces EMT and stemness by suppressing the expression of miR-200 family.

Figure 11D:
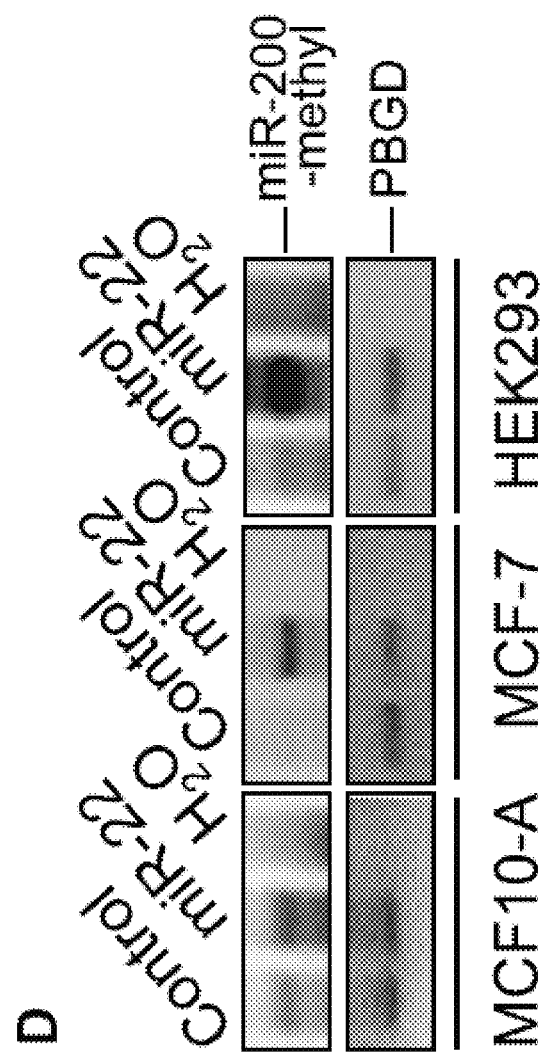
Figure 11E:
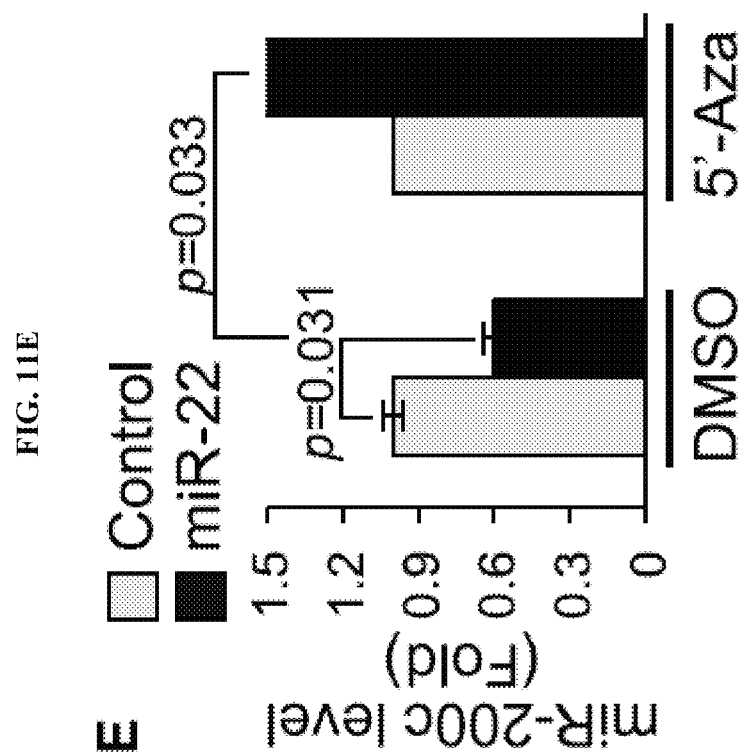

CpG island hypermethylation-mediated epigenetic silencing of the miR-200 family is associated with upregulation of Zeb1/Zeb2 expression, EMT and metastasis. The promoter of mir-200 was analyzed using the methyl-specific PCR (MSP) analysis and found that it is indeed hypermethylated upon miR-22 overexpression (FIG. 11D). Treatment of these cells with a DNA-demethylating agent, 5'-aza-2'-deoxycytidine (5'-Aza), reversed the effects of miR-22 and restored expression of miR-200 transcripts (FIG. 11E), suggesting that miR-22 may have a functional role in the dynamic control of DNA methylation.

Figure 11F:
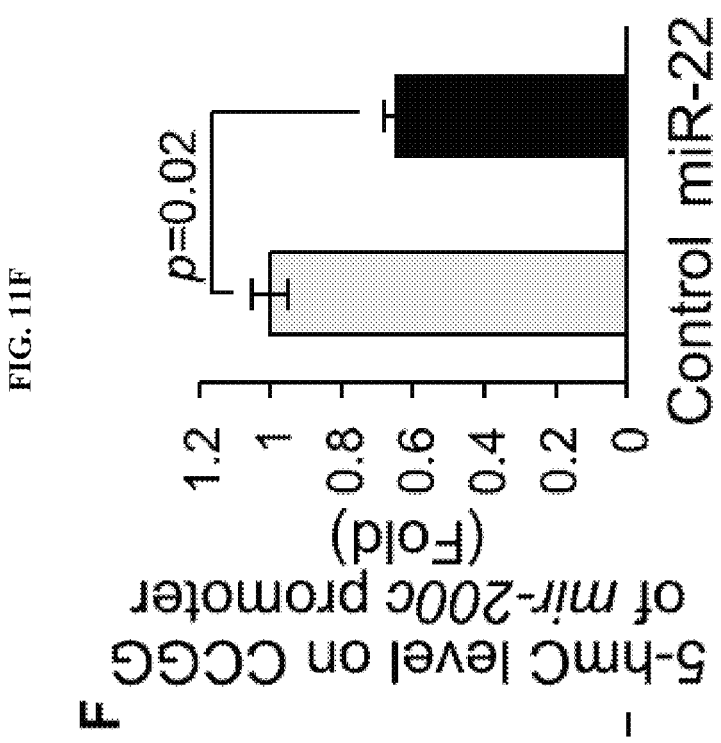

It was tested whether miR-22 antagonizes miR-200 transcription by controlling 5hmC levels on genomic DNA. Indeed, miR-22 overexpression significantly depleted 5hmC levels within mir-200 promoter CpG islands (FIG. 11F). These results suggest that miR-22 suppresses the demethylation of the promoter within the mir-200 gene and represses its expression, leading to upregulation of its cognate targets.

Figure 11G:
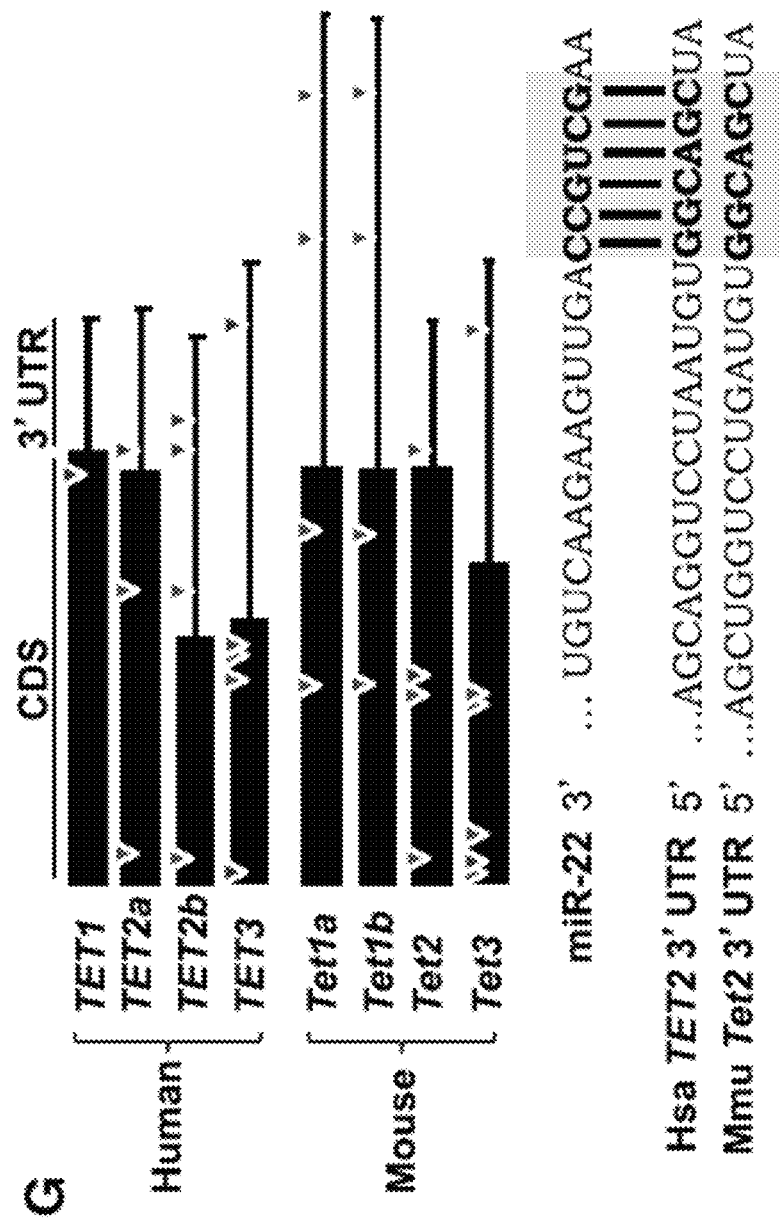
Figure 11H:
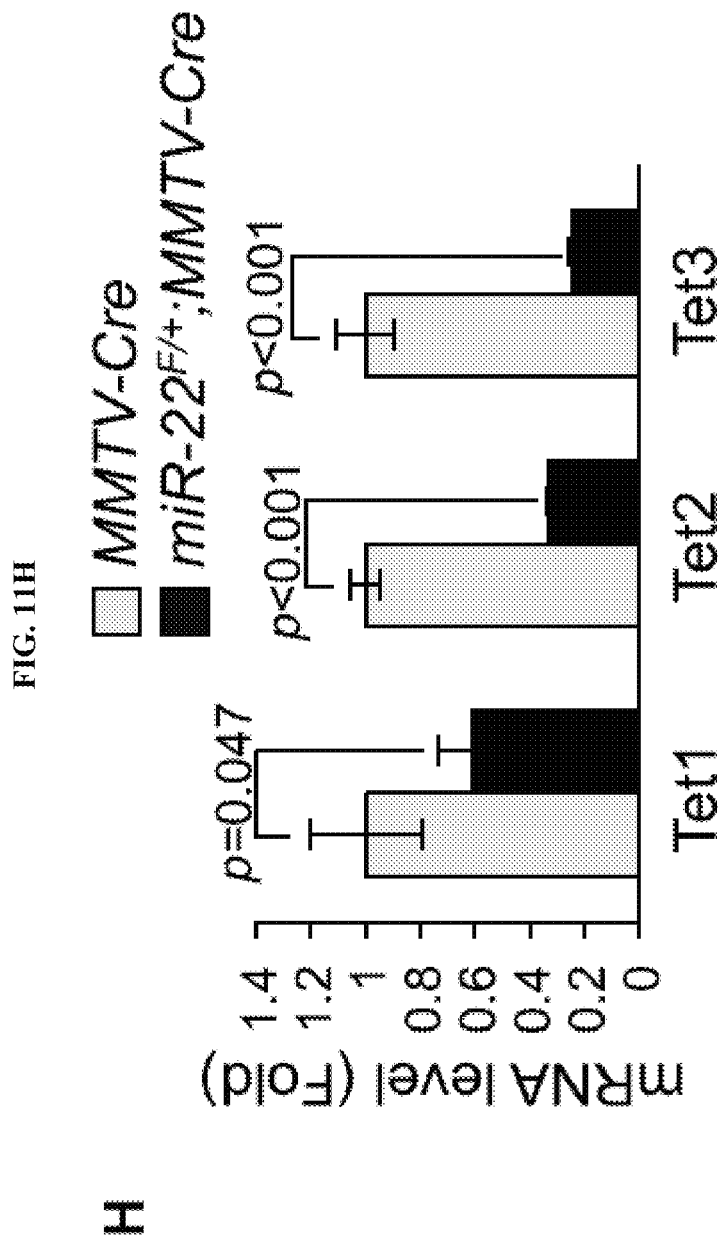
Figure 11I:
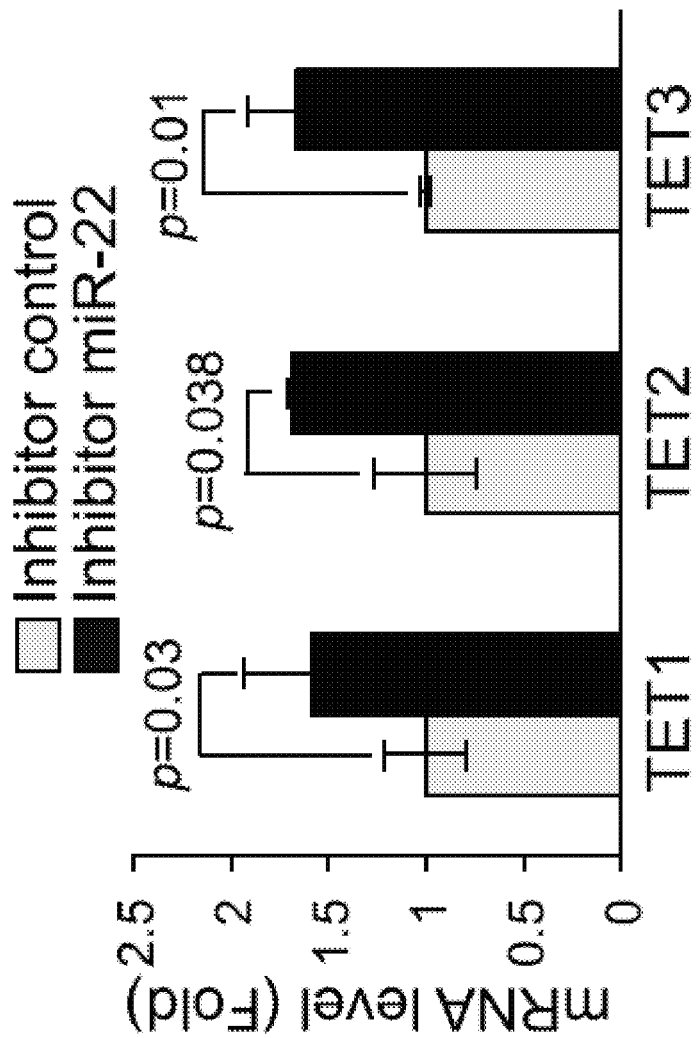
Figure 1I:
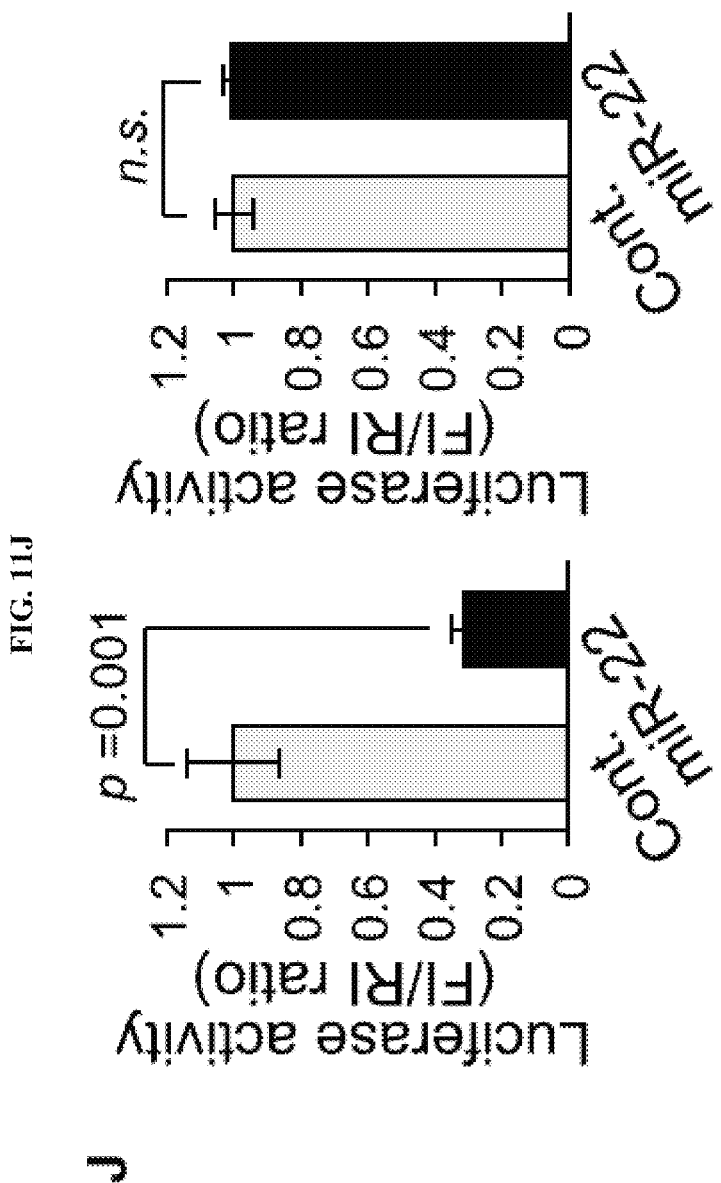

Example 10: miR-22 Regulates the Level of 5-Hydroxymethylcytosine by Directly Targeting TET Family Members Having shown the oncogenic function for miR-22 in breast cancer, studies to identify the targets of its oncogenic activity in breast cancer were undertaken. Potential molecular targets of miR-22 were predicted by prediction algorithms including TargetScan 6.0, microRNA.org and miRBase. Among the potential targets, the focus was on the TET family (FIG. 11G). Real-time qPCR and Western blot analyses revealed that miR-22 expression in MCF-10A, human embryonic kidney (HEK) 293 cells, and in vivo in the mammary glands of miR-22$^{F/+}$;MMTV-Cre mice leads to a robust downregulation of TET family members (FIG. 11H). This was in agreement with the high-degree of cross species conservations of the predicted miR-22 microRNA recognition elements (MREs) in TET family members (FIG. 11G). In contrast, inhibiting miR-22 by using antisense oligonucleotides resulted in a significant elevation in expression of TET family members (FIG. 11I). A luciferase reporter assay performed using the 3'UTR region of TET2 (which however contains the miR-22 MREs also identical within the 3'UTR of TET1, TET2 and TET3) (FIG. 11G), and its mutant version in the miR-22 MREs, demonstrated that miR-22-mediated repression of TET is due to a direct interaction between miR-22 and the TET genes (FIG. 11J).

Figure 11K:
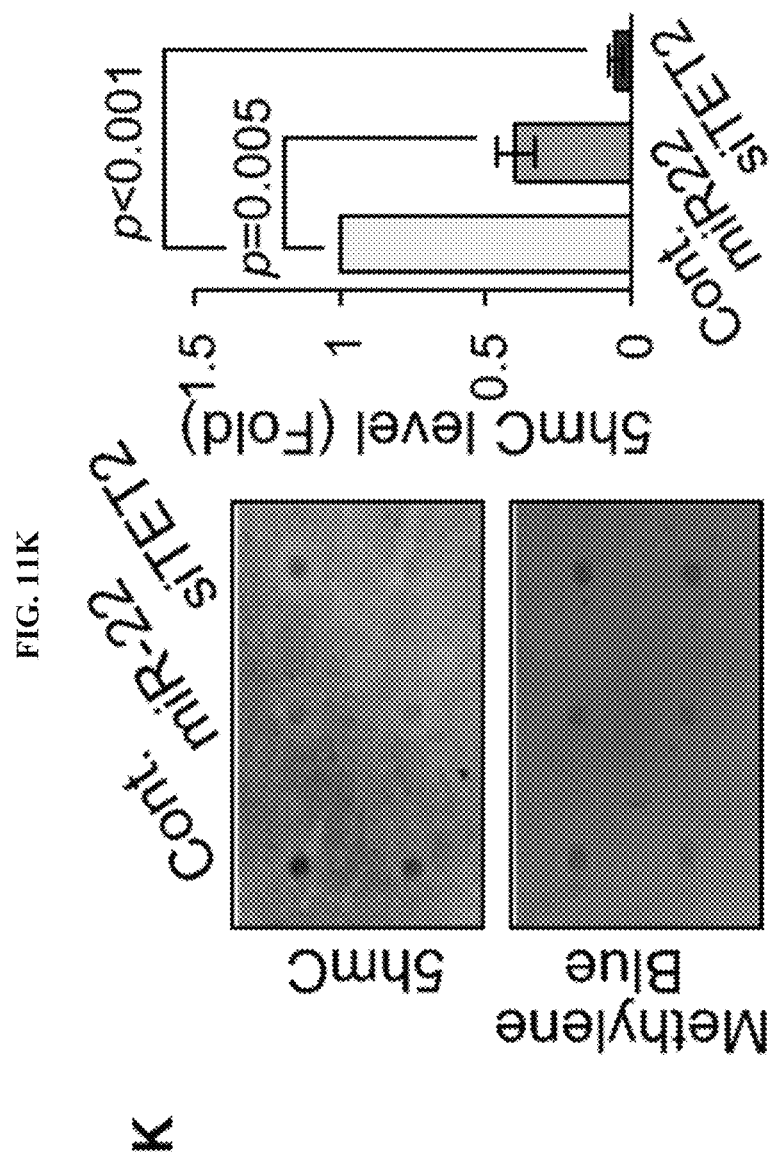
Figure 11L:
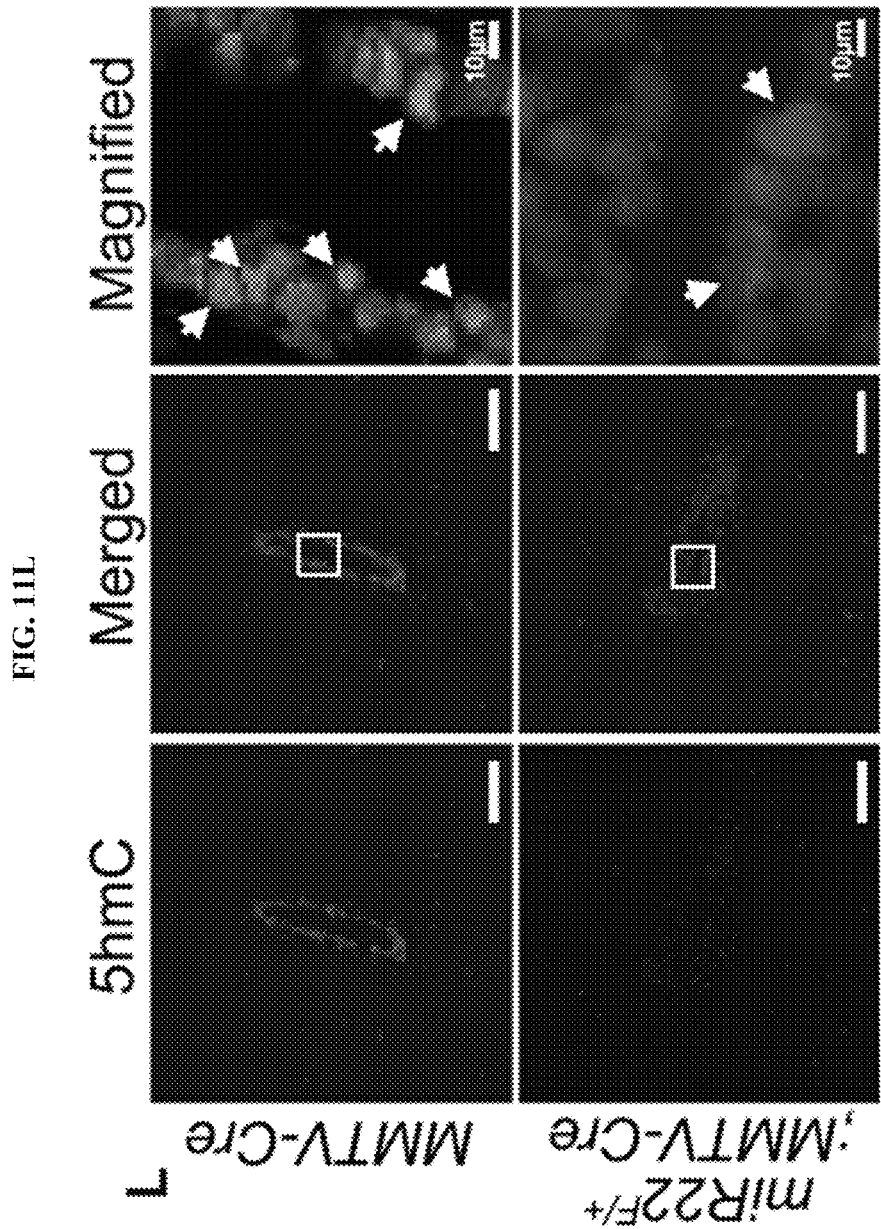

It was further studied whether miR-22 can remodel the epigenetic landscape by altering 5hmC levels in the genome through the TET family. Dot blot assay and immunofluorescence analysis with anti-5hmC antibodies revealed that miR-22 overexpression in MCF-10A cells is indeed able to reduce global 5hmC levels (FIG. 11K). 5hmC levels were drastically reduced in vivo in the mammary glands of miR-22$^{F/+}$;MMTV-Cre mice compared to littermate controls (FIG. 11L). These data suggest that changes in this important epigenetic mark (e.g., 5hmC) may contribute to the ability of miR-22 to impact on EMT, stemness, and metastasis.

Figure 12A:
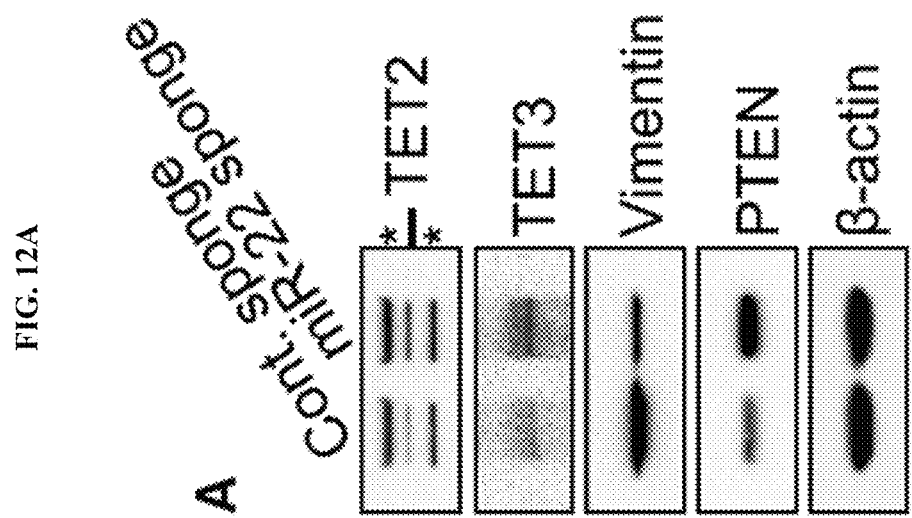
Figure 12B:
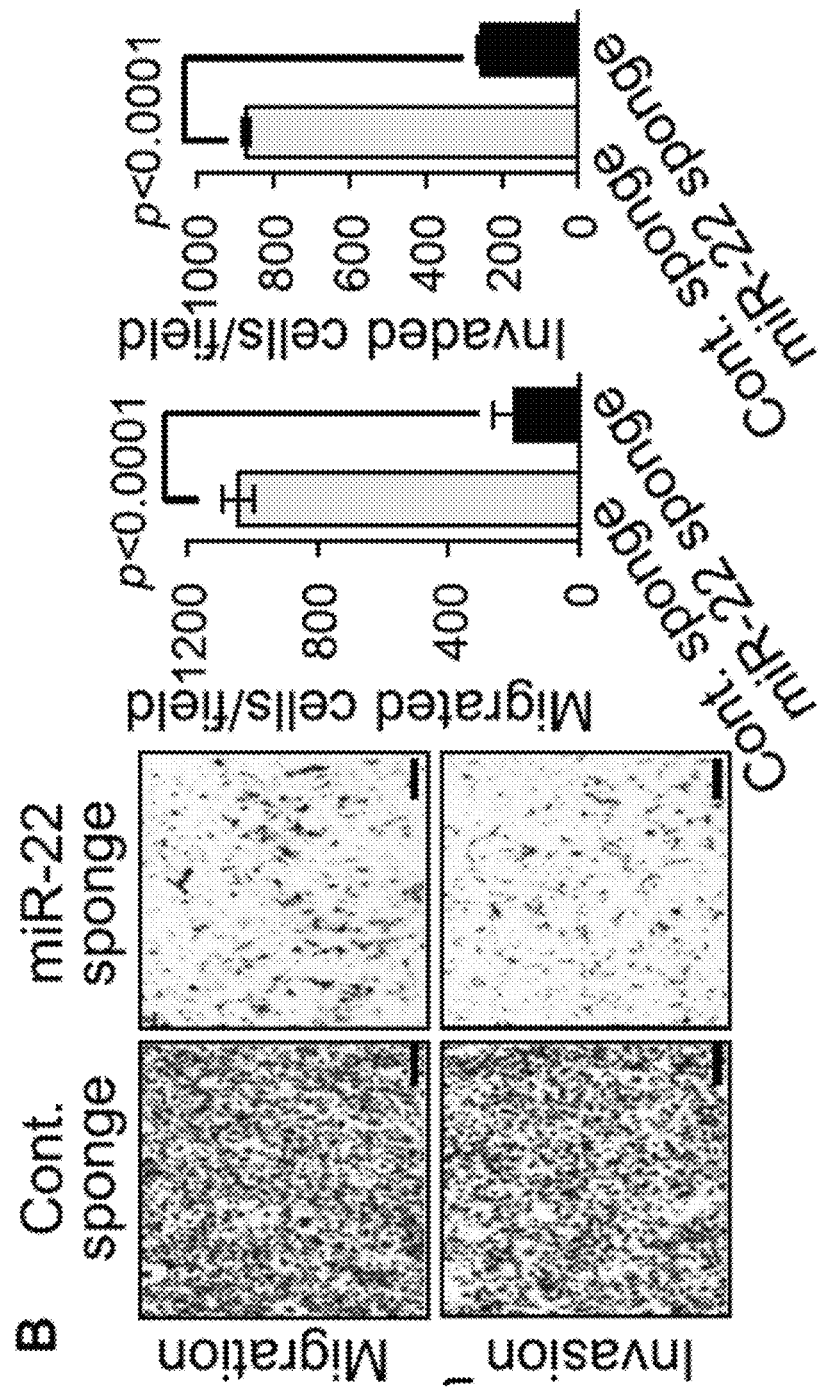
Figure 12C:
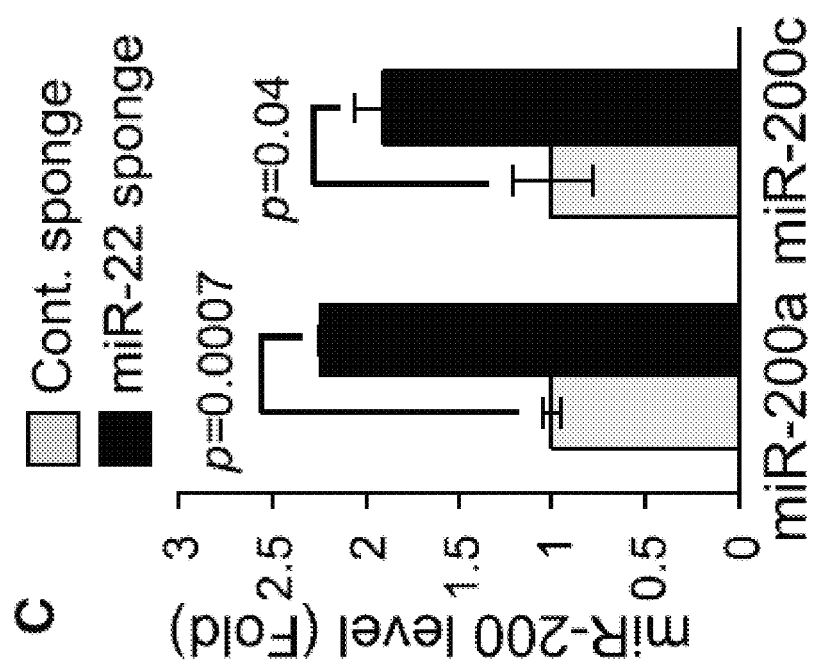
Figure 12D:
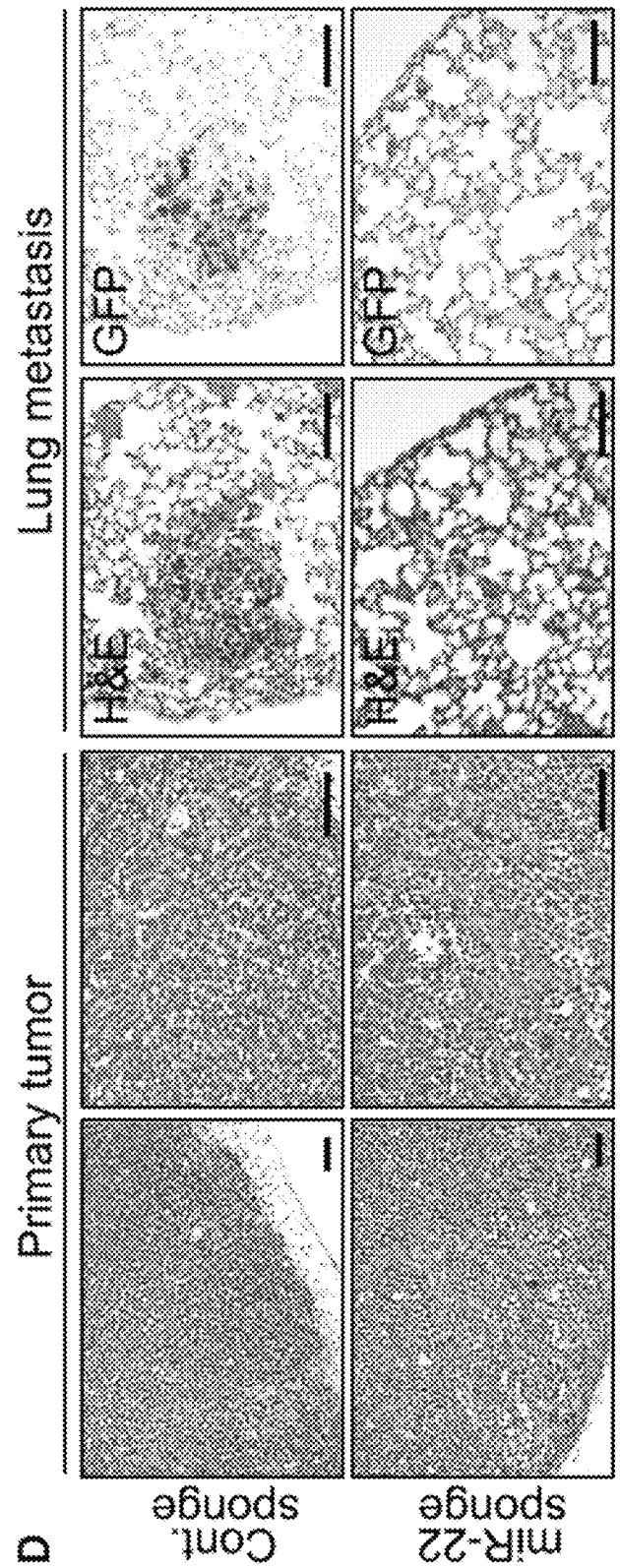
Figure 12F:
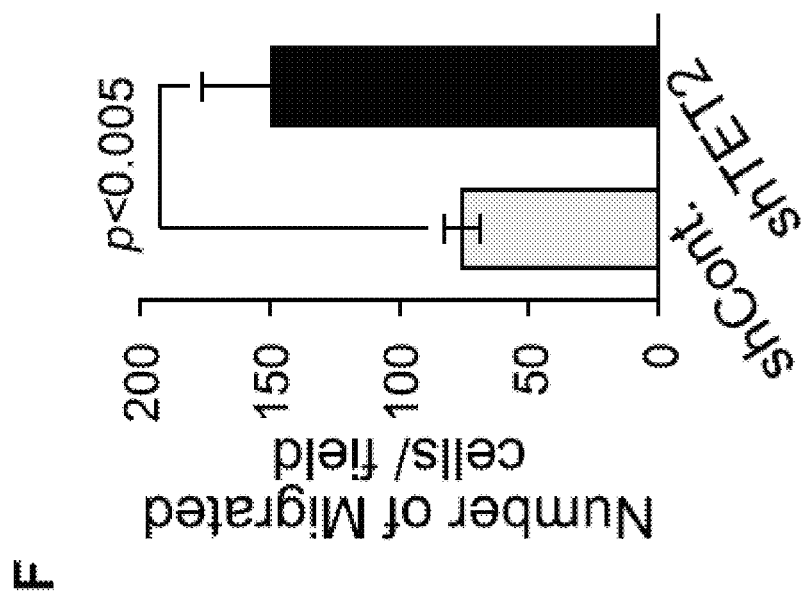
Figure 12G:
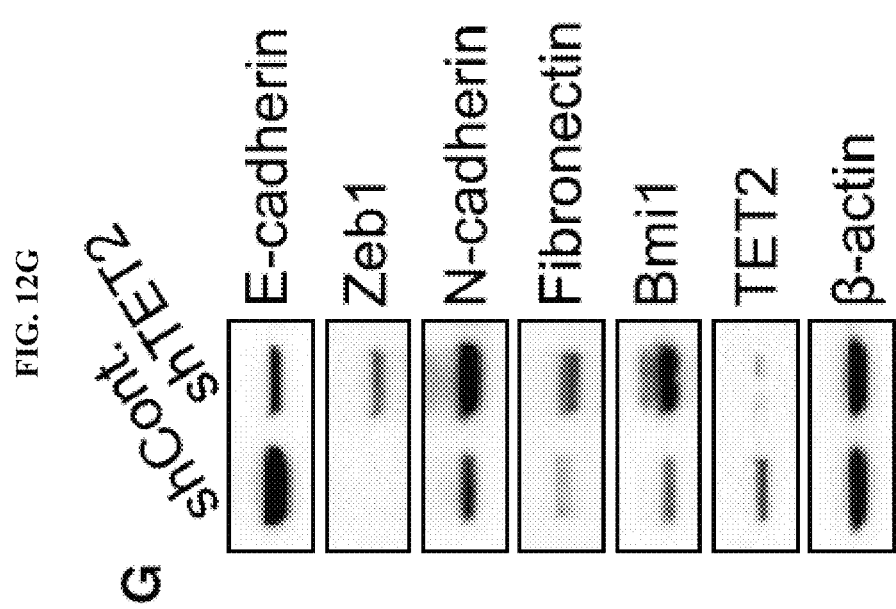
Figure 12H:
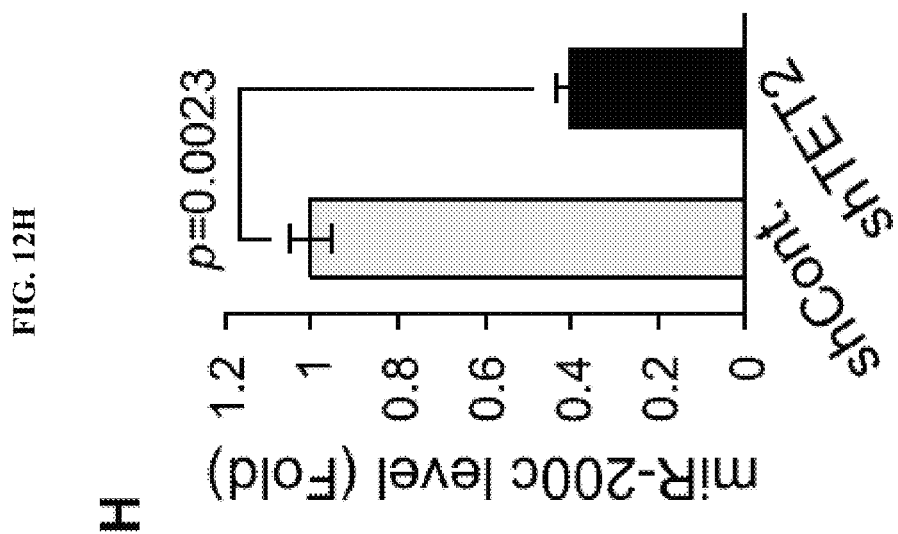
Figure 12I:
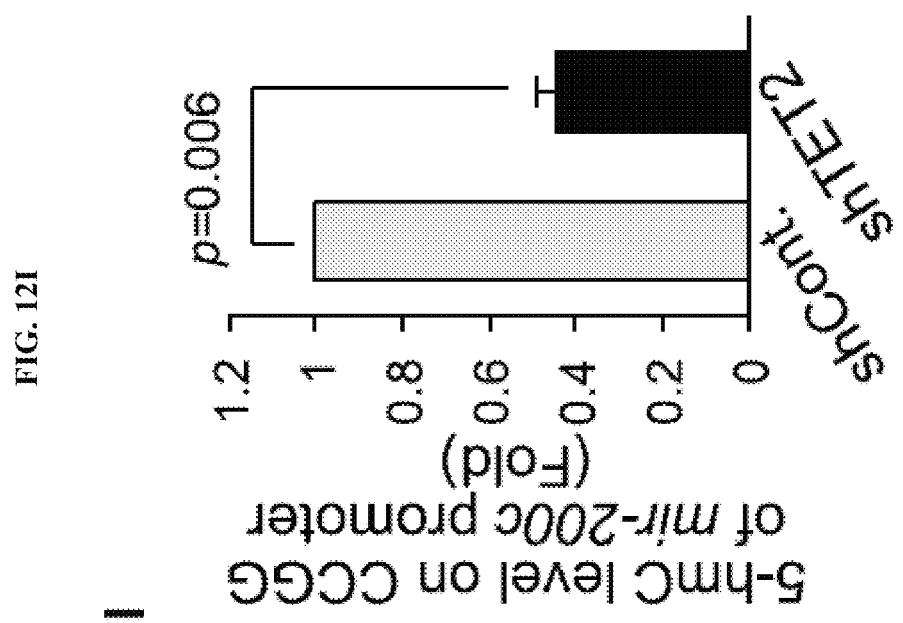
Figure 12J:
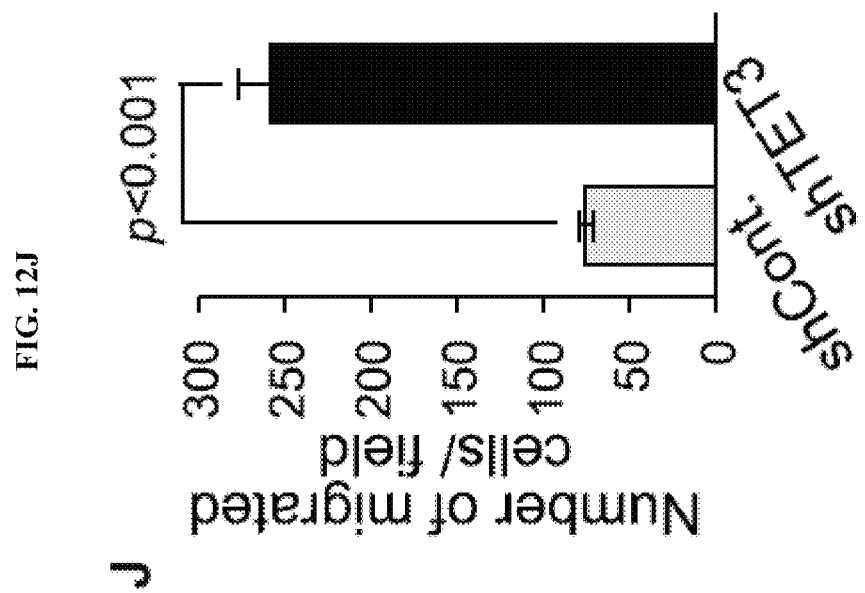
Figure 12K:
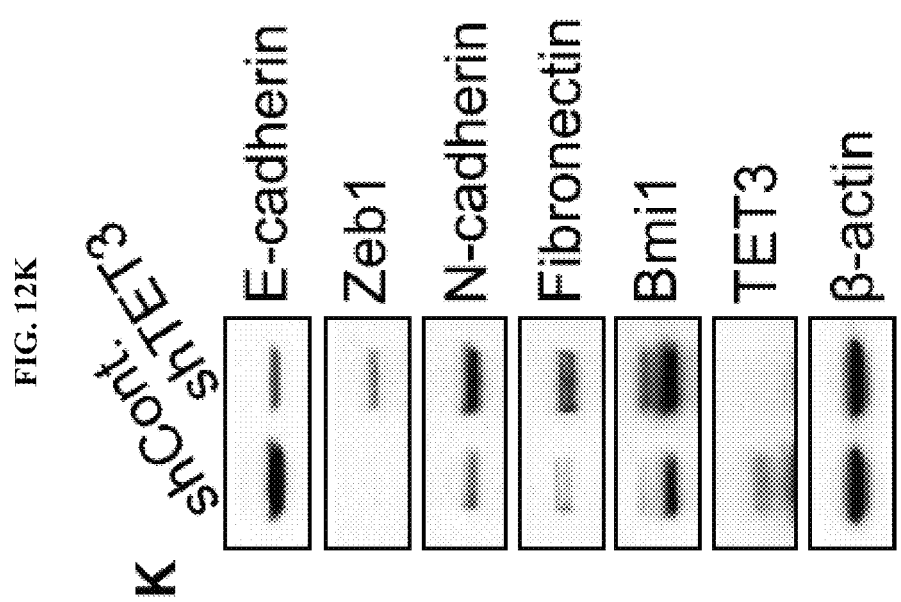
Figure 12L:
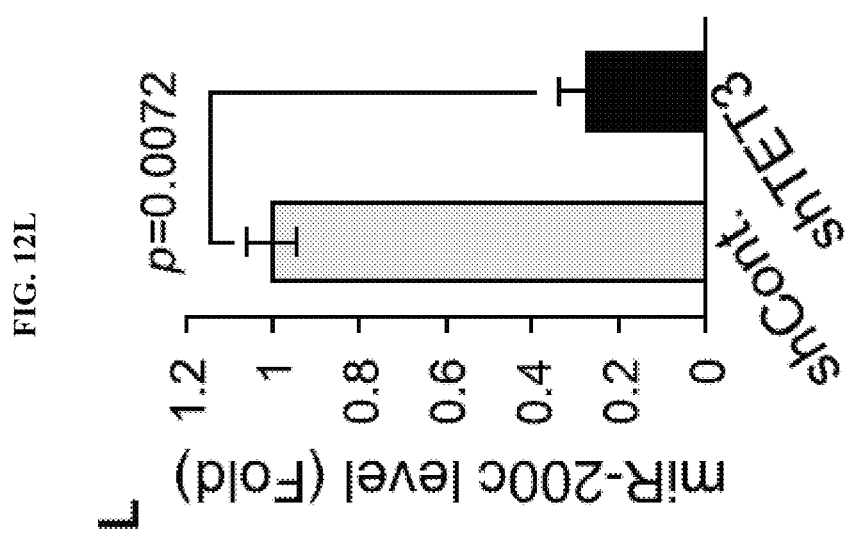
Figure 12M:
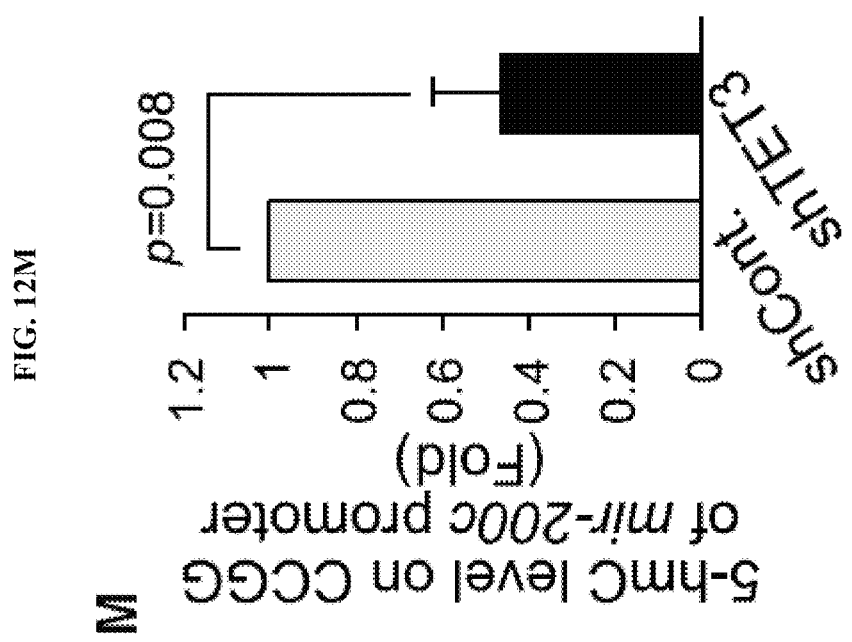

Example 11: Downregulation of miR-22 or the TET Family Members Alters EMT, Stemness and miR-200 Expression Levels Next it was determined that miR-22 inhibition suppresses EMT, leading to the elevation of expression of TET and miR-200. miR-22 expression rates in a large panel of breast cancer cells (including 2 non-tumorigenic cells, 7 ERα-positive and 4 ERα-negative breast cancer cell lines) was evaluated. LM2 cells were focused on as these cells are highly metastatic and express a substantial amount of miR-22 compared to other breast cancer cell lines. A retroviral polymerase II sponge was generated by inserting miR-22 binding sites, arrayed in tandem, into the 3'UTR of a reporter gene encoding destabilized GFP driven by the CMV promoter. These miR-22 binding sites were perfectly complementary in the seed region, with a bulge at positions 9-12 to prevent degradation of the sponge RNA. To examine the effects of miR-22 inhibition on EMT and miR-200 expression, LM2 cells expressing abundant endogenous miR-22 were infected with either the CXCR4 control sponge plasmid (Cont. Sponge) or the sponge plasmid complementary to miR-22 (miR-22 Sponge). Inhibition of miR-22 by the miR-22 sponge in LM2 cells led to a reduction of metastatic phenotypes, as measured by cell migration, invasion abilities and the expression of the mesenchymal marker Vimentin accompanied with elevation in the levels of TET proteins (FIGS. 12A and 12B). Noticeably, inhibiting miR-22 by the miR-22 sponge also resulted in a significant increase in the levels of miR-200 family members (FIG. 12C). In agreement with these in vitro observations, miR-22 decoying by the miR-22 sponge drastically inhibited in vivo breast cancer metastases to the lung in xenograft models established with LM2 cells (FIGS. 12D and 12E).

It was next investigated whether repression of TET family members could account for the phenotypes caused by miR-22 overexpression in EMT, stemness, and metastasis. To this end, we knocked down TET2 or TET3 in MCF-10 OA cells by using RNA interference (RNAi), and analyzed the resulting effect on EMT and stemness. Notably, knockdown of TET2 or TET3 by RNAi enhanced epithelial cell migration, EMT and mammosphere formation, suggesting that repression of the TET family creates phenotypes similar to those of miR-22 overexpression (FIG. 12F, FIG. 12G, FIG. 12J and FIG. 12K). Furthermore, downregulation of TET2 or TET3 resulted in a reduction in 5hmC levels at the mir-200 promoter, and caused a decline in miR-200 expression (FIGS. 12H, 12I, 12L and 12M).

To further understand the metastasis-suppression function of TET family members in vivo, we analyzed lung metastases in MCF-7 xenograft models with stable knockdown of TET2. Importantly, mice that received the orthotopic implantation of TET2-depleted MCF-7 cells displayed a suggestive lung metastasis. Taken together, these data indicate that TET family members inhibit EMT, stemness and tumor metastasis, and positively regulate miR-200 expression.

Example 12: miR-22-Induced EMT, Stemness and Repression of miR-200 Rely on its Ability to Silence TET Family Members To finally determine whether TET family members directly contribute to miR-22 function, TET2 or TET3 were ectopically expressed in miR-22-overexpressing MCF-10A cells and then analyzed epithelial cell migration, EMT and stemness. The exogenously expressed TET proteins significantly diminished the cell migration, EMT and mammosphere formation elicited by miR-22 overexpression (FIGS. 13A-13C and 13F-13H). Furthermore, silencing the expression of global 5hmC and miR-200 caused by miR-22 was rescued by the ectopic expression of TET2 or TET3 (FIGS. 13D, 13E, 13I and 13J), suggesting, without wishing to be bound by theory, that TET proteins are very likely to be major factors in reliable miR-22 function in suppression of demethylation of miR-200.

Figure 13A:
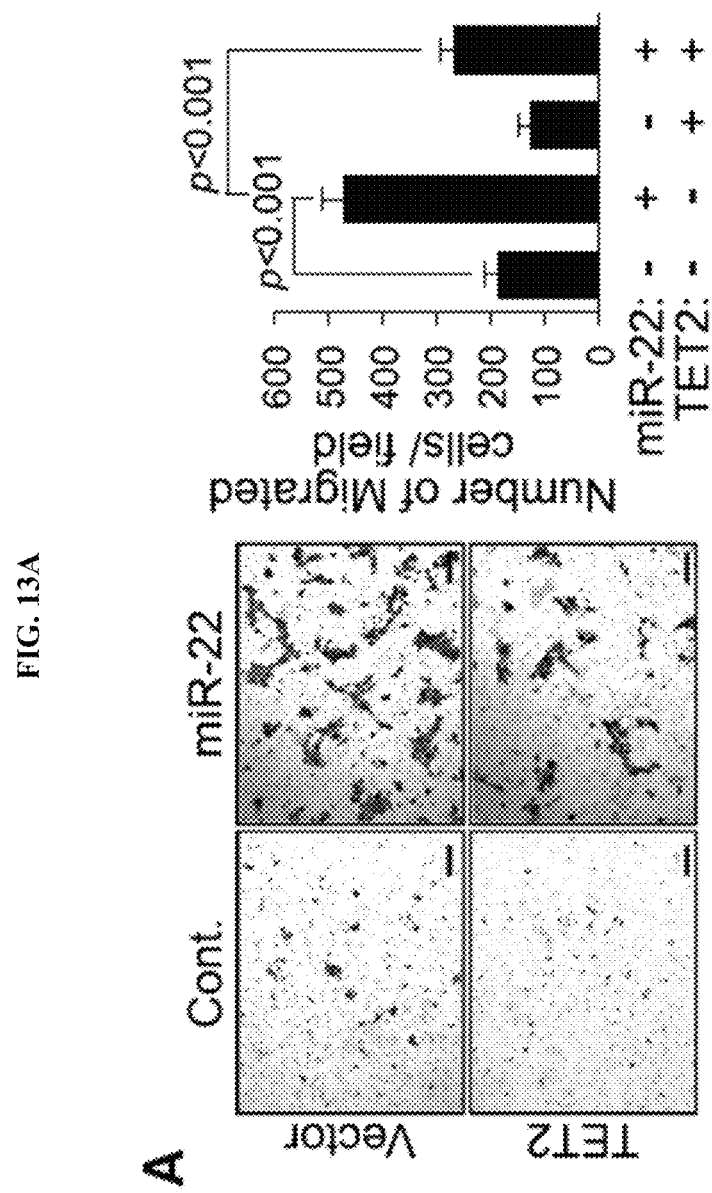
FIGS. 13A-L show that TET family members are required for miR-22-induced EMT, stemness and miR-200 repression.
Figure 13B:
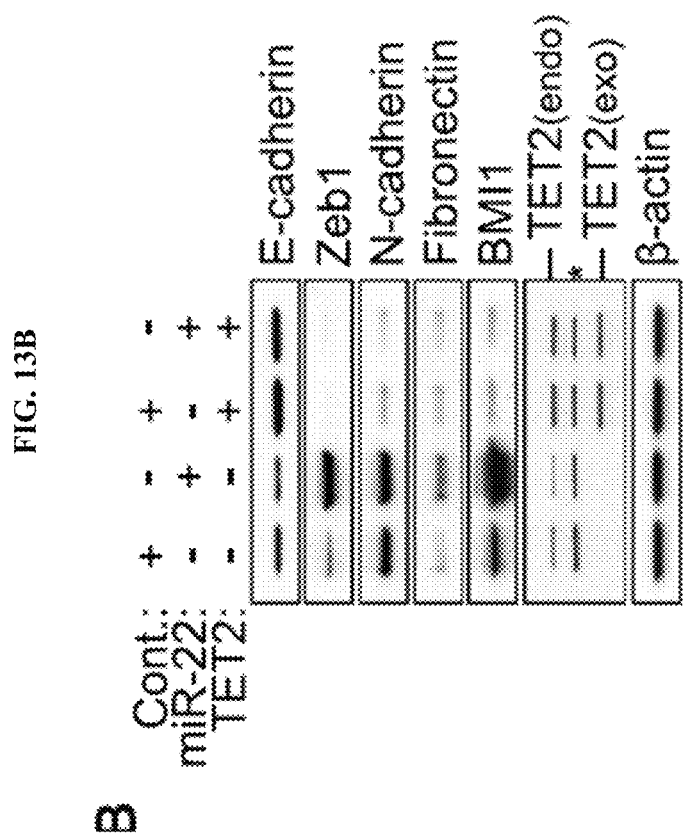
Figure 13C:
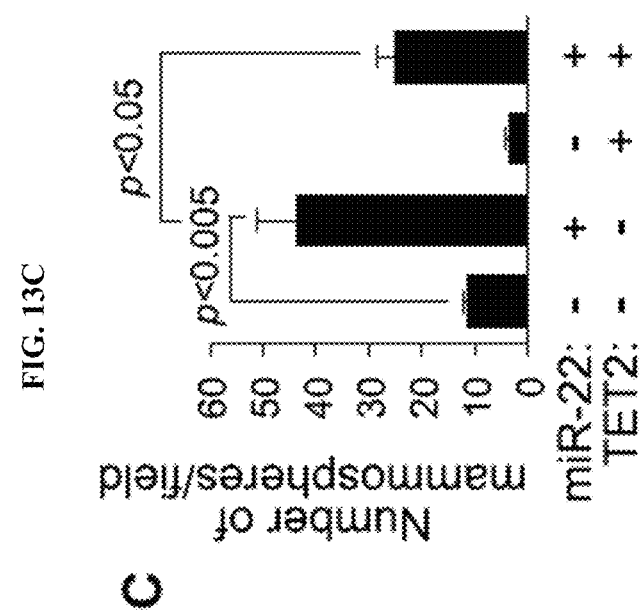
Figure 13D:
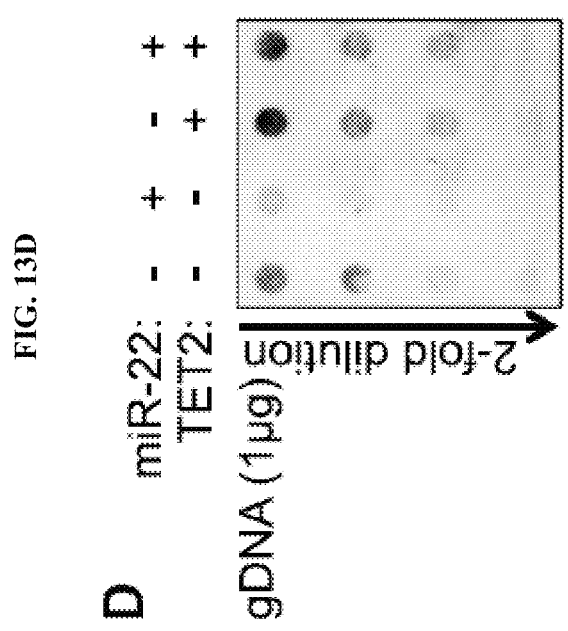
Figure 13E:
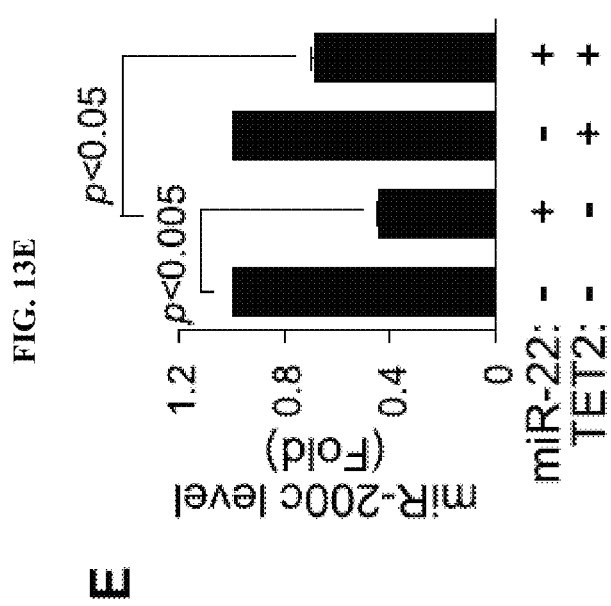
Figure 13F:
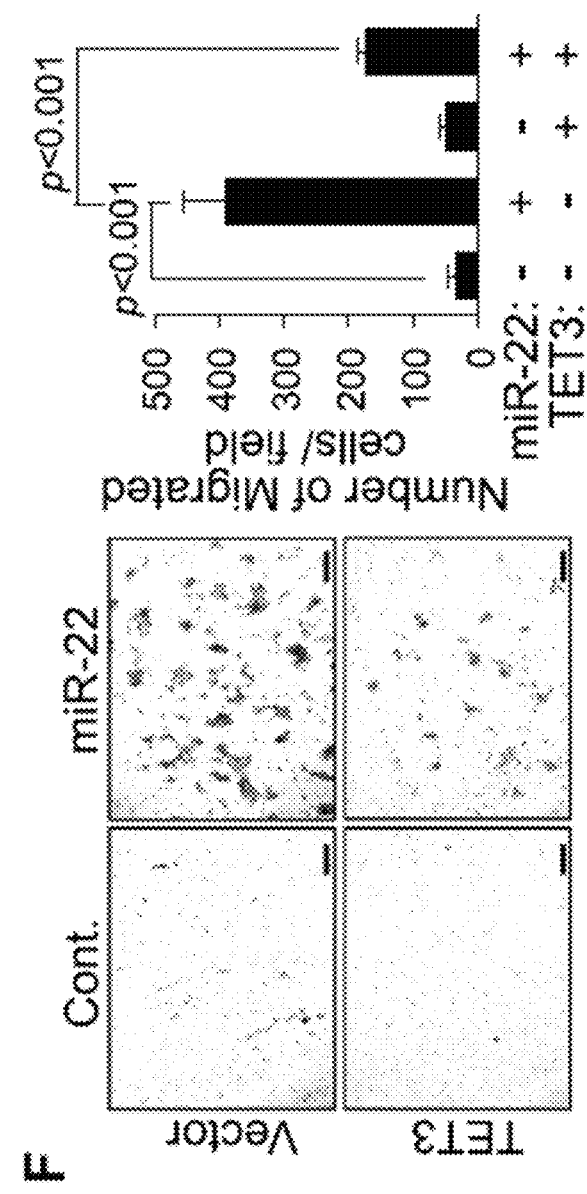
Figure 13G:
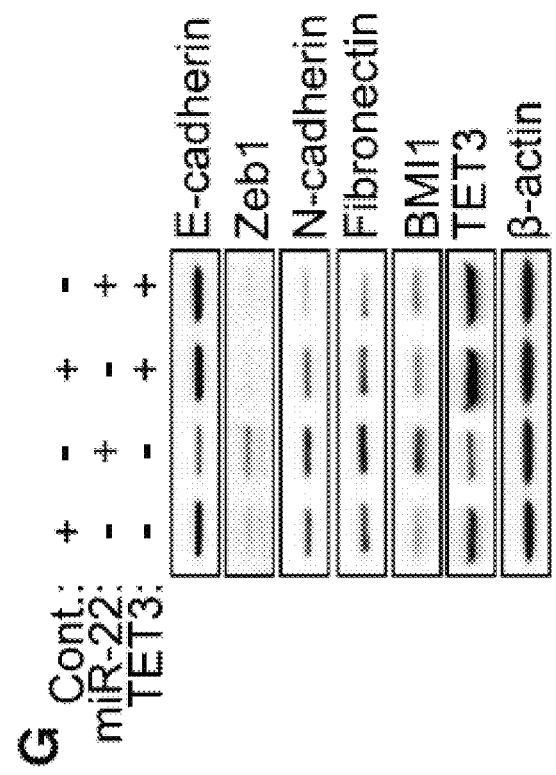
Figure 13H:
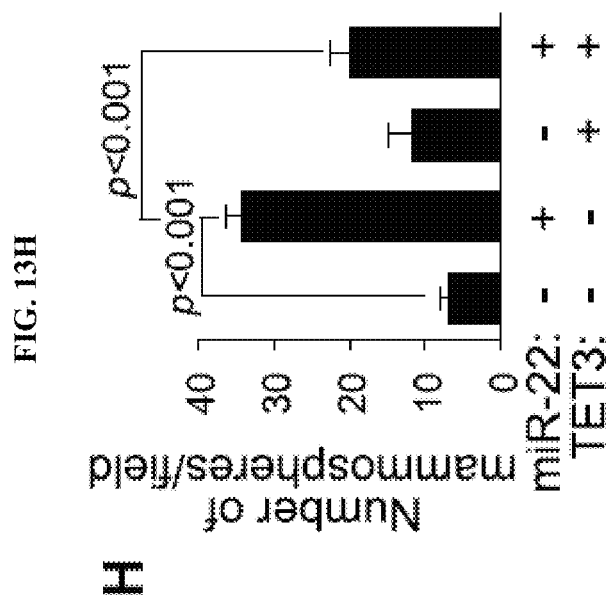
Figure 13I:
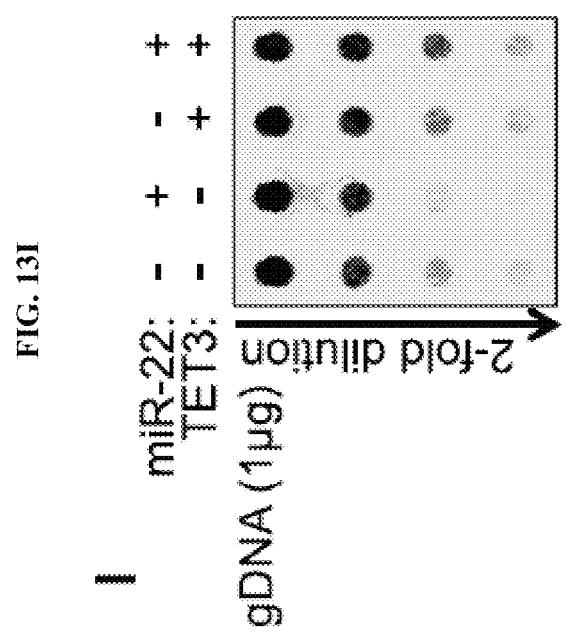
Figure 13J:
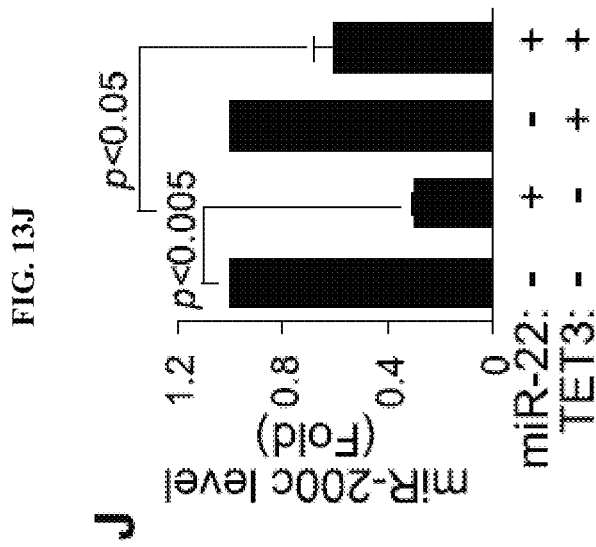
Figure 13K:
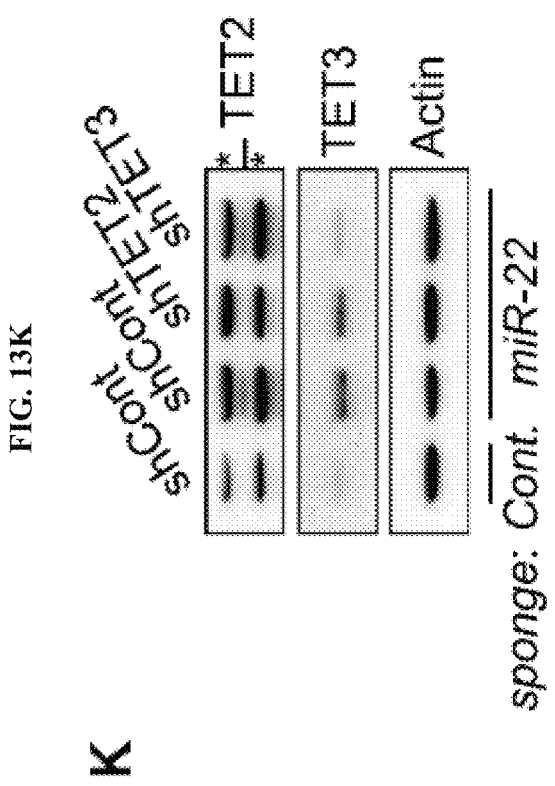
Figure 13L:
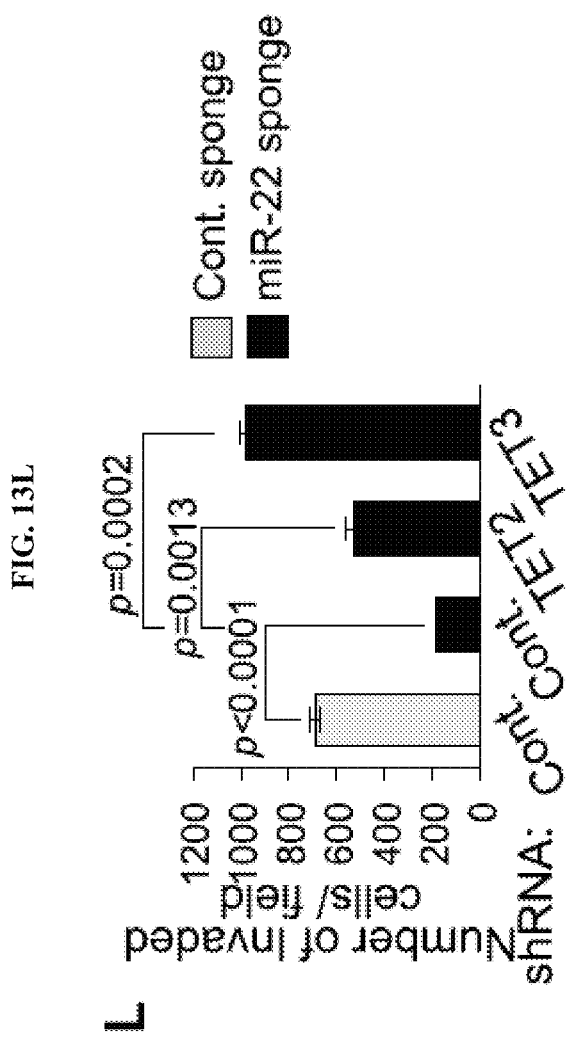

To further evaluate whether the invasion-suppression capacity of miR-22 inhibition directly relates to the TET family, TET2 or TET3 were knocked down by RNAi in LM2 metastatic breast cancer cell line after applying the miR-22 sponge (FIG. 13K). Noticeably, the dramatic reduction in cell invasion caused by miR-22 inhibition was overcome by knockdown of TET proteins (FIG. 13L). These data suggest that TET family members are the major players responsible for miR-22 function in EMT, stemness and repression of miR-200.

Figure 14A:
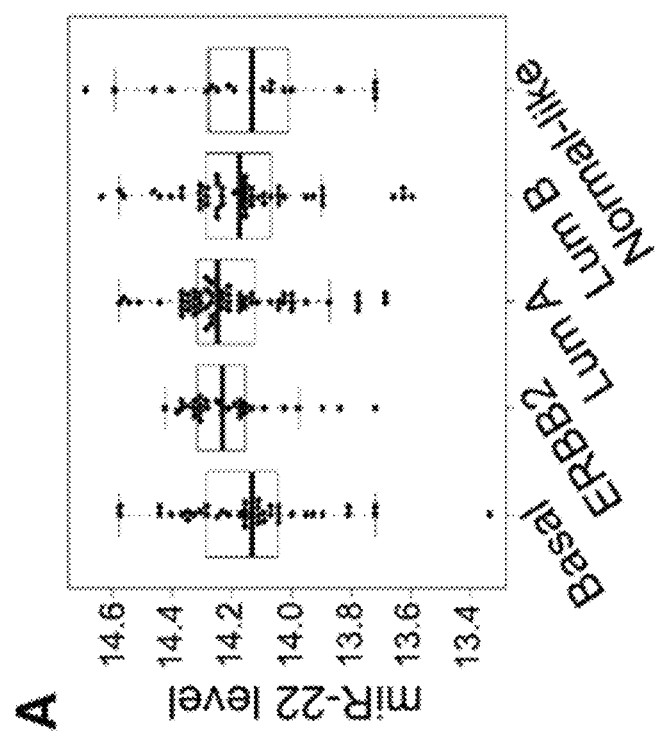
FIGS. 14A-F show that miR-22 overexpression correlates with poor clinical outcomes and silencing of the TET-miR-200 axis in patients.

Example 13: miR-22 Overexpression Correlates with Poor Clinical Outcomes and Silencing of the TET-miR-200 Axis in Patients Further studies were undertaken in human breast cancer patient samples. A high expression rate of miR-22 in non-triple-negative breast cancer (non-TNBC) subtypes of breast cancer when compared to normal breast tissue was observed (FIG. 14A).

Figure 14B:
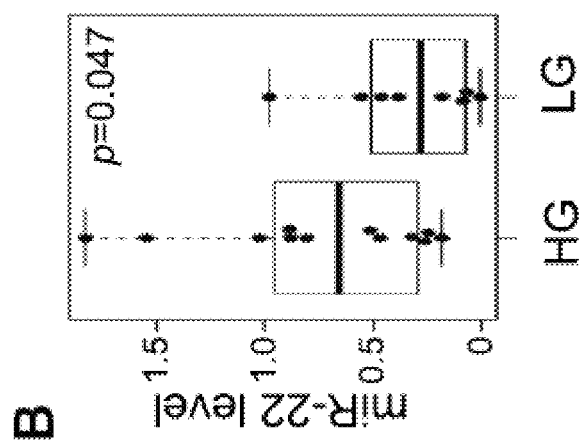
Figure 14C:
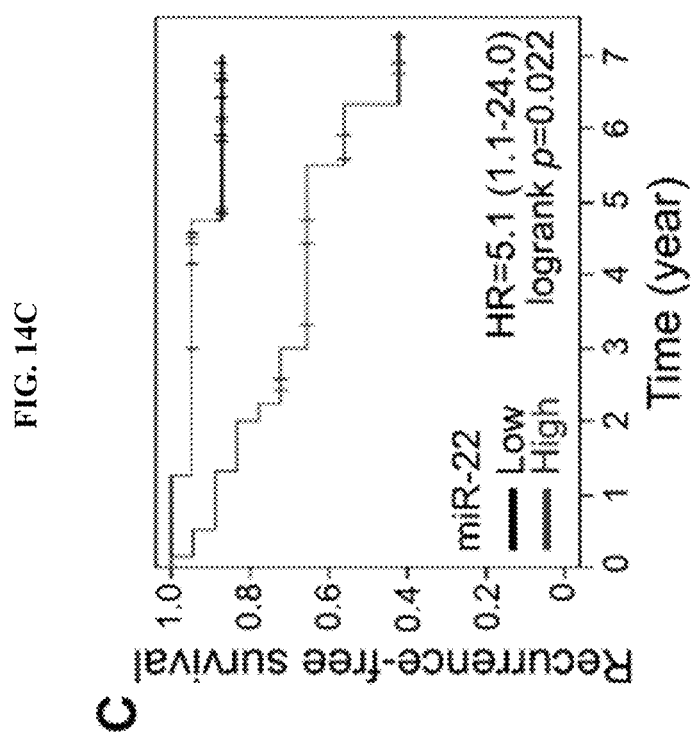

To further evaluate the relationship between miR-22 overexpression and tumor aggressiveness in non-TNBC patients, miR-22 levels in breast cancer tissue samples positive for ERα (estrogen receptor α) were analyzed by real-time qPCR, using RNU6B as an internal control. The breast cancer patients found to have high expression levels of miR-22 had high-grade tumors of an advanced stage (p=0.047; FIG. 14B), and poor survival rates as compared to the patients with low miR-22 expression levels (p=0.022, FIG. 14C).

Figure 14D:
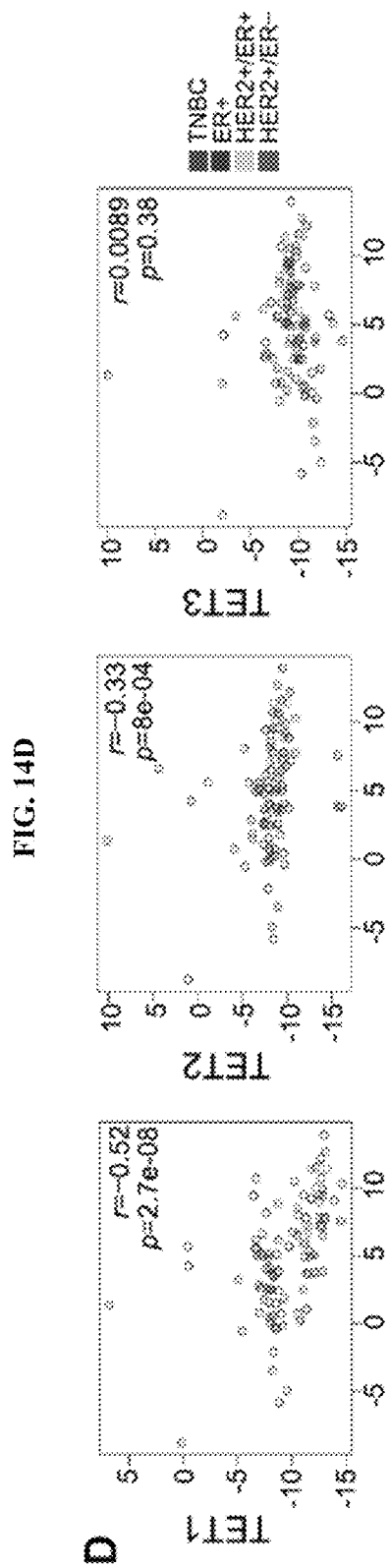

In this analysis miR-22 was also found to be significantly co-expressed with genes involved in breast cancer metastasis, including those that encode matrix metalloproteases 11 and 1 (Pearson r=0.536 and 0.392, respectively), cathepsin B (0.500), integrin all (0.425), TGF-βR-associated protein (0.416), collagen Xα1 (0.411), TGF-31 (0.407), fibronectin 1 (0.403) and laminin α5 (0.399). This observation also supports the notion that in breast cancer miR-22 is pro-metastatic and contributes to aggressive disease.

miR-22 expression was directly anti-correlated with the expression of TET1 and TET2 in human breast cancer patients; in addition, a statistically significant anti-correlation between miR-22 and TET3 was also observed, but only in the non-TNBC breast cancer subset (FIG. 14D and p=0.014).

Figure 14E:
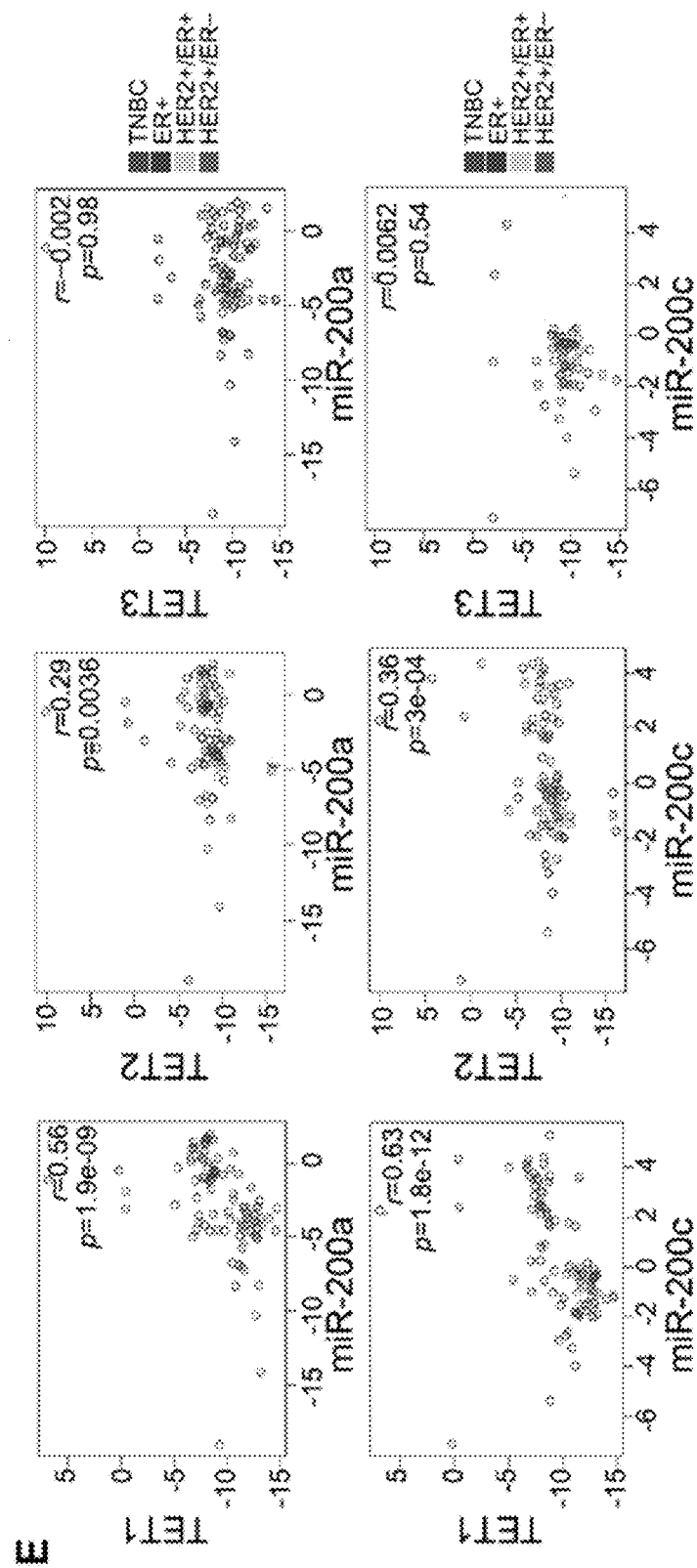
Figure 14F:
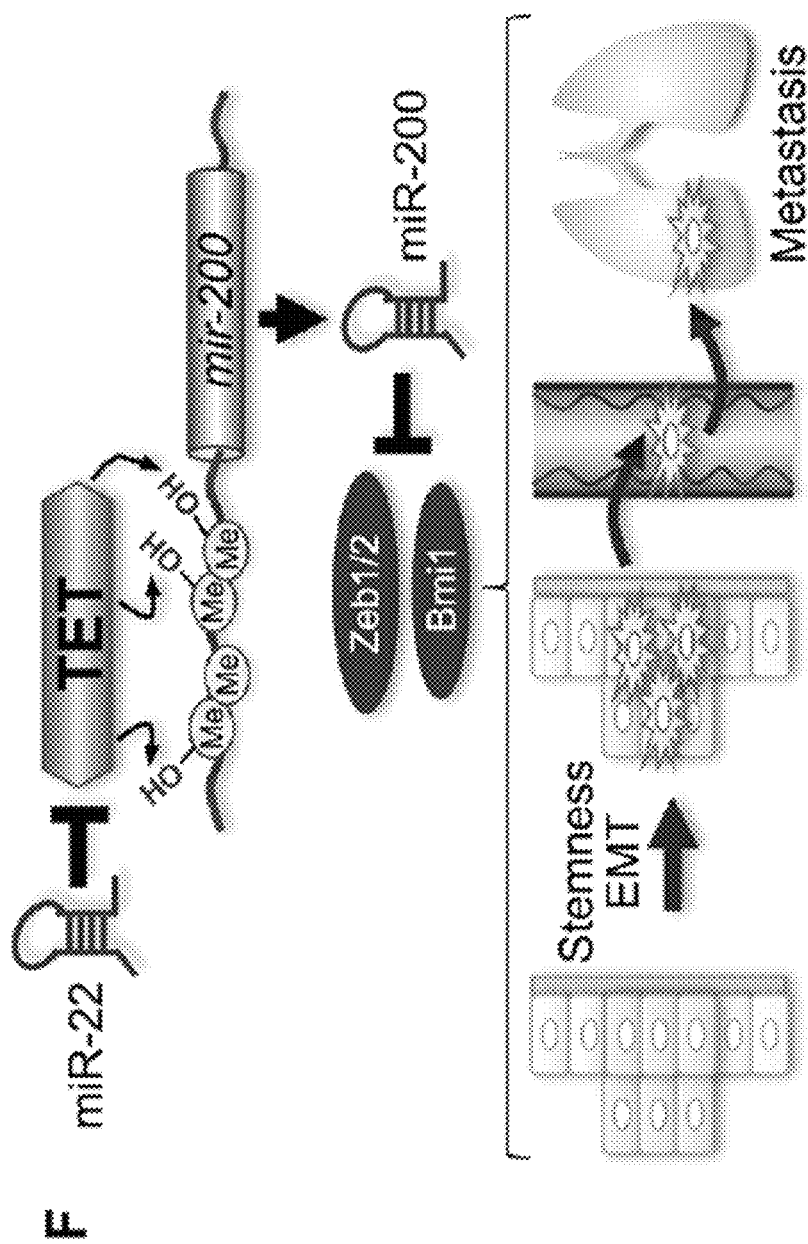

Lastly, a connection between downregulation of TET family members by miR-22 and its effects on miR-200s expression in human breast cancer tissues was verified. A clear correlation between the expression of TET1 and TET2 and miR-200s in human breast cancer patients was observed and a correlation was also found between TET3 and miR-200s (FIG. 14E). Taken together, these results reveal miR-22 as a crucial and unexpected switch for a metastatic phenotype of breast cancer via repression of TET family members/miR-200s.

All patents and publications referenced herein are hereby incorporated by reference in their entireties.

The publications discussed herein are provided solely for their disclosure prior to the filing date of the present application. Nothing herein is to be construed as an admission that the present invention is not entitled to antedate such publication by virtue of prior invention.

As used herein, all headings are simply for organization and are not intended to limit the disclosure in any manner. The content of any individual section may be equally applicable to all sections.

It is understood that the disclosed invention is not limited to the particular methodology, protocols and materials described as these can vary. It is also understood that the terminology used herein is for the purposes of describing particular embodiments only and is not intended to limit the scope of the present invention, which will be limited only by the appended claims.

Those skilled in the art will recognize, or be able to ascertain using no more than routine experimentation, many equivalents to the specific embodiments of the invention described herein. Such equivalents are intended to be encompassed by the following claims.

What is claimed is:

1. A method of treating cancer, comprising administering to a subject in need thereof an inhibitor of miR-22, wherein the inhibitor is an antisense oligonucleotide of at least 7 nucleotides in length that is 100% complementary over its entire length to a miR-22 sequence, and wherein the cancer is selected from a blood-based cancer or breast cancer that overexpresses miR-22 relative to normal blood or breast cells or tissues.

2. The method of claim 1, wherein one or more nucleotides of the inhibitor are chemically modified and the chemical modification is selected from locked nucleic acid (LNA), phosphorothioate, 2'-O-Methyl, 2'-O-Methoxyethyl, 2'-O-alkyl-RNA unit, 2'-OMe-RNA unit, 2'-amino-DNA unit, 2'-fluoro-DNA unit, peptide nucleic acid (PNA) unit, hexitol nucleic acids (HNA) unit, INA unit, and a 2'-O-(2-Methoxyethyl)-RNA (2' MOE RNA) unit.

3. The method of claim 1, wherein the antisense oligonucleotide comprises 16 or fewer nucleotides.

4. The method of claim 1, wherein the blood-based cancer is a leukemia, lymphoma, myeloma or myelodysplastic/myeloproliferative neoplasm (MDS/MPN).

5. The method of claim 4, wherein the leukemia is acute lymphocytic leukemia (ALL), acute myelogenous leukemia (AML), chronic lymphocytic leukemia (CLL), or chronic myelogenous leukemia (CML).

6. The method of claim 4, wherein the lymphoma is a Hodgkin lymphoma or a non-Hodgkin lymphoma.

7. The method of claim 4, wherein the myeloma is IgG, IgE, IgA, IgM, IgD, light chain, or non-secretory myeloma.

8. The method claim 1, wherein the breast cancer is one or more of $ER^+$, $PR^+$, $HER2^+$, $AR^+$, and $PRLr^+$.

9. The method of claim 1, wherein the breast cancer is one or more of $ER^-$, $PR^-$, $HER2^-$, $AR^-$, and $PRLr^-$.

10. A method of preventing metastasis, comprising administering an effective amount of an inhibitor of miR-22 to a subject having cancer, wherein the inhibitor is an antisense oligonucleotide of at least 7 nucleotides in length comprising a sequence that is 100% complementary over its length to a miR-22 sequence, and wherein the cancer is selected from a blood-based cancer or breast cancer that overexpresses miR-22 relative to normal blood or breast cells or tissues.

* * * * *

```
                        SEQUENCE LISTING

<160> NUMBER OF SEQ ID NOS: 4

<210> SEQ ID NO 1
<211> LENGTH: 22
<212> TYPE: DNA
<213> ORGANISM: Homo sapiens

<400> SEQUENCE: 1
aagcugccag uugaagaacu gu                                            22

<210> SEQ ID NO 2
<211> LENGTH: 22
<212> TYPE: DNA
<213> ORGANISM: Homo sapiens

<400> SEQUENCE: 2
ugucaagaag uugaccgucg aa                                            22

<210> SEQ ID NO 3
<211> LENGTH: 23
<212> TYPE: DNA
<213> ORGANISM: Homo sapiens

<400> SEQUENCE: 3
agcagguccu aauguggcag cua                                           23

<210> SEQ ID NO 4
<211> LENGTH: 23
<212> TYPE: DNA
<213> ORGANISM: Mus musculus

<400> SEQUENCE: 4
agcugguccu gauguggcag cua                                           23
```